US008073105B2

(12) United States Patent
Gertner et al.

(10) Patent No.: US 8,073,105 B2
(45) Date of Patent: Dec. 6, 2011

(54) OCULAR RADIOSURGERY

(75) Inventors: Michael Gertner, Menlo Park, CA (US); Erik Chell, Oakland, CA (US); Steven D. Hansen, Concord, CA (US); Mark Arnoldussen, San Carlos, CA (US); Matt Herron, Palo Alto, CA (US); Kuang-Hung Pan, Mountain View, CA (US)

(73) Assignee: Oraya Therapeutics, Inc., Newark, CA (US)

( * ) Notice: Subject to any disclaimer, the term of this patent is extended or adjusted under 35 U.S.C. 154(b) by 0 days.

(21) Appl. No.: 12/725,406

(22) Filed: Mar. 16, 2010

(65) Prior Publication Data

US 2010/0172473 A1    Jul. 8, 2010

Related U.S. Application Data

(63) Continuation of application No. 11/873,386, filed on Oct. 16, 2007, now Pat. No. 7,680,244.

(60) Provisional application No. 60/933,220, filed on Jun. 4, 2007, provisional application No. 60/922,741, filed on Apr. 9, 2007, provisional application No. 60/869,872, filed on Dec. 13, 2006, provisional application No. 60/862,210, filed on Oct. 19, 2006, provisional application No. 60/862,044, filed on Oct. 18, 2006, provisional application No. 60/829,676, filed on Oct. 16, 2006.

(51) Int. Cl.
*A61N 5/10* (2006.01)

(52) U.S. Cl. ........................................................ 378/65

(58) Field of Classification Search ...................... 378/65
See application file for complete search history.

(56) References Cited

U.S. PATENT DOCUMENTS 3,073,960 A    1/1963   Guentner et al.
(Continued)

FOREIGN PATENT DOCUMENTS

EP             2152145 A1    2/2010
(Continued)

OTHER PUBLICATIONS

Georgopoulos, Michael et al., Tumour Regression of Uveal Melanoma after Ruthenium-106 Brachytherapy or Stereotactic Radiotherapy with Gamma Knife or Linear Accelerator, Ophthalmologica, 315-319 (2003).

(Continued)

*Primary Examiner* — Glen Kao
(74) *Attorney, Agent, or Firm* — James W. Hill; M. Todd Hales; McDermott Will & Emery LLP

(57) ABSTRACT

A radiosurgery system is described that is configured to deliver a therapeutic dose of radiation to a target structure in a patient. In some embodiments, inflammatory ocular disorders are treated, specifically macular degeneration. In some embodiments, the ocular structures are placed in a global coordinate system based on ocular imaging. In some embodiments, the ocular structures inside the global coordinate system lead to direction of an automated positioning system that is directed based on the ocular structures within the coordinate system. In some embodiments, the position of the ocular structure is tracked and related to the status of the radiosurgery system. In some embodiments, a treatment plan is utilized in which beam energy and direction and duration of time for treatment is determined for a specific disease to be treated and/or structures to be avoided. In some embodiments, the structure is an eye and the eye is tracked by the system. In some embodiments, the eye is held in place and in some embodiments, the eye is fixed by the patient. In some embodiments, a fiducial is placed on the eye to aid in positioning. In some embodiments, a reflection off the eye is used to aid in positioning. In some embodiments, radiodynamic therapy is described in which radiosurgery is used in combination with other treatments and can be delivered concomitant with, prior to, or following other treatments.

20 Claims, 35 Drawing Sheets

U.S. PATENT DOCUMENTS

| | | |
|---|---|---|
| 4,391,275 A | 7/1983 | Fankhauser et al. |
| 4,521,905 A | 6/1985 | Hosokawa |
| 4,710,193 A | 12/1987 | Volk |
| 4,718,418 A | 1/1988 | L'Esperance, Jr. |
| 4,817,432 A | 4/1989 | Wallace et al. |
| 5,008,907 A | 4/1991 | Norman et al. |
| 5,027,818 A | 7/1991 | Bova et al. |
| 5,065,031 A * | 11/1991 | Moscovitch ............... 250/486.1 |
| 5,116,115 A | 5/1992 | Lange et al. |
| 5,139,494 A | 8/1992 | Freiberg |
| 5,171,254 A | 12/1992 | Sher |
| 5,189,687 A | 2/1993 | Bova et al. |
| 5,207,223 A | 5/1993 | Adler |
| 5,216,255 A | 6/1993 | Weidlich |
| 5,304,167 A | 4/1994 | Freiberg |
| 5,336,215 A | 8/1994 | Hsueh et al. |
| 5,339,347 A | 8/1994 | Slatkin et al. |
| 5,354,323 A | 10/1994 | Whitebook |
| 5,373,844 A | 12/1994 | Smith et al. |
| 5,411,026 A | 5/1995 | Carol |
| 5,427,097 A | 6/1995 | Depp |
| 5,430,308 A | 7/1995 | Feichtner et al. |
| 5,446,548 A | 8/1995 | Gerig et al. |
| 5,468,238 A | 11/1995 | Mersch |
| 5,528,652 A | 6/1996 | Smith et al. |
| 5,556,417 A | 9/1996 | Sher |
| 5,635,721 A | 6/1997 | Bardi et al. |
| 5,644,616 A | 7/1997 | Landi et al. |
| 5,651,043 A | 7/1997 | Tsuyuki et al. |
| 5,668,847 A | 9/1997 | Hernandez |
| 5,708,696 A | 1/1998 | Kantor |
| 5,724,400 A | 3/1998 | Swerdloff et al. |
| 5,727,042 A | 3/1998 | Brenneisen |
| 5,737,384 A | 4/1998 | Fenn |
| 5,744,919 A | 4/1998 | Mishin et al. |
| 5,745,545 A | 4/1998 | Hughes |
| 5,771,270 A | 6/1998 | Archer |
| 5,778,043 A | 7/1998 | Cosman |
| 5,820,553 A | 10/1998 | Hughes |
| 5,870,697 A | 2/1999 | Chandler et al. |
| 5,901,199 A | 5/1999 | Murphy et al. |
| 6,001,054 A | 12/1999 | Regulla et al. |
| 6,104,778 A | 8/2000 | Murad |
| 6,126,668 A | 10/2000 | Bair et al. |
| 6,134,294 A | 10/2000 | Gibbs |
| 6,135,996 A | 10/2000 | Kolesa et al. |
| 6,144,875 A | 11/2000 | Schweikard et al. |
| 6,149,643 A | 11/2000 | Herekar et al. |
| 6,179,422 B1 | 1/2001 | Lai |
| 6,245,059 B1 | 6/2001 | Clapham |
| 6,257,722 B1 | 7/2001 | Toh |
| 6,260,005 B1 | 7/2001 | Yang et al. |
| 6,278,764 B1 | 8/2001 | Barbee, Jr. et al. |
| 6,287,299 B1 | 9/2001 | Sasnett et al. |
| 6,299,054 B1 | 10/2001 | Gibbs, Jr. |
| 6,299,307 B1 | 10/2001 | Oltean et al. |
| 6,301,328 B1 | 10/2001 | Sliski et al. |
| 6,301,329 B1 | 10/2001 | Surridge |
| 6,312,393 B1 | 11/2001 | Abreu |
| 6,359,963 B1 | 3/2002 | Cash |
| 6,385,286 B1 | 5/2002 | Fitchard et al. |
| 6,436,113 B1 | 8/2002 | Burba et al. |
| 6,459,762 B1 | 10/2002 | Wong et al. |
| 6,494,878 B1 | 12/2002 | Pawlowski et al. |
| 6,501,981 B1 | 12/2002 | Schweikard et al. |
| 6,512,813 B1 | 1/2003 | Krispel et al. |
| 6,535,574 B1 | 3/2003 | Collins et al. |
| 6,544,193 B2 | 4/2003 | Abreu |
| 6,560,312 B2 | 5/2003 | Cash |
| 6,690,965 B1 | 2/2004 | Riaziat et al. |
| 6,714,620 B2 | 3/2004 | Caflisch et al. |
| 6,728,335 B1 | 4/2004 | Thomson et al. |
| 6,744,846 B2 | 6/2004 | Popescu et al. |
| 6,778,850 B1 | 8/2004 | Adler et al. |
| 6,789,900 B2 | 9/2004 | Van De Velde |
| 6,792,073 B2 | 9/2004 | Deasy et al. |
| 6,810,107 B2 | 10/2004 | Steinberg |
| 6,837,862 B2 | 1/2005 | Driver, Jr. |
| 6,853,704 B2 | 2/2005 | Collins et al. |
| 6,863,667 B2 | 3/2005 | Webb et al. |
| 6,865,253 B2 | 3/2005 | Blumhofer et al. |
| 6,865,254 B2 | 3/2005 | Nafstadius |
| 6,875,165 B2 | 4/2005 | Dejuan, Jr. et al. |
| 6,888,919 B2 | 5/2005 | Graf |
| 6,937,696 B1 | 8/2005 | Mostafavi |
| 6,942,656 B2 | 9/2005 | Pawlowski et al. |
| 6,965,847 B2 | 11/2005 | Wessol et al. |
| 6,977,987 B2 | 12/2005 | Yamashita et al. |
| 6,990,175 B2 | 1/2006 | Nakashima et al. |
| 7,018,376 B2 | 3/2006 | Webb et al. |
| 7,027,557 B2 | 4/2006 | Llacer |
| 7,044,602 B2 | 5/2006 | Chernyak |
| 7,046,762 B2 | 5/2006 | Lee |
| 7,046,765 B2 | 5/2006 | Wong et al. |
| 7,070,327 B2 | 7/2006 | Collins |
| 7,070,554 B2 | 7/2006 | White et al. |
| 7,085,347 B2 | 8/2006 | Mihara et al. |
| 7,103,144 B2 | 9/2006 | Wong et al. |
| 7,103,145 B2 | 9/2006 | Wong et al. |
| 7,115,120 B2 | 10/2006 | Lin |
| 7,139,601 B2 | 11/2006 | Bucholz et al. |
| 7,154,991 B2 | 12/2006 | Earnst et al. |
| 7,158,607 B2 | 1/2007 | Dilmanian et al. |
| 7,158,610 B2 | 1/2007 | Mostafavi |
| 7,166,852 B2 | 1/2007 | Saracen et al. |
| 7,171,257 B2 | 1/2007 | Thomson |
| 7,178,666 B2 | 2/2007 | Huang |
| 7,179,254 B2 | 2/2007 | Pendekanti et al. |
| 7,187,792 B2 | 3/2007 | Fu et al. |
| 7,194,063 B2 | 3/2007 | Dilmanian et al. |
| 7,204,640 B2 | 4/2007 | Fu et al. |
| 7,221,733 B1 | 5/2007 | Takai et al. |
| 7,225,012 B1 | 5/2007 | Susil et al. |
| 7,227,925 B1 | 6/2007 | Mansfield et al. |
| 7,231,076 B2 | 6/2007 | Fu et al. |
| 7,239,684 B2 | 7/2007 | Hara et al. |
| 7,239,908 B1 | 7/2007 | Alexander et al. |
| 7,260,426 B2 | 8/2007 | Schweikard et al. |
| 7,266,176 B2 | 9/2007 | Allison et al. |
| 7,278,787 B2 | 10/2007 | Hack et al. |
| 7,280,865 B2 | 10/2007 | Adler et al. |
| 7,283,610 B2 | 10/2007 | Low et al. |
| 7,346,144 B2 | 3/2008 | Hughes et al. |
| 7,496,174 B2 | 2/2009 | Gertner et al. |
| 7,535,991 B2 | 5/2009 | Gertner |
| 7,564,946 B2 | 7/2009 | Gertner |
| 7,590,219 B2 | 9/2009 | Mauer et al. |
| 7,620,144 B2 | 11/2009 | Bodduluri |
| 7,620,147 B2 | 11/2009 | Gertner et al. |
| 7,680,244 B2 | 3/2010 | Gertner et al. |
| 7,680,245 B2 | 3/2010 | Gertner |
| 7,693,258 B2 | 4/2010 | Gertner |
| 7,693,259 B2 | 4/2010 | Gertner |
| 7,693,260 B2 | 4/2010 | Gertner et al. |
| 7,697,663 B2 | 4/2010 | Gertner |
| 7,792,249 B2 | 9/2010 | Gertner et al. |
| 7,801,271 B2 | 9/2010 | Gertner et al. |
| 7,822,175 B2 | 10/2010 | Gertner |
| 7,912,178 B2 | 3/2011 | Gertner |
| 7,912,179 B2 | 3/2011 | Gertner et al. |
| 7,953,203 B2 | 5/2011 | Gertner et al. |
| 7,961,845 B2 | 6/2011 | Gertner et al. |
| 7,978,818 B2 | 7/2011 | Gertner et al. |
| 7,978,819 B2 | 7/2011 | Gertner et al. |
| 2002/0051513 A1 | 5/2002 | Pugachev et al. |
| 2002/0065461 A1 | 5/2002 | Cosman |
| 2002/0099363 A1 | 7/2002 | Woodward et al. |
| 2002/0106054 A1 | 8/2002 | Caflisch et al. |
| 2002/0106055 A1 | 8/2002 | Cash |
| 2002/0115902 A1 | 8/2002 | Dejuan et al. |
| 2002/0161356 A1 | 10/2002 | Bille et al. |
| 2002/0198453 A1 | 12/2002 | Herrick, II |
| 2002/0198553 A1 | 12/2002 | Schumer et al. |
| 2003/0112922 A1 | 6/2003 | Burdette et al. |
| 2003/0120141 A1 | 6/2003 | Adler |
| 2003/0125622 A1 | 7/2003 | Schweikard et al. |
| 2003/0161826 A1 | 8/2003 | Arnason et al. |

| | | |
|---|---|---|
| 2003/0189689 A1 | 10/2003 | Rathjen |
| 2003/0211075 A1 | 11/2003 | Thorpe et al. |
| 2003/0219098 A1 | 11/2003 | McNutt et al. |
| 2004/0019274 A1 | 1/2004 | Galloway, Jr. et al. |
| 2004/0037390 A1 | 2/2004 | Mihara et al. |
| 2004/0054359 A1 | 3/2004 | Ruiz et al. |
| 2004/0071261 A1 | 4/2004 | Earl et al. |
| 2004/0131150 A1 | 7/2004 | Pankratov et al. |
| 2004/0138515 A1 | 7/2004 | White et al. |
| 2004/0267294 A1 | 12/2004 | Will |
| 2005/0010109 A1 | 1/2005 | Faul |
| 2005/0049478 A1 | 3/2005 | Kuduvalli et al. |
| 2005/0058245 A1 | 3/2005 | Ein-Gal |
| 2005/0111621 A1 | 5/2005 | Riker et al. |
| 2005/0175218 A1 | 8/2005 | Vertegaal et al. |
| 2005/0180544 A1 | 8/2005 | Sauer et al. |
| 2005/0192562 A1 | 9/2005 | Loesel et al. |
| 2005/0203499 A1 | 9/2005 | Pendekanti et al. |
| 2005/0226482 A1 | 10/2005 | Kuduvalli et al. |
| 2005/0228255 A1 | 10/2005 | Saracen et al. |
| 2005/0234327 A1 | 10/2005 | Saracen et al. |
| 2005/0270486 A1 | 12/2005 | Teiwes et al. |
| 2005/0271590 A1 | 12/2005 | Schwartz et al. |
| 2006/0002601 A1 | 1/2006 | Fu et al. |
| 2006/0002615 A1 | 1/2006 | Fu et al. |
| 2006/0002630 A1 | 1/2006 | Fu et al. |
| 2006/0002631 A1 | 1/2006 | Fu et al. |
| 2006/0002632 A1 | 1/2006 | Fu et al. |
| 2006/0004281 A1 | 1/2006 | Saracen |
| 2006/0033044 A1 | 2/2006 | Gentry et al. |
| 2006/0067469 A1 | 3/2006 | Dooley et al. |
| 2006/0072821 A1 | 4/2006 | Wang |
| 2006/0074292 A1 | 4/2006 | Thomson et al. |
| 2006/0074299 A1 | 4/2006 | Sayah |
| 2006/0074304 A1 | 4/2006 | Sayah |
| 2006/0078087 A1 | 4/2006 | Forman et al. |
| 2006/0084952 A1 | 4/2006 | Pallikaris et al. |
| 2006/0093089 A1 | 5/2006 | Vertatschitsch et al. |
| 2006/0170679 A1 | 8/2006 | Wang et al. |
| 2006/0170865 A1 | 8/2006 | Hirohara et al. |
| 2006/0176997 A1 | 8/2006 | Dilmanian et al. |
| 2006/0182326 A1 | 8/2006 | Schildkraut et al. |
| 2006/0192921 A1 | 8/2006 | Loesel et al. |
| 2006/0193441 A1 | 8/2006 | Cadman |
| 2006/0199991 A1 | 9/2006 | Lewis et al. |
| 2006/0203964 A1 | 9/2006 | Nyholm et al. |
| 2006/0245543 A1 | 11/2006 | Earnst et al. |
| 2006/0271025 A1 | 11/2006 | Jones et al. |
| 2006/0274061 A1 | 12/2006 | Wang et al. |
| 2006/0274885 A1 | 12/2006 | Wang et al. |
| 2006/0274924 A1 | 12/2006 | West et al. |
| 2006/0274925 A1 | 12/2006 | West et al. |
| 2006/0285641 A1 | 12/2006 | Scherch |
| 2006/0287662 A1 | 12/2006 | Berry et al. |
| 2006/0291621 A1 | 12/2006 | Yan et al. |
| 2006/0291710 A1 | 12/2006 | Wang et al. |
| 2006/0293583 A1 | 12/2006 | Saracen et al. |
| 2007/0003007 A1 | 1/2007 | Carrano et al. |
| 2007/0003123 A1 | 1/2007 | Fu et al. |
| 2007/0015991 A1 | 1/2007 | Fu et al. |
| 2007/0038058 A1 | 2/2007 | West et al. |
| 2007/0053490 A1 | 3/2007 | Wang et al. |
| 2007/0053491 A1 | 3/2007 | Schildkraut et al. |
| 2007/0071168 A1 | 3/2007 | Allison et al. |
| 2007/0071176 A1 | 3/2007 | Main et al. |
| 2007/0078306 A1 | 4/2007 | Allison et al. |
| 2007/0083087 A1 | 4/2007 | Carda |
| 2007/0093795 A1 | 4/2007 | Melcher et al. |
| 2007/0118010 A1 | 5/2007 | Hillstead et al. |
| 2007/0127622 A1 | 6/2007 | Main et al. |
| 2007/0127845 A1 | 6/2007 | Fu et al. |
| 2007/0140413 A1 | 6/2007 | Saracen |
| 2007/0169265 A1 | 7/2007 | Saracen et al. |
| 2007/0195929 A1 | 8/2007 | Ruchala et al. |
| 2007/0225691 A1 | 9/2007 | Silvestrini et al. |
| 2007/0225693 A1 | 9/2007 | Muehlhoff et al. |
| 2007/0249911 A1 | 10/2007 | Simon |
| 2008/0049896 A1 | 2/2008 | Kuduvalli |
| 2008/0056434 A1 | 3/2008 | Grozinger et al. |
| 2008/0159478 A1 | 7/2008 | Keall et al. |
| 2008/0187099 A1 | 8/2008 | Gertner |
| 2008/0187101 A1 | 8/2008 | Gertner |
| 2008/0192892 A1 | 8/2008 | Dilmanian et al. |
| 2008/0212737 A1 | 9/2008 | D'Souza et al. |
| 2008/0212738 A1 | 9/2008 | Gertner |
| 2008/0317312 A1 | 12/2008 | Carl et al. |
| 2009/0003525 A1 | 1/2009 | Gertner et al. |
| 2009/0163898 A1 | 6/2009 | Gertner et al. |
| 2009/0182310 A1 | 7/2009 | Gertner et al. |

FOREIGN PATENT DOCUMENTS

| | | |
|---|---|---|
| EP | 2231277 A2 | 9/2010 |
| WO | 0126591 A1 | 4/2001 |
| WO | 0235996 A1 | 5/2002 |
| WO | WO 03/039370 | 5/2003 |
| WO | 2006086631 A1 | 8/2006 |
| WO | WO 2007/027164 | 3/2007 |
| WO | 2007/045075 A1 | 4/2007 |
| WO | 2008/124801 A2 | 10/2008 |
| WO | 2008/150330 A1 | 12/2008 |
| WO | 2009/075714 A1 | 6/2009 |

OTHER PUBLICATIONS

Fakiris, Achilles J. et al., Gamma-Knife-Based Stereotactic Radiosurgery for Uveal Melanoma, Stereiotact. Funct. Neurosurg., 85:106-112 (2007).

Kirwan, James F. et al., Effect of β radiation on success of glaucoma drainage surgery in South Africa: randomized controlled trial, BMJ doi:10.1136/bmj.38971.395301.7C (Oct. 5, 2006).

Esquivel, Carlos Jr. et al., Novel low-kVp beamlet system for choroidal melanoma, Radiation Oncology I:36 (2006).

Kishi, Kazushi et al., Lead Contact Lens for Crystalline Lens Shielding in Electron Therapy for Eyelid Tumors, Radiation Medicine, vol. 14, No. 2, 107-109 (1996).

Bailey, Edgar D., CHP, Chief Radiologic Health Branch, "Syllabus on Radiography Radiation Protection, Filtration Regulatory Requirements," California Department of Health and Human Services, pp. 11-12 (2004).

Bangerter et al., "Forty Years' Experience with a Special, Non-Tumor Application of Radiotherapy for the Eye," European Journal of Medical Research, 1:582-588 (1996).

Cornsweet et al., "Accurate Two-Dimensional Eye Tracker Using First and Fourth Purkinje images," Journal of the Optical Society of America, 63(8):921-928, (1973).

Das et al., "Small Fields: Nonequilibrium Radiation Dosimetry," Medical Physics, 35(1):206-215 (2008).

Dieckmann et al., "A Linac-Based Stereotactic Irradiation Technique of Uveal Melanoma," Radiotherapy and Oncology, 61:49-56 (2001).

Francescon et al., "Total Scatter Factors of Small Beams: A Multidetector and Monte Carlo Study," Medical Physics 35(2):504-513 (2008).

Gao et al., "Orthovoltage Radiation Therapy Treatment Planning Using Monte Carlo Simulation: Treatment of Neuroendocrine Carcinoma of the Maxillary Sinus," Phys. Med. Biol., ISSN: 0031-9155; vol. 42, No. 12., pp. 2421-2433 (1997).

Jaywant et al., "Stereotactic Radiotherapy in the Treatment of Ocular Melanoma: A Noninvasive Eye Fixation Aid and Tracking System," Journal of Applied Clinical Medical Physics, 4(2):156-161 (2003).

Kim et al., "Combination hyperthermia and radiation therapy for malignant melanoma," Cancer, 50:478-482 (1982).

Kobayashi et al., Radiotherapy for subfoveal neovascularisation associated with pathological myopia: a pilot study., J. Ophth. 87:761-766 (2000).

Marcus et al., "External Beam Irradiation of Subfoveal Choroidal Neovascularization Complicating Age-Related Macular Degeneration," Arch Ophthalmology, 119:171-180 (2001).

Marcus et al., "The Age-Related Macular Degeneration Radiotherapy Trial (AMDRT): One Year Results from a Pilot Study," American Journal of Ophthalmology, 138:818-828 (2004).

Sagerman et al., "Radiation Techniques for the Treatment of Retinoblastoma and Orbital Tumors," Radiotherapy of Intraocular and Orbital Tumors, 2nd Revised Edition (2003), pp. 233-237.

Schilling et al., "Long Term Results After Low Dose Ocular Irradiation for Choroidal Haemangiomas," British Journal of Ophthalmology, 81:267-273 (1997).

Schipper et al., "Management of Retinoblastoma by Precision Megavoltage Irradiation," Dept. of Radiation Therapy of the Univ. Hospital and the Royal Dutch Eye Hospital, Utrecht, The Netherlands (1983), pp. 534-540.

Senan et al., "Design of Clinical Trails of Radiation Combined with Antiangiogenic Therapy," The Oncologist, 12 (4):465-477 (2007) (www://theoncologist.alphamedpress.org).

Toma et al., "External Beam Radiotherapy for Retinoblastoma: II Lens Sparing Technique," British Journal of Ophthalmology, 79:112-117 (1995).

PCT/US2008/004999, International Search Report and Written Opinion of the International Searching Authority, dated Sep. 2, 2008.

PCT/US2008/005101, International Search Report and Written Opinion of the International Searching Authority, dated Sep. 2, 2008.

PCT/US2008/012341, International Search Report and Written Opinion of the International Searching Authority, dated Feb. 5, 2009.

PCT/US2008/013886, International Search Report and Written Opinion of the International Searching Authority, dated May 22, 2009.

Bogner, J. et al. 2003. A Noninvasive Eye Fixation and Computer-Aided Eye Monitoring System for Linear Accelerator-Based Stereotactic Radiotherapy of Uveal Melanoma. International Journal of Radiation Oncology Biology Physics, vol. 56, No. 4, Jun. 20, 2001, pp. 1128-1136.

Petersch, B. et al. 2004. Automatic Real-Time Surveillance of Eye Position and Gating for Stereotactic Radiotherapy of Uveal Melanoma. Medical Physics, vol. 31, No. 12, Nov. 24, 2004, pp. 3521-3527.

Extended European Search Report, dated May 27, 2011, for European Patent Application No. 07873549.5-2305, filed Jul. 1, 2009 Applicant Oraya Therapeutics, entitled "Device and Assembly for Positioning, Stabilizing and Treating an Eye," based on PCT Application No. PCT/US2008/004999.

* cited by examiner

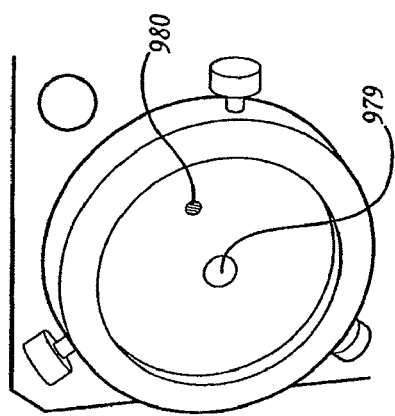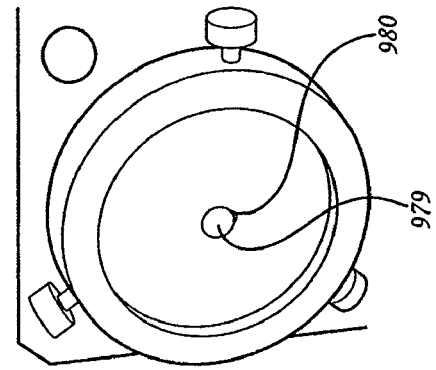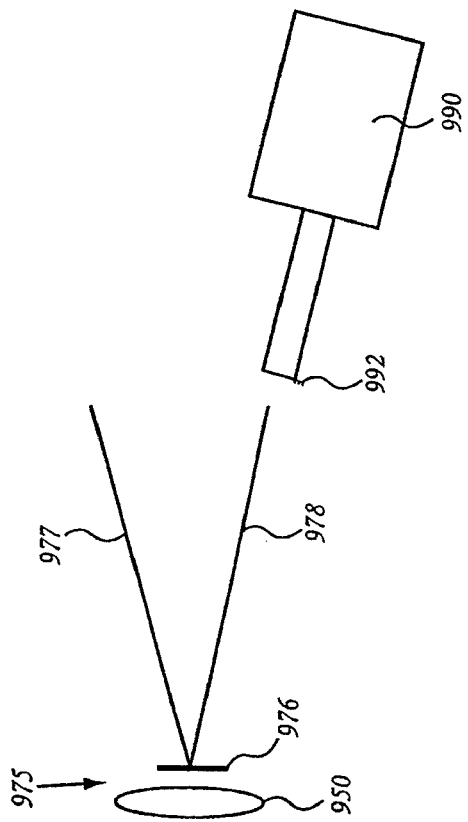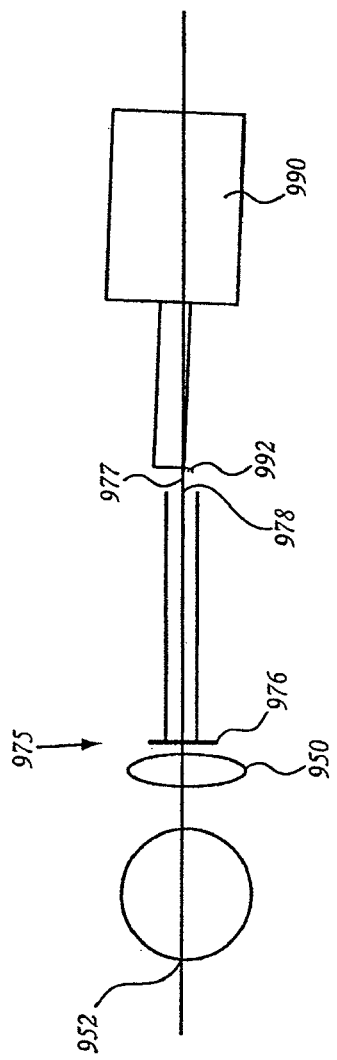
FIG. 1I
FIG. 1J

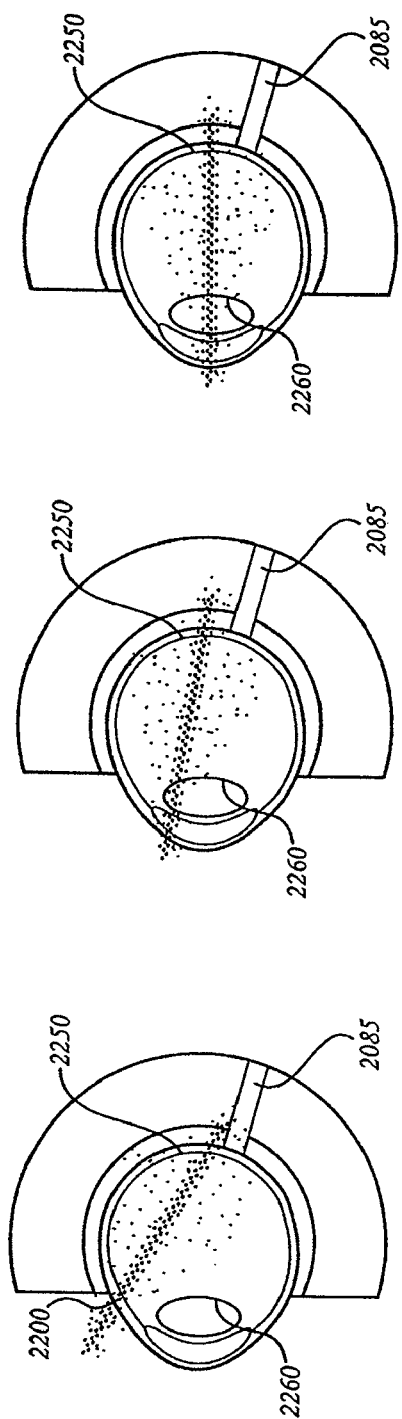
Beam 1
FIG. 7A
Beam 2
FIG. 7B
Beam 3
FIG. 7C
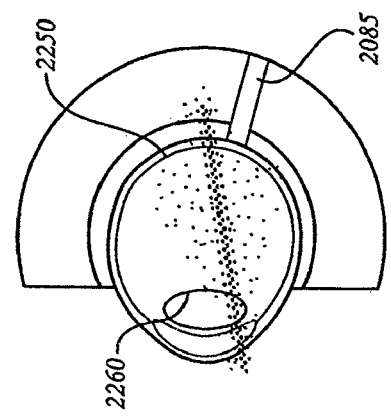
Beam 4
FIG. 7D
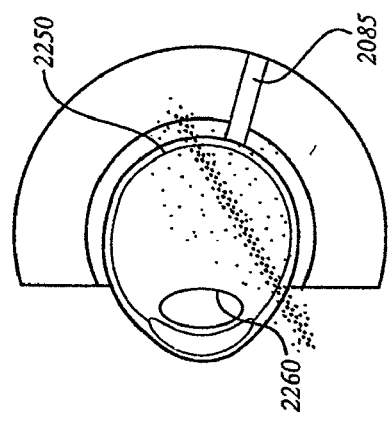
Beam 5
FIG. 7E

OCULAR RADIOSURGERY

RELATED APPLICATIONS

This application is a continuation of U.S. patent application Ser. No. 11/873,386, filed Oct. 16, 2007, entitled, "Ocular Radiosurgery," which claims priority benefit of U.S. Provisional Application No. 60/933,220, filed Jun. 4, 2007; U.S. Provisional Application No. 60/922,741, filed Apr. 9, 2007; U.S. Provisional Application No. 60/869,872, filed Dec. 13, 2006; U.S. Provisional Application No. 60/862,210, filed Oct. 19, 2006; U.S. Provisional Application No. 60/862,044, filed Oct. 18, 2006; and U.S. Provisional Application No. 60/829,676, filed Oct. 16, 2006; the entirety of each of which is incorporated herein by reference.

BACKGROUND

1. Field of the Inventions

This disclosure relates to the treatment of ocular disorders using targeted photon energy. In particular, the present disclosure relates to apparatus, systems, and methods for image-guided low energy x-ray therapy of ocular structures.

2. Description of the Related Art

Macular degeneration is a condition where the light-sensing cells of the macula, a near-center portion of the retina of the human eye, malfunction and slowly cease to work. Macular degeneration is the leading cause of central vision loss in people over the age of fifty years. Clinical and histologic evidence indicates that macular degeneration is in part caused by or results in an inflammatory process that ultimately causes destruction of the retina. The inflammatory process can result in direct destruction of the retina or destruction via formation of neovascular membranes which leak fluid and blood into the retina, quickly leading to scarring.

Many treatments for macular degeneration are aimed at stopping the neovascular (or "wet") form of macular degeneration rather than geographic atrophy, or the "dry" form of Age-related Macular Degeneration (AMD). All wet AMD begins as dry AMD. Indeed, the current trend in advanced ophthalmic imaging is that wet AMD is being identified prior to loss of visual acuity. Treatments for macular degeneration include the use of medication injected directly into the eye (Anti-VEGF therapy) and laser therapy in combination with a targeting drug (photodynamic therapy); other treatments include brachytherapy (i.e., the local application of a material which generates beta-radiation).

SUMMARY

Disclosed herein are systems, methods, and apparatus that provide treatment for ocular disorders by irradiating specific regions of the eye without substantially exposing the rest of the eye to radiation. In some embodiments described herein, radiotherapy systems are disclosed that may be used to treat a wide variety of medical conditions relating to the eye. For example, the systems may be used, alone or in combination with other therapies, to treat macular degeneration, diabetic retinopathy, inflammatory retinopathies, infectious retinopathies, tumors in the eye or around the eye, glaucoma, refractive disorders, cataracts, post-surgical inflammation of any of the structures of the eye, ptyrigium, and dry eye.

In some embodiments described herein, radiotherapy (or externally applied radiation therapy) is used for treatment of macular degeneration, and standard treatments for macular degeneration are disclosed. Radiotherapy treatment of macular degeneration presents several complications. For example, the eye contains several critical structures, such as the lens and the optic nerve, that can possibly be damaged by excessive exposure to radiation. The application of external beam therapy is limited by devices and methodologies used to apply the therapy. These devices and methodologies are older radiation technologies used to treat conditions such as tumors anywhere in the body and were not developed specifically for ocular radiation therapy. In addition, logistics are difficult as far as patient recruitment and administration of treatments because such treatment devices are borrowed from and displace oncologic therapies.

Stereotactic radiation therapy generally refers to the delivery of radiation beams from multiple directions to focus on a target. Such therapy is delivered using large linear accelerators or radioactive sources, such as Cobalt-60 (gamma knife). Robotic stereotactic surgery (e.g., see U.S. patent application Ser. No. 11/354,411, filed Feb. 14, 2006, entitled, "Adaptive X-ray Control," assigned to Accuray Inc., the entirety of which is hereby incorporated by reference) is an application of stereotactic radiation in which a large linear accelerator moves about a patient and delivers a series of radiation beams toward a target. Because the dose can be controlled around the target, while sparing normal tissue, the therapy can be delivered in a small number of fractionated doses. The procedure may be referred to as "radiosurgery" versus radiotherapy. In general terms, radiosurgery is one form of radiation therapy.

Retinal radiotherapy trials have shown stabilized or improved visual acuity without any significant toxicity. Radiation has also been shown to dry up neovascular membranes in patients and stabilize vision. However, due to limitations in the treatment of macular degeneration using radiotherapy, including localization of the region to be treated as well as specific application of the radiation to the region to be treated, macular radiotherapy often irradiates the entire retina, which is both unnecessary and possibly harmful. Moreover, the dose of radiation specifically to the macula has not been limited to multiple fractions over many days or weeks. The ability to apply a greater dose specifically to the macula in a period of time less than 24 hours will have a greater effect on the disease than was shown in previous trials.

Brachytherapy for wet AMD is also a powerful therapy to treat wet AMD (Neovista, Inc., Press Release, March 2007, the entirety of which is incorporated herein by reference). A major limitation of this treatment is that it requires invasive procedures involving partial removal of the vitreous fluid of the posterior chamber of the eye to place the brachytherapy probe. In addition, the ability to fractionate the dose is limited because of the invasiveness required to deliver the therapy. Furthermore, the therapy is dependent on exact placement by the surgeon and the stability of the surgeon's hand.

Other diseases of the eye include glaucoma. In this disease, surgery is often the second line of therapy after pharmaceutical therapy. Procedures such as trabeculoplasty, trabeculotomy, canaloplasty, laser iridotomy, placement of shunts, and other procedures all suffer from a short-lived effect because of scar formation as a result of the surgical trauma. Anti-inflammatory drugs appear to offer a palliative and/or preventative solution to the chronic scarring that occurs after these procedures; however, the drugs have to be given several times per day and are associated with their own side effect profile such as seepage into unwanted regions of the eye. Radiation doses (e.g., from about 5 Gy to about 20 Gy in some instances and about 10 Gy some embodiments) can be beneficial in the prevention of scarring after glaucoma surgery (see, e.g., Kirwan, et. al., Effect of Beta Radiation on Success of Glaucoma Drainage Surgery in South Africa: randomized controlled trial; British Medical Journal, Oct. 5, 2006, the entirety of which is herein incorporated by reference). Capsular opacification is a common occurrence after cataract procedures with placement of intraocular lenses (add reference). This scarring is caused by trauma from the surgery, proliferation of lens cells, and material incompatibility.

Another disease of the eye that is treatable with the systems, methods, and apparatus disclosed herein is pterygia of the eye. A pterygium is an elevated, superficial, external ocular mass that usually forms over the perilimbal conjunctiva and extends onto the corneal surface. Pterygia can vary from small, atrophic quiescent lesions to large, aggressive, rapidly growing fibrovascular lesions that can distort the corneal topography, and in advanced cases, can obscure the optical center of the cornea. The exact cause of pterygia is not well understood, although it occurs more often in people who spend a great deal of time outdoors, especially in sunny climates, and has been linked to long-term exposure to sunlight, especially ultraviolet rays, and chronic eye irritation from dry, dusty, and windy conditions. Pterygia can become inflamed, and the symptoms are often treated with topical eyedrops or ointments that can help to reduce the inflammation. If the pterygium is large enough to threaten sight, or encroaches on the cornea, the lesion is typically treated by surgical removal before vision is affected. However, even with most surgical techniques, the recurrence rate is often as high as 50 to 60 percent. The systems, methods, and apparatus disclosed herein can be used postoperatively to reduce the likelihood of recurrence of a pterygium by administration of radiation doses, and in some embodiments, doses of radiation can be used to slow or stop progression of the pterygium prior to surgery. (See, e.g., "Long-term results of non-surgical, exclusive strontium/yttrium-90 beta irradiation of pterygia," Radiation and Oncology 74 (2005) 25-29; the entirety of which is incorporated herein by reference).

In some embodiments, the radiation treatment system is used concomitantly with laser therapy. That is, rather than using a laser solely for pointing the x-ray device to the ocular target of choice, the laser is used for both pointing and therapy. In these embodiments, the laser preferably includes at least one additional energy or wavelength suitable for therapy of an ocular structure. The x-ray is preferably applied to the same region as the laser so as to limit or reduce excessive scarring around the laser therapy. For example, some embodiments of the systems and methods can be used in connection with glaucoma treatment, such as, for example, a trabeculectomy, in which the laser is used to create perforations or apertures in the trabecular meshwork of an eye while the x-ray, or radiation doses, are applied to limit or reduce scarring.

In some embodiments, the system can be configured to provide a source of heat, to heat the target tissue, and the x-rays are applied in conjunction with the heating of the target tissue. The term "applying in conjunction," in this context, can be applying the x-rays in preparation for applying the heat to the tissue, applying the x-rays following applying the heat to the tissue, or applying the x-rays at the same time as heat is applied to the tissue. The x-rays can be applied from about 2 and about 10 days prior to the treatment of the heat, and in some embodiments, the x-rays can be applied from about 2 and about 10 days following the treatment of the heat. In some embodiments, the x-rays are applied in a period that is less than about 2 days prior to treatment of the heat, and in some embodiments, the x-rays are applied in a period that is less than about 2 days following the treatment of the heat. In some embodiments, the x-rays are applied more than about 10 days prior to treatment of the tissue with heat, and in some embodiments, the x-rays are applied more than about 10 days following treatment of the tissue with heat. In some embodiments, variations of these treatment methods may be used. For example, multiple treatments of the target tissue with heat can be applied before and after the x-ray application. In another example, multiple treatments of the target tissue with x-rays can be applied before and after the treatment of the target tissue with heat. In some embodiments, treatment at substantially the same time can include treatment of the target tissue with heat and x-rays within about 72 hours, 48 hours, 36 hours, 24 hours, 12 hours, 6 hours, 2 hours, 1 hour, 30 minutes, 10 minutes, and 1 minute of each other. In some embodiments, treatment at substantially the same time can include treatment of the target tissue with heat and x-rays within about 1 week, 2 weeks, 3 weeks, and a month of each other.

In some embodiments, laser therapy is applied through a needle, the needle penetrating through eye tissue. For example, a needle or cannula can be placed through the sclera of the eye and into the vitreous to deliver a drug. The needle or cannula can also be used to direct a light pointer beam such as a laser pointer. The light pointer can be pointed to the retina and the lighted region on the retina visualized through a lens. A radiotherapy device can then be aligned, such as, for example, to be collinear, with the cannula and an x-ray beam can be emitted in an aligned trajectory with the laser pointer and intersect the retina at the same place as the laser pointer. In these embodiments, a target on the retina can be identified, targeted, and treated with the systems, methods, and apparatus described herein.

In some embodiments of this disclosure, electromotive and ocular imaging systems are utilized, but laser therapy is the sole radiation energy source used for treatment. In these embodiments, the ability of the system to focus radiation by passing the photons through the sclera from different angles to structures deep to the sclera can be utilized to treat diseases of the anterior chamber or posterior chamber with laser radiation while keeping the x-ray generation system off. In some embodiments, the x-ray generator is not included in the system. In these embodiments, the eye model, tracking, control, and focusing systems for the x-ray therapy are utilized for laser therapy.

In certain embodiments, a device, using a treatment planning system, is disclosed for providing targeted radiotherapy to specific regions of the eye. The treatment planning system integrates physical variables of the eye and disease variables from the physician to direct the x-ray system to deliver therapy to the ocular structures. The device applies narrow beams of radiation from one or more angles to focus radiation to a targeted region of the eye. In certain embodiments, the device may focus radiation beams to structures of the posterior eye, such as the retina. In certain embodiments, the device may focus radiation beams to structures of the anterior region of the eye, such as the sclera, the cornea, or the trabecular meshwork. The treatment planning system allows for planning of the direction of the beam entry into the eye at different points along the eye's surface, for example, the sclera. The unique anatomy of each individual is integrated into the treatment planning system for accurate targeting, and in some instances, automated positioning and orienting of the x-ray beams of the device.

In some embodiments described herein, treatment systems are provided for delivering radiation to a patient that include an eye model derived from anatomic data of a patient's eye, an emitter that emits a radiation beam, and a position guide, coupled to the emitter, that positions, based on the eye model, the emitter with respect to a location on or in the eye, such that the radiation beam is delivered to a target on or in the eye.

In some embodiments, the location comprises the target. The emitter can be configured to deliver the radiation beam with a photon energy between about 10 keV and about 500 keV or to deliver an radiation beam adjustable between about 25 keV and about 100 keV. In some embodiments, the radiation beam includes an x-ray beam. In some embodiments, the system further includes a planning module configured to determine, based on the eye model, at least two of a beam target, a beam intensity, a beam energy, a beam trajectory, a treatment field size, a treatment field shape, a distance from the emitter to the target, an exposure time, and a dose.

The position guide, in some embodiments, positions the emitter, based on information from the planning module, such that the emitter directs a first radiation beam at a first position through a first portion of the eye to a treatment region within the eye. The position guide preferably positions the emitter, based on information from the planning module, such that the emitter directs a second radiation beam at a second position through a second portion of the eye to the treatment region within the eye. In some embodiments, the planning module is adapted to receive input from a user, the input affecting an output of the planning module. In some embodiments, the system includes a sensing module that senses a position of the eye and relays information concerning the position of the eye to the planning module.

The system includes, in some embodiments, a sensing module that senses a position of the eye and relays information concerning the position of the eye to the position guide. The sensing module can include a portion that physically contacts the eye, which can include a lens positionable on or over the cornea of the eye. The sensing module can, in some embodiments, optically sense the position of the eye with, for example, a laser.

In some embodiments, the system also includes a collimator that collimates the radiation beam to a width of from about 0.5 mm to about 6 mm. The collimated beam can also have a penumbra of less than about ten percent at a distance up to about 50 cm from the collimator. The position guide, in some embodiments, is configured to position the emitter, in use, at a first distance within 50 cm of the target, such that the emitter delivers the radiation beam to the target from the first distance. In some embodiments, a collimator is positioned, in use, to within about 10 cm of the target when the radiation beam is delivered to the target.

The system can further include a detector that detects if the patient's eye moves such that the radiation beam is not directed to the target. In some embodiments, the emitter is configured to automatically not emit the radiation beam if the patient's eye moves out of a predetermined position or range of positions. Some embodiments include a laser emitter that emits a laser beam that passes through a collimator and is directed toward the eye and in some embodiments, is applied along the same axis as the x-ray emitter.

Some embodiments described herein disclose a system for delivering radiation to an eye that includes an eye model derived from anatomic data of a patient's eye, an emitter that delivers an x-ray beam to the eye with an energy from about 10 keV to about 500 keV, a position guide, coupled to the emitter, that positions, based on the eye model, the emitter with respect to a location in or on the eye, to deliver the x-ray beam to a target in or on the eye, and a planning module that determines at least two parameters of treatment based on the model of the eye. In some embodiments, the at least two parameters include two of a beam target, a beam intensity, a beam energy, a beam trajectory, a treatment field size, a treatment field shape, a distance from the emitter to the target, an exposure time, and a dose.

The position guide, in some embodiments, is configured to direct a first x-ray beam from a first position to a first region of a sclera of the eye to target a region of the eye, and is further configured to direct a second x-ray beam from a second position to a second region of the sclera to target substantially the same region of the eye. In some embodiments, the region of the eye is at least one of the macula, the sclera, the trabecular meshwork, and a capsule of the lens of the eye.

The system can further include a collimator that collimates the x-ray beam. In some embodiments, the collimator is configured to collimate the x-ray beam to a width of from about 0.5 mm to about 6 mm, and in some embodiments, the system is configured to produce an x-ray beam having a penumbra of less than about five percent within a distance, from the collimator to the target, of about 50 cm. The emitter, in some embodiments, is configured to deliver an x-ray beam with a photon energy between about 25 keV and about 150 keV. In some embodiments, the collimator is positioned, in use, to within about 10 cm of the target when the x-ray beam is delivered to the target.

In some embodiments, a treatment system for delivering radiation to a human being is provided, the system including an eye model derived from anatomic data of a patient's eye; an emitter that delivers an x-ray beam to the eye; and means for positioning the emitter, with respect to a location on or in the eye, to deliver the x-ray beam to a target on or in the eye, the means being coupled to the emitter, and the positioning of the emitter being based on the eye model.

Some embodiments provide a treatment system for delivering radiation to a patient that includes an emitter that generates a radiation beam, and a position guide, coupled to the emitter, operable to positions the emitter with respect to a location on or in the eye, to deliver the radiation beam to a target on or in the eye, wherein the emitter is placed within 50 cm of the target. In some embodiments, the system further includes a collimator coupled to the emitter, the collimator being placed, in use, to within 10 cm of the target when the emitter emits the radiation beam. In some embodiments, the system further includes a collimated laser emitter that is coupled to the emitter.

In some embodiments described herein, a method of treating macular degeneration of an eye is disclosed. The method preferably includes providing a model of an eye of a patient with anatomic data obtained by an imaging apparatus, producing an x-ray beam with a width of from about 0.5 mm to about 6 mm and having a photon energy between about 40 keV and about 100 keV, and in some embodiments between about 40 keV and about 250 keV, directing the x-ray beam such that the beam passes through the sclera to the retina of the eye, and exposing the retina to from about 1 Gy to about 40 Gy of x-ray radiation.

In some embodiments, the method provides that at least one of the x-ray beam width, photon energy, and direction of the x-ray beam is determined based on the model of the eye. The method further provides, in some embodiments, that the retina is exposed to from about 15 Gy to about 25 Gy of x-ray radiation. In some embodiments, treatment with the x-ray radiation can be fractionated, and a planning system can keep track of the quantity and location of prior treatments. In some embodiments, the method includes reducing neovascularization in the eye by exposing the retina to the radiation. The method may further include administering to the patient at least one of heating, cooling, vascular endothelial growth factor (VEGF) antagonist, a VEGF-receptor antagonist, an antibody directed to VEGF or a VEGF receptor, a modality which increases DNA strand breaks or decreases DNA repair, a modality which increases the level of apoptosis, a modality which increases endothelial cell death, a taxane or other microtubule inhibitor, a topoisomerase inhibitor such as irinotecan, a pharmaceutical in the limus family such as sirolimus, a compound which methylates DNA such as temozolomide, an analogue or prodrug of 5-fluorouracil such as capecitabine, a free radical inducing agent such as tirapazamine, small molecule tyrosine kinase inhibitors such as gefitinib or erlotinib, NFκB inhibitors or downregulators such as bortezomib, microwave energy, laser energy, hyperbaric oxygen, supersaturated oxygen, ultrasound energy, radiofrequency energy, and a therapeutic agent, prior to, or after, exposing the retina to the radiation. The method further includes, in some embodiments, directing a first x-ray beam to pass through the sclera to the retina from a first position external to the eye, and directing a second x-ray beam to pass through the sclera to the retina from a second position external to the eye. In some embodiments, the x-ray beam is directed to pass through a pars plana of the eye. The x-ray beam is, in some embodiments, directed to a macula of the eye.

Some embodiments herein describe a method of treating an eye of a patient that includes providing a model of the eye based on anatomic data obtained by an imaging apparatus, producing a first x-ray beam and a second x-ray beam, each beam having a width of from about 0.5 mm to about 6 mm, directing the first x-ray beam such that the first beam passes through a first region of a sclera of the eye to a target of a retina, and directing the second x-ray beam such that the second beam passes through a second region of the sclera to substantially the same target of the retina as the first beam, wherein the first region and second region of the sclera through which the first beam and second beam pass are selected based on the model of the eye.

In some embodiments, a trajectory of the first beam is determined based on the model of the eye, and in some embodiments, the directing of the first x-ray beam and the directing of the second x-ray beam occur sequentially. In some embodiments, the first x-ray beam and the second x-ray beam have photon energies of from about 25 keV to about 100 keV. Centers of the first and second x-ray beams, in some embodiments, are projected through a point on the sclera at a distance of from about 0.5 mm to about 6 mm from a limbus of the eye. In some embodiments, the method further includes administering to the patient at least one of heating, cooling, VEGF antagonist, a VEGF-receptor antagonist, an antibody directed to VEGF or a VEGF receptor, microwave energy, radiofrequency energy, laser energy, and a therapeutic agent, prior to, concurrently with, or subsequent to the directing of the first x-ray beam. The x-ray beam, in some embodiments, is produced by an x-ray source positioned less than about 50 cm from the retina. In some embodiments, the x-ray beam is emitted from a source having an end that is placed within about 10 cm of the eye. In some embodiments, the retina is exposed to about 15 Gy to about 25 Gy in some embodiments, and, in some embodiments to about 35 Gy, of x-ray radiation during one treatment session.

Some embodiments described herein relate to a method of treating an eye of a patient that includes providing a model of the eye based on anatomic data obtained by an imaging apparatus, producing a first x-ray beam and a second x-ray beam, each beam having a width of from about 0.5 mm to about 6 mm, directing the first x-ray beam such that the first beam passes through a first region of the eye to a target within the eye, and directing the second x-ray beam such that the second beam passes through a second region of the eye to substantially the same target within the eye, wherein the first region and second region of the eye through which the first beam and second beam pass are selected based on the model of the eye.

The target, in some embodiments, includes the lens capsule of the eye. In some embodiments, the target includes the trabecular meshwork of the eye or a tumor. In some embodiments, the first region comprises the cornea of the eye. In some embodiments, the first x-ray beam and the second x-ray beam have photon energies of from about 25 keV to about 100 keV. In some embodiments, the first and second x-ray beams are collimated by a collimator positioned within 10 cm of the eye, and in some embodiments, the x-ray beams are produced by an x-ray source positioned within 10 cm of the eye. The x-ray source can also be positioned within 50, 40, and/or 10 cm of the eye.

In some embodiments, the first region of the eye includes a first region of a sclera and the second region of the eye comprises a second region of the sclera, and an edge-to-edge distance from the first region of the sclera to the second region of the sclera is from about 0.1 mm to about 2 mm. In some embodiments, the first and second x-ray beams are directed from a nasal region external to the eye. Some methods further include aligning the center of the patient's eye with the x-ray radiotherapy system. Some methods also include developing a plan to treat a macular region using the model of the eye, wherein the first and second x-ray beams overlap at the macular region, and the first and second x-ray beams are collimated to from about 0.5 mm to about 6 mm.

Some embodiments described herein disclose a method of applying radiation to the retina of a patient's eye, the method including localizing the macula of the patient with an imaging device, linking the macula to a global coordinate system, and applying an external beam of radiation to the macula based on the coordinate system.

Some embodiments further include contacting a material to the sclera of the eye, the material being linked or trackable to the global coordinate system. In certain embodiments, motion of the external beam radiation is automated based on the coordinate system. In some embodiments, the method also includes detecting eye movements. Some embodiments further include recalculating the relationship between the macula and the coordinate system after a detection of eye movement. In some embodiments, the method further includes implanting a fiducial marker inside the eye to couple the eye and the retina to the coordinate system. In some embodiments, the external beam radiation is focused external beam radiation.

Described herein are embodiments that disclose a method of planning radiation treatment to an eye of a patient. In some embodiments, the method includes obtaining imaging data of the retina of the patient, coupling the imaging data to a global coordinate system, using a laser to enable alignment and targeting of focused ionizing radiation beams to the retina, and applying automated focused external beam therapy to the retina based on the position of the retina in the global coordinate system.

Some embodiments provide a method of treating a region of an eye of a patient that includes producing an x-ray beam with a width of from about 0.5 mm to about 6 mm and having a photon energy between about 40 keV and about 250 keV, directing the x-ray beam toward the eye region, and exposing the region to a dose of from about 1 Gy to about 40 Gy of x-ray radiation, thereby treating the region of the eye.

In some embodiments, the method further includes providing a model of the eye with anatomic data obtained by an imaging apparatus, wherein at least one of a width of the x-ray beam, a photon energy of the x-ray beam, and a direction of the x-ray beam is determined based on the model of the eye.

The region, in some embodiments, is exposed to from about 15 Gy to about 25 Gy of x-ray radiation, and in some embodiments, the region includes a retina of the eye. The treating can include reducing neovascularization in the eye by exposing the retina to the radiation, and/or substantially preventing progression from Dry Age-related Macular Degeneration (AMD) to neovascularization. In some embodiments, the method also includes administering to the patient at least one of heating, cooling, VEGF antagonist, a VEGF-receptor antagonist, an antibody directed to VEGF or a VEGF receptor, microwave energy, radiofrequency energy, a laser, a photodynamic agent, and a radiodynamic agent, and a therapeutic agent. Some embodiments further include directing a first x-ray beam to pass through a sclera to a retina from a first position external to the eye, and directing a second x-ray beam to pass through the sclera to the retina from a second position external to the eye. The x-ray beam, in some embodiments, is directed through a pars plana of the eye, and in some embodiments, the x-ray beam is directed to a macula of the eye. The x-ray beam can also be directed through a sclera of the eye to the macula of the eye.

Some embodiments provide that the dose is divided between two or more beams, and in some embodiments, the dose is divided between two or more treatment sessions, each of said treatment sessions occurring at least one day apart. Some methods described herein further include determining a position of the eye relative to the x-ray beam during the exposing of the region to the x-ray radiation, and shutting off the x-ray beam if the position of the eye exceeds a movement threshold.

Some methods of treating an eye of a patient described herein include providing a model of the eye based on anatomic data obtained by an imaging apparatus, directing a first x-ray beam such that the first beam passes through a first region of the eye to a target within the eye, and directing a second x-ray beam such that the second beam passes through a second region of the eye to substantially the same target within the eye, wherein the first region and second region of the eye through which the first beam and second beam pass are selected based on the model of the eye, and assessing a position of the eye during at least one of the administration of the first x-ray beam to the target, administration of the second x-ray beam to the target, and a period of time between administration of the first x-ray beam to the target and administration of the second x-ray beam to the target.

Some methods provide that the assessing occurs during administration of the first x-ray beam to the target, and some methods further include ceasing or reducing administration of the first x-ray beam when the eye moves beyond a movement threshold. Some methods further include directing the second x-ray beam based on information from the assessing of the position of the eye.

Some methods provide a method, of planning radiation therapy for an eye, including the steps of preparing a treatment plan for a delivery of an actual dose of radiation to a target at a region of the eye from at least one radiation beam, the preparing that includes determining a first estimated dose of radiation, to be delivered from a radiation source outside the eye to the target; determining a second estimated dose of radiation, to be received by at least one of the optic nerve and the lens of the eye from the radiation source; and wherein the second estimated dose of radiation is equal to or less than about 40 percent of the first estimated dose; and wherein the treatment plan comprises at least one of a width of the at least one radiation beam, a distance from the radiation source to the target, a trajectory of the beam, a maximum beam energy, and the first estimated dose of radiation; and wherein the at least one of the width of the at least one radiation beam, the distance from the radiation source to the target, the trajectory of the beam is selected to effect delivery of the first estimated dose to the target and the second estimated dose to the at least one of the optic nerve and the lens of the eye; and outputting information indicative of the treatment plan to an output module.

In some embodiments, at least one of the estimated dose of radiation to be received at the optic nerve and the estimated dose of radiation to be received at the lens is equal to or less than 20 percent of the estimated dose of radiation to be delivered to the target. In some embodiments, at least one of the estimated dose of radiation to be received at the optic nerve and the estimated dose of radiation to be received at the lens is equal to or less than 10 percent of the estimated dose of radiation to be delivered to the target. In some embodiments, at least one of the estimated dose of radiation to be received at the optic nerve and the estimated dose of radiation to be received at the lens is equal to or less than 5 percent of the estimated dose of radiation to be delivered to the target. In certain embodiments, at least one of the estimated dose of radiation to be received at the optic nerve and the estimated dose of radiation to be received at the lens is equal to or less than 1 percent of the estimated dose of radiation to be delivered to the target.

In certain embodiments, the output module comprises at least one of a computer monitor, an LCD, an LED, a handheld device, a paper, a computer-readable medium, a computer-executable instruction, and a communication link to the radiation source. Some embodiments, further includes delivering thermal energy to the eye during a period of between about 10 days before and about 3 days after delivery of the actual dose of radiation to the target.

In some embodiments, the method further includes delivering the actual dose of radiation to the target. In some embodiments, at least one of the estimated dose of radiation to be delivered to the target, the estimated dose of radiation to be received at the optic nerve, and the estimated dose of radiation to be received at the lens is determined by a Monte Carlo simulation. In some embodiments, at least one of the at least one radiation beam has a cross-sectional shape that is geometric. In some embodiments, the geometric cross-sectional shape comprises at least one of an ellipse, a circle, a ring, concentric rings, a polygon, and a crescent. In some embodiments, at least one of the estimated dose of radiation to be received at the optic nerve and the estimated dose of radiation to be received at the lens is based on a surface-to-depth beam energy representation. In some embodiments, at least one of the estimated dose of radiation to be received at the optic nerve and the estimated dose of radiation to be received at the lens is based on tracing diverging rays from an x-ray source with a maximum beam energy less than about 250 keV.

In some embodiments, a method is disclosed that includes determining trajectories of a plurality of radiation beams to be delivered to the target, such that each of the plurality of beams traverses the sclera at a respective traversal zone; and wherein none of the traversal zones overlaps substantially with any other of the intersection zones.

In some embodiments, at least one of the plurality of beams overlaps with another of the plurality of beams at the target. Some embodiments further include collimating the at least one radiation beam to a size having a cross-sectional dimension that is less than about 6 mm. Some embodiment further include determining a filtration amount such that a dose of radiation to an exterior surface of the eye is less than 3 times a dose of radiation to the target, wherein the at least one radiation beam having an energy of from about 50 KeV to about 300 KeV.

In some embodiments, the first x-ray beam is filtered with a filter which at least partly comprises a heavy metal. Some embodiments, further includes determining a current from about 1 mA to about 40 mA to be applied to a radiotherapy system such that a therapeutic dose of radiation to the target is administered in less than about 30 minutes. In some embodiments, the x-ray beam is collimated and wherein said collimator is placed within about 20 centimeters of the target. Some embodiments further include determining a direction of the at least one radiation beam to minimize the estimated dose of radiation to the optic nerve, and wherein the first x-ray beam is delivered from a nasal direction to a temporal direction or from an inferior direction to a superior direction with respect to delivery from outside the eye to the target inside the eye.

Some embodiments relate to a method, of planning radiation therapy for an eye, including preparing a treatment plan for a delivery of an actual dose of radiation to a target at a region of the eye from at least one radiation beam, the preparing including: determining a first estimated dose of radiation, to be delivered from a radiation source outside the eye to the target; determining a second estimated dose of radiation, to be received from the radiation source at other eye tissue, the other eye tissue located less than about 6 mm from a center of the target; and wherein the second estimated dose of radiation is equal to or less than about 40 percent of the first estimated dose; and wherein the treatment plan comprises at least one of a width of the at least one radiation beam, a distance from the radiation source to the target, a trajectory of the beam, and the first estimated dose of radiation; and wherein the at least one of the width of the at least one radiation beam, the distance from the radiation source to the target, the trajectory of the beam is selected to effect delivery of the first estimated dose to the target and the second estimated dose to the other eye tissue; and outputting information indicative of the treatment plan to an output module.

Some embodiments relate to a method, of treating an eye during a treatment period, including directing radiation from a source outside an eye to a target in or on the retina of the eye, such that a dose of radiation is emitted during the treatment period to at least one of the optic nerve and the lens of the eye is no more than about 40 percent of a dose of radiation delivered to the target. In some embodiments, the radiation is directed substantially through the pars plana of the eye.

In some embodiment a method, of treating an eye during a treatment period, is described that includes directing radiation from a source outside an eye to a target in the eye, such that a dose of radiation emitted during the treatment period to eye tissue located less than about 6 mm from a center of the target is no more than about 40 percent of the dose of radiation emitted to the target.

Some embodiments describe a method, of treating inflammation in a patient's eye, including the following: based on data indicative of a location of a region of inflammation in an eye, directing at least one x-ray beam from a source outside the eye, through an anterior region of the eye, to the region of inflammation, such that a dose of radiation emitted during the treatment period to eye tissue greater than about 6 mm from a center of the region of inflammation is no more than about 40 percent of the dose of radiation emitted to the region of inflammation.

In some embodiments, the region comprises drusen. In some embodiments, the anterior region of the eye is the cornea. In some embodiments, the anterior region of the eye is a sclera outside of a cornea of the eye. In some embodiments, the at least one x-ray beam has a cross-sectional dimension smaller than about 1 mm. In some embodiments, the beam has a diameter of between about 1 mm and about 5 mm. In some embodiments, the at least one x-ray beam comprises alternating regions of higher intensity and lower intensity. In some embodiments, the method further comprising directing a radiotherapy system at the eye at an angle with respect to a treatment axis that is determined using a device that contacts the eye. In some embodiments, the device communicates data relating to the eye optically with said radiotherapy system. Some embodiments, further include directing a radiotherapy system at the eye at an angle with respect to a treatment axis that is determined using an eye-contacting device. Some embodiments, further comprising directing a radiotherapy system at the eye at an angle to a treatment axis that is determined using one of a reflection of light off the eye, a fundus image, an image of a pupil of the eye, and an image of a limbus of the eye.

In some embodiments, a method, of delivering radiation to an eye, is described including providing an anterior-posterior axis of the eye; defining a treatment axis relative to the anterior-posterior axis of the eye; aligning a collimator at an angle relative to the treatment axis, the collimator being configured to collimate an x-ray beam that is emitted toward the eye, the collimated x-ray beam having a cross-sectional dimension of less than about 6 mm; and emitting the x-ray beam at an angle relative to the treatment axis.

In some embodiments, the collimated x-ray beam has a penumbra of less than about 20 percent at about 10 cm from the collimator. In some embodiments, the treatment axis is an optical central axis of the eye. In some embodiments, the treatment axis is a visual axis of the eye. In some embodiments, the treatment axis is perpendicular to a center of the limbus or cornea. Some embodiments further include moving the collimated radiation beam relative to the treatment axis and emitting a second collimated x-ray beam. Some embodiments further include moving the eye relative to the collimated radiation beam. Some embodiments, further include aligning the collimated x-ray beam with a projected spot on the sclera of the eye. In some embodiments, the spot is aligned with the treatment axis. In some embodiments, the spot is aligned with the collimated x-ray beam. In some embodiments, emitting the collimated x-ray beam is based on a treatment planning software program.

In some embodiments, described is a method, of treating an ocular structure of an eye with a radiation beam from a radiotherapy system, including contacting a surface of the eye with an eye contact member, wherein the eye contact member comprises a first portion, such that an axis passing through the ocular structure also passes through the first portion of the eye contact member; and emitting a plurality of radiation beams toward the ocular structure, from a radiotherapy system located outside the eye, such that the plurality of radiation beams each have a trajectory that intersects the axis at a treatment site at the ocular structure, the treatment site being effectively treatable by at least one of the plurality of radiation beams.

Some embodiments further include substantially fixing the eye in a first position with the eye contact member. In some embodiments, the eye contact member comprises a transmissive portion that transmits a first wavelength of electromagnetic radiation from outside to inside the eye. In some embodiments, the first portion is reflective of a second wavelength of electromagnetic radiation. In some embodiments, the first portion is centrally located in or on the eye contact member. In some embodiments, at least one of the plurality of radiation beams comprises laser light. In some embodiments, In some embodiments, at least one of the plurality of radiation beams comprises x-rays.

In some embodiments, described is a patient ocular interface, for treatment of an ocular structure with a radiotherapy system, including an eye holder, having an eye-contacting surface that engages an outer surface of an eye, that maintains the eye in substantially a first position; and wherein the eye holder is configured to provide an indication to a sensor that the eye is in substantially the first position during delivery of a radiation beam from a source, located outside the eye, to the eye.

Some embodiments further include a material that is transmissive of the radiation beam through the ocular interface. In some embodiments, the radiation beam comprises laser light. In some embodiments, the radiation beam comprises x-rays.

In some embodiments described herein, a patient ocular interface is described, for treatment of an ocular structure with a radiotherapy system, including: a holder adapted to maintain an eye in a substantially stable position; and a communication link that communicates information between the holder and a radiotherapy system, the information being indicative of a position of the eye and determining a characteristic of a radiation beam emitted from the radiotherapy system.

In some embodiments, the communication link comprises a reflective material that reflects some wavelengths of light. In some embodiments, the characteristic of the radiation beam determined by the information comprises at least one of a trajectory of the radiation beam and an emit/not-emit status. In some embodiments, the holder contacts the eye. In some embodiments, the holder is attachable to a surface external to the eye. In some embodiments, the holder is mechanically linked to the radiotherapy system. In some embodiments, the communication link to the radiotherapy system is an optical link. In some embodiments, the holder is adapted to align the radiotherapy system with an axis of the eye. In some embodiments, the holder is adapted to align the radiotherapy system with a visual axis of the eye. Some embodiments, further include a camera that visualizes a position of the eye relative to the holder. In some embodiments, the camera detects movement of the eye and communicates data relating to the eye's movement with imaging software.

In some embodiments, the holder contacts the sclera. In some embodiments, the holder contacts the cornea. In some embodiments, the holder is at least partially opaque to x-ray energy. In some embodiments, the holder is at least partially transparent to x-ray energy. In some embodiments, the holder is configured to apply a suction to the eye.

In some embodiments, a system is described, for delivery of an x-ray beam to an eye of a patient, including at least one x-ray collimator that, in use, is placed within about 15 cm of a retina; and a laser that emits a laser beam that is substantially aligned with a long axis of the collimator and that provides an indication, on at least one of a surface of the eye and a device in contact with a surface of the eye, of a direction of an x-ray beam emitted through the collimator.

In some embodiments, the system further comprising a power supply adapted to deliver between about 10 mA and about 800 mA of current to the anode of an x-ray tube that delivers the x-ray beam. In some embodiments, the anode is one of a stationary anode and a rotating anode. Some embodiments further include an eye contact member that is configured to contact the eye and maintain a position of the eye.

In some embodiments, a method is described, of radiation therapy of an eye, including, for an ocular disease having an associated dose of radiation useful therapeutically to treat that disease, providing a distance from an x-ray source located outside the eye, that is to deliver the dose of radiation via an x-ray beam, to a target of eye tissue afflicted by the disease; and based on the distance of the target from the radiation source, outputting to an output module an energy level required to achieve the dose of radiation in the x-ray beam emitted from the radiation source to the target, the target being separated from the radiation source by the distance; wherein the energy level is dependent on the distance of the target from the radiation source.

Some embodiments describe a method, for treating diseased tissue with radiation, including selecting, based on a first disease in a patient to be treated, an energy level in a radiation beam to be emitted from a radiotherapy system, the radiation beam delivering substantially an estimated dose of radiation; wherein the first disease to be treated is one of a plurality of diseases; and wherein each of the plurality of diseases requires a different energy level to achieve a therapeutic dose of radiation for that disease than the energy level required to achieve the therapeutic dose of radiation for another of the plurality of diseases; and outputting to an output module an indication of the selected energy level.

In some embodiments, the first disease affects an eye of the patient and the radiation beam is emitted toward the eye. In some embodiments, the first disease comprises macular degeneration of an eye of the patient. In some embodiments, the first disease comprises a pterygium of an eye of the patient. In some embodiments, the first disease comprises at least one of an ocular tumor, glaucoma, and premalignant lesions.

In some embodiments, described is a system, for treating diseased tissue with radiation, including a processing module that receives an input, the input comprising a selection, based on a first disease in a patient to be treated, an energy level in a radiation beam to be emitted from a radiotherapy system, the radiation beam delivering substantially an estimated dose of radiation; wherein the first disease to be treated is one of a plurality of diseases; and wherein each of the plurality of diseases requires a different energy level to achieve a therapeutic dose of radiation for that disease than the energy level required to achieve the therapeutic dose of radiation for another of the plurality of diseases; and wherein, based on the input, the processing module outputs to an output module an indication of the selected energy level.

Some embodiments describe a method, for treating diseased tissue with radiation, including selecting, based on a first disease in a patient to be treated, an energy level in a radiation beam to be emitted from a radiotherapy system, the radiation beam delivering substantially an estimated dose of radiation; wherein the first disease to be treated is one of a plurality of diseases; and wherein each of the plurality of diseases requires a different at least one of an energy level, a beam size, and a surface-to-depth ratio to achieve a therapeutic dose of radiation for that disease than the energy level required to achieve the therapeutic dose of radiation for another of the plurality of diseases; and outputting to an output module an indication of the selected energy level.

In some embodiments, a radiotherapy system is described, for treating diseased eye tissue, including a collimator that collimates a radiation beam, emitted from a radiation source, to a cross-sectional width of the radiation beam to no more than about 6 mm; wherein the collimator defines a first axis that the radiation beam follows when the radiation beam is emitted; and a light guide that emits a light beam along a second axis that is aligned with the first axis defined by the collimator, the light beam providing an indication of the first axis.

In some embodiments, the light beam comprises a laser. In some embodiments, the first axis of the collimator and the second axis of the light guide are collinear. In some embodiments, the light guide is insertable into the eye to visualize the radiotherapy target and guide delivery of the collinear x-ray beam from the radiotherapy system. In some embodiments, the system further includes a cannula, into which the light guide is insertable. In some embodiments, the cannula is configured to be fixed on a surface of an eye.

Some embodiments describe a system, for treating an eye with radiation, including a radiation source that emits radiation and a collimator that collimates the emitted radiation into a beam; an alignment system that aligns the beam with an axis traversing the eye; and a gating mechanism that reduces radiation emission from the radiation source when the beam is not aligned with the axis.

Some embodiments further include an image detection system that detects at least one of a fundus, a limbus, a cornea, and a reflection off a surface of the eye. In some embodiments, when the image detection system detects a threshold movement of the eye, the gating mechanism reduces radiation emission from the radiation source.

In some embodiments a system is described, for treating an eye with radiation, including a radiation source that emits radiation during a treatment session and that collimates the emitted radiation into a collimated beam having a cross-section dimension of less than about 6 mm; and an eye mapping module that repeatedly maps locations of structures of an eye to a coordinate system during the treatment session.

Some embodiments further comprising a radiation source mover that moves the radiation source relative to the eye to direct the emitted radiation toward an eye structure. In some embodiments, the radiation source is configured to be stationary relative to a position of the eye during the treatment session. In some embodiments, the system further includes a system shut-off that reduces or ceases emission of radiation when an eye structure is not in a path of the collimated beam. Some embodiments further include a holder to substantially hold the eye such that an eye structure is in a path of the collimated beam.

In some embodiments, a planning system is described, for delivery of radiation to an eye, including a processing module that receives an input comprising a biometric parameter of the eye; and wherein, based on the biometric parameter, the processing module outputs to an electromotive system a direction for an x-ray beam to be emitted onto the sclera of the eye. In some embodiments, the biometric parameter comprises at least one of an ocular axial length, an anterior chamber depth, a corneal thickness, and a corneal diameter.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit the scope of the disclosure. Throughout the drawings, reference numbers are reused to indicate correspondence between referenced elements.

FIGS. 1I-1J depict schematic representations of methods used to align a radiotherapy device with a lens interface.

FIGS. 2B'-2B'''' illustrate several embodiments of various collimators.

FIGS. 7A-7F illustrate representative simulations of radiation beams traveling through an eye to reach a retina of the eye and a dose profile for a target tissue.

DETAILED DESCRIPTION

Figure 1A:
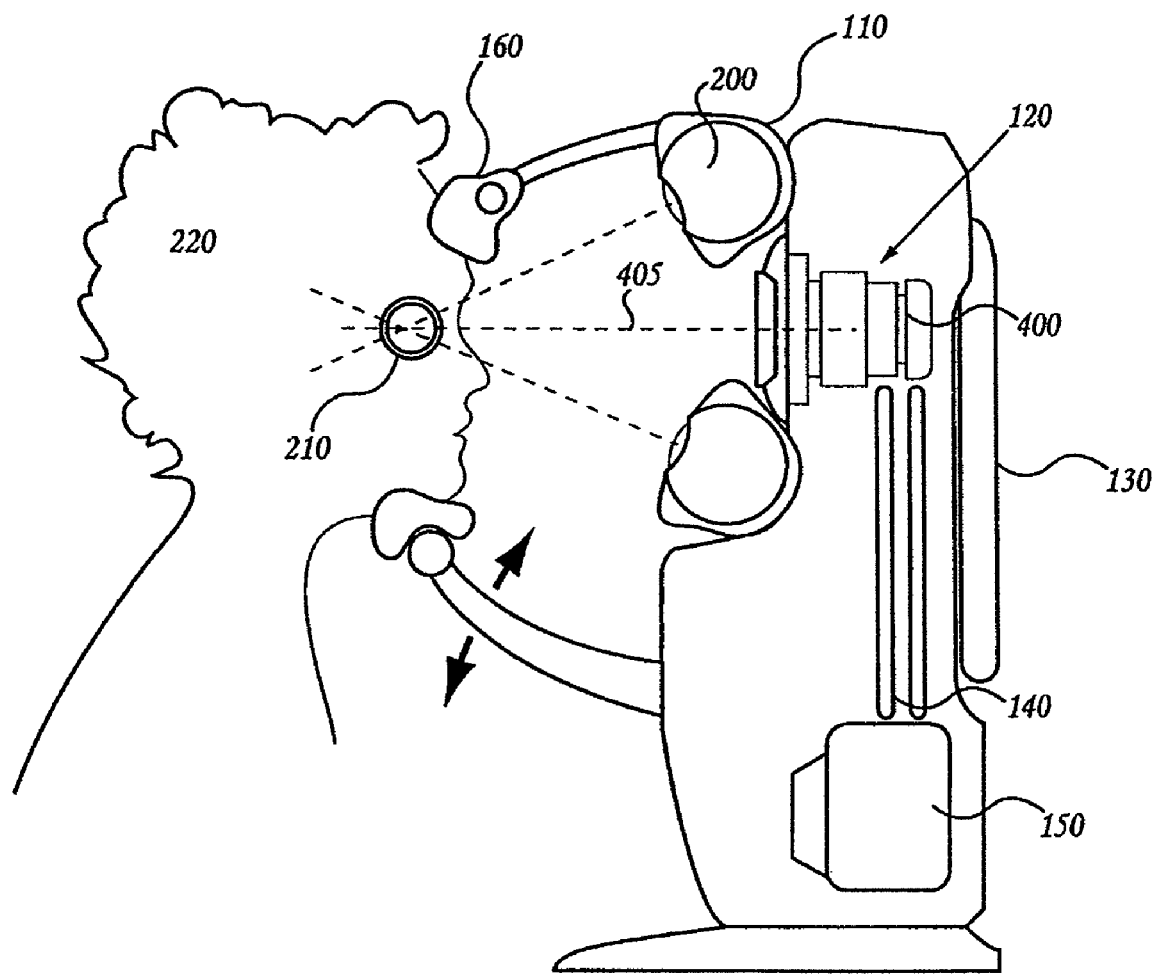
FIG. 1A illustrates a side view of embodiments of a system for treating the eye using radiotherapy.

Embodiments described herein include systems and methods for treating a human eye with radiotherapy. Some embodiments described below relate to systems and methods for treating macular degeneration of the eye using radiotherapy. For example, in some embodiments, systems and methods are described for use of radiotherapy on select portions of the retina to impede or reduce neovascularization of the retina. Some embodiments described herein also relate to systems and methods for treating glaucoma or controlling wound healing using radiotherapy. For example, embodiments of systems and methods are described for use of radiotherapy on tissue in the anterior chamber following glaucoma surgery, such as trabeculoplasty, trabeculotomy, canaloplasty, and laser iridotomy, to reduce the likelihood of post-operative complications. In other embodiments, systems and methods are described to use radiotherapy to treat drusen, inflammatory deposits in the retina that are thought to lead to vision loss in macular degeneration. Localized treatment of drusen and the surrounding inflammation may prevent the progression of dry and/or wet AMD.

In some embodiments, laser therapy is applied to drusen in combination (adjuvant therapy) with co-localized x-ray radiation to substantially the same location where the laser is incident upon the retina; the laser can create a localized heating effect which can facilitate radiation treatment, or the laser can ablate a region, or laser spot, while the radiation can prevent further scarring around the region. Such combination therapy can enhance the efficacy of each therapy individually. Similarly, adjuvant therapies can include x-ray radiotherapy in combination with one or more pharmaceuticals or other radiotherapy-enhancing drugs or chemical entities. In some embodiments, x-ray therapy is combined with invasive surgery such as a vitrectomy, cataract removal, trabeculoplasty, trabeculectomy, laser photocoagulation, and other surgeries.

Radiation, as used herein, is a broad term and is intended to have its ordinary meaning, which includes, without limitation, at least any photonic-based electromagnetic radiation which covers the range from gamma radiation to radiowaves and includes x-ray, ultraviolet, visible, infrared, microwave, and radiowave energies. Therefore, planned and directed radiotherapy can be applied to an eye with energies in any of these wavelength ranges.

Radiotherapy, as used in this disclosure, is a broad term and is intended to have its ordinary meaning, which includes, without limitation, at least any type of clinical therapy that treats a disease by delivery of energy through electromagnetic radiation. X-ray radiation generally refers to photons with wavelengths below about 10 nm down to about 0.01 nm. Gamma rays refer to electromagnetic waves with wavelengths below about 0.01 nm. Ultraviolet radiation refers to photons with wavelengths from about 10 nm to about 400 nm. Visible radiation refers to photons with wavelengths from about 400 nm to about 700 nm. Photons with wavelengths above 700 nm are generally in the infrared radiation regions. Within the x-ray regime of electromagnetic radiation, low energy x-rays can be referred to as orthovoltage. While the exact photon energies included within the definition of orthovoltage varies, for the disclosure herein, orthovoltage refers at least to x-ray photons with energies from about 20 keV to about 500 keV.

As used herein, the term "global coordinate system" refers to a physical world of a machine or room. The global coordinate system is generally a system relating a machine, such as a computer or other operating device, to the physical world or room that is used by the machine. The global coordinate system can be used, for example, to move a machine, components of a machine, or other things from a first position to a second position. The global coordinate system can also be used, for example, to identify the location of a first item with respect to a second item. In some embodiments, the global coordinate system is based on a one-dimensional environment. In some embodiments, the global coordinate system is based on a two-dimensional environment, and in some embodiments, the global coordinate system is based on three or more dimensional environments.

Kerma, as used herein, refers to the energy released (or absorbed) per volume of air when the air is hit with an x-ray beam. The unit of measure for Kerma is Gy. Air-kerma rate is the Kerma (in Gy) absorbed in air per unit time. Similarly, "tissue kerma" rate is the radiation absorbed in tissue per unit time. Kerma is generally agnostic to the wavelength of radiation, as it incorporates all wavelengths into its joules reading.

As used herein, the term "radiation dose" is a broad term and is generally meant to include, without limitation, absorbed energy per unit mass of tissue. One example of a measure of radiation dose is the Gray, which is equal to 1 joule per kilogram, which generally also equals 100 rad. For example, as used herein in some embodiments, a radiation dose may be the amount of radiation, or absorbed energy per unit mass of tissue, that is received or delivered during a particular period of time. For example, a radiation dose may be the amount of absorbed energy per unit mass of tissue during a treatment process, session, or procedure.

As used herein, the term "trajectory" is a broad term and is generally meant to include, without limitation, a general path, orientation, angle, or direction of travel. For example, as used herein in some embodiments, the trajectory of a light beam can include the actual or planned path of the light beam. In some embodiments, the trajectory of a light beam can be determined by an orientation of a light source that emits the light beam, and the trajectory can, in some embodiments, be measured, such as by an angle, or determined as with respect to a reference, such as an axis or plane.

As used herein, the term "aligned" is a broad term and is generally meant to include, without limitation, having a fixed angular relationship between zero and 180 degrees. For example, as used herein, two light beams or x-ray beams can be aligned if they are collinear, are oriented with respect to each other at a fixed angle, or have another fixed relationship. In some embodiments, the angle between aligned light beams or x-ray beams can range from about zero degrees to about 360 degrees, and can include about 90 degrees, about 180 degrees, and about 270 degrees.

"Treatment axis," as used herein, is a broad term and is generally meant to include, without limitation, an axis of an organ in relation with the radiotherapy device. For example, in some embodiments, the axis of the organ is related, such as by an angle, to an axis of the radiotherapy device. In some embodiments, the intersection of the organ axis and the radiotherapy device is used to define the target for the radiotherapy beam.

As used herein, the term "treatment session" is a broad term, and is generally meant to include, without limitation, a single or a plurality of administrations of at least one of heat therapy, radiation therapy, or other therapeutic treatment of target tissue. For example, in some embodiments, a treatment session can include a single administration of x-ray beams to the eye. In some embodiments a treatment session can include a plurality of administrations of x-ray beams and laser radiation to the a patient's eye. In some embodiments, a treatment session is limited to, for example, a single visit by a patient to a clinic for treatment, and in some embodiments, a treatment session can extend over a plurality of visits by a patient to the clinic. In some embodiments, a treatment session can include a single procedure of administering radiotherapy, and in some embodiments, a treatment session can include a plurality of procedures following different protocols for each procedure. In some embodiments, a treatment session may be limited to about a single day, and in some embodiments, a treatment session can be about 2 days, about 3 days, about 5 days, about 1 week, about 10 days, about 2 weeks, about 3 weeks, about 1 month, about 6 weeks, about 2 months, about 3 months, about 6 months, about 1 year, or longer. As used herein, the term "treatment period" is a broad term, and is generally meant to include, without limitation, any single or plurality of administrations of radiotherapy or related therapeutic treatment of tissue, and can include a single or a plurality of treatment sessions.

As used herein, the term "orders of magnitude" is a broad term and is generally meant to include, without limitation, a class of scale or magnitude of any amount, where each class contains values of a ratio related to the class preceding it. For example, in some embodiments, the ratio relating each class may be 10. In these embodiments, one order of magnitude is a magnitude based on a multiple of 10, two orders of magnitude is based on two multiples of 10, or 100, and three orders of magnitude is based on three multiples of 10, or 1000.

In some embodiments, the radiotherapy system is configured to produce beams of radiation for radiotherapy. The beams can be collimated to produce beams of different size or cross-sectional shape. The beam shape is generally defined by the last collimator opening in the x-ray path; with two collimators in the beam path, the secondary collimator is the last collimator in the beam path and can be called the "shaping collimator." The first collimator may be called the primary collimator because it is the first decrement in x-ray power and can be the largest decrement of the collimators; the second collimator can generally set the final shape of the x-ray beam. As an example, if the last collimator opening is a square, then the beam shape is a square as well. If the last collimator opening is circular, then the beam is circular. If the last collimator has multiple holes then the beam will have multiple holes of any shape (areas of radiation and no or limited radiation) in it as it reaches the target. In some embodiments, there is one collimator which serves as the primary collimator as well as the beam shaping collimator.

The penumbra refers to the fall-off in dose outside of the area of the last collimator and the beam shape and size set by that collimator, typically measured at some distance from the last collimator. Penumbra, as used herein, is a broad term and has its ordinary meaning, which is meant to include, without limitation, the percentage of radiation outside the area of the last collimator when the x-ray beam reaches a first surface of tissue or an internal target tissue, whichever is being referenced with respect to the penumbra. For example, the penumbra can include the percentage of radiation outside the area of the last collimator when the x-ray beam reaches the surface of the eye or when the x-ray beam reaches the retina of the eye. The penumbra can incorporate divergence of the beam as well as scatter of the beam as a result of passage through air and tissue. Although not meant to be limiting, penumbra is used in some embodiments that follow as the linear distance from the primary beam size where the radiation level drops below 20% of the radiation in the primary beam size including both scatter and beam divergence. As an example, if a beam diameter determined by a collimator is 5 mm at the exit of the collimator and the diameter at the tissue target where the radiation dosage is 20% of the dose over the 5 mm beam diameter (at the tissue) is 6 mm, then the penumbra is 0.5/3.0 mm (radius) or 16%.

Ideally, the size of the beam incident upon target tissue is the same size as the last collimator to which the x-ray beam is exposed; that is, the penumbra is ideally zero. In reality, a penumbra of zero is difficult to achieve when the collimator is any distance from the target because of beam divergence. However, the penumbra can be optimized, for example, by the shape of the collimator, the material of the collimator, the processing of the collimator material, the position of the anode of the x-ray tube, the position of the collimator relative to the anode of the x-ray tube and the tissue target, and the relative sizing of the collimator with respect to the x-ray source. In some embodiments of the systems and methods provided herein, the penumbra percentage at the entry point to the tissue (e.g., the eye) is less than about 10%. In some embodiments, the penumbra percentage at the entry point is less than about 5%, and in some embodiments, the penumbra percentage at the entry point is less than about 1%.

The penumbra can also refer to the percentage of radiation outside the zone of the shaping collimator at a target region. For example, in applications to the eye, the penumbra can refer to the percentage of radiation outside the zone of the shaping collimator at the macula defined above. In some embodiments, the penumbra at the macula is less than about 40%; in some embodiments, the penumbra at the macula is less than about 20%; in some embodiments, the penumbra at the macula is less than about 10%; and in some embodiments, the penumbra at the macular is less than about 5%. The penumbra can be a factor or parameter that is incorporated into a treatment plan; for example, predictive knowledge of the penumbra can be utilized to plan the treatment. In one example, a finely collimated beam (e.g., having a 4-mm diameter at the exit of the last collimator) is applied to the sclera. The beam at the retina can be 5 mm (25% penumbra) or 6 mm (50% penumbra) diameter, which can be sufficient for coverage of a lesion. With this method, the structures of the anterior eye are minimally irradiated while the lesion at the retina is fully covered. In this embodiment, divergence of the x-ray beam is utilized for minimizing the size of exposed tissue in the front of the eye without sacrificing a therapeutic dose to the retina.

A related definition is that of "isodose fall-off" which refers to the dose fall-off; it is a dose map of the area of interest. The isodose fall-off can be measured in Gy/mm, in which mm represents a linear distance from a point of interest.

Divergence angle is highly predictable for photons given the geometry of the source and can be calculated independently of scatter and the other physics which are factored into and contemplated by Monte Carlo simulations. In most instances, the x-ray source is not an idealized point source and has a finite volume. This non-idealized case enters into consideration in the design of the collimators in the beam path, as the collimators may be designed differently for a non-idealized x-ray source than for an idealized point source. For example, the x-ray source may have a source which is a square or a rectangle or an ellipse. The greatest diameter of the source may be about 0.5 mm, about 1.0 mm, about 2.0 mm, about 3.0 mm, about 4.0 mm, or about 5.0 mm. In some embodiments, the greatest diameter of the source may further be adjustable depending on the structure being treated.

Photons with shorter wavelengths correspond to radiation with higher energies. The higher-energy range of x-rays is generally in the MeV range and is generally referred to gamma x-rays, independent of how the radiation was generated. X-ray photons with relatively shorter wavelengths are referred to as orthovoltage x-rays. Higher energy radiation with shorter wavelengths corresponds to deeper penetration into target tissue, which is the reason that most applications using MeV energies require extensive shielding of the patient and surroundings. In some embodiments of this disclosure, x-rays typically used for diagnostic purposes, or low energy orthovoltage x-ray sources, can be used for therapy of ocular diseases and/or disorders which are relatively superficial in the patient such as breast, intra-operative radiation application, skin cancers, and other disorders such as peripheral vascular disease, implants, etc. X-rays typically used for diagnosis can be used for therapy by tightly collimating the x-ray beam into a thin beam of x-ray photons and directing the beam to the superficial region to be treated. If the disorder is deeper than several centimeters inside the body, then higher energy sources (e.g., MeV) may be preferred to enhance penetration of energy to the disorders. It is difficult to collimate MeV x-ray beams to small diameters with small penumbras because their very high speed photons cause secondary interactions with tissue including generation of secondary x-rays and other radiations. X-rays with energies lower than 500 keV and even lower than 200 keV can more appropriately be collimated to very small diameters.

"Laser" energy is also composed of photons of different energies ranging from short wavelengths, such as ultraviolet radiation, up to long wavelengths, such as infrared radiation. Laser refers more to the delivery mechanism than to the specific wavelength of radiation. Laser light is considered "coherent" in that the photons travel in phase with one another and with little divergence. Laser light is also collimated in that it travels with relatively little divergence as is proceeds in space. Light can be collimated without being coherent (in phase) and without being a laser; for example, lenses can be used to collimate non-x-ray light. X-ray light is typically collimated with the use of non-lens collimators, the penumbra defining the degree of successful collimation. Laser pointers are typically visualization tools, whereas larger, higher-flux lasers are utilized for therapeutic applications. In some embodiments of the systems and methods described herein, optics can be used, such as lenses or mirrors, and in some embodiments, there are no intervening optical elements, although collimators may be used.

The two eye chambers are the anterior and posterior chambers. The anterior chamber includes, among other things, the lens, the conjunctiva, the cornea, the sclera, the trabecular apparatus, the ciliary bodies, muscles, and processes, and the iris. The posterior chamber includes, among other things, the vitreous humor, the retina, and the optic nerve.

"Ocular diseases," as used in this disclosure, is a broad term and is intended to have its ordinary meaning, which includes, without limitation, at least diseases of the anterior eye (e.g., glaucoma, presbyopia, cataracts, dry eye, conjunctivitis) as well as diseases of the posterior eye (e.g., retinopathies, age related macular degeneration, diabetic macular degeneration, and choroidal melanoma).

Drusen are hyaline deposits in Bruch's membrane beneath the retina. The deposits are caused by, or are at least markers of inflammatory processes. They are present in a large percentage of patients over the age of 70. Although causality is not known, drusen are associated with markers of the location where inflammation is occurring and where neovascularization has a high likelihood of occurring in the future; these are regions of so called "vulnerable retina." Therefore, applying inflammation-reducing radiation to the region may be beneficial to the patient, as described herein.

Radiation therapy has historically been marginally successful in treating disorders of the eye; for example, in a recent Cochrane meta-analysis review (Signanavanel et. al. Radiotherapy for neovascular age-related macular degeneration, The Cochrane Database, Issue 4, 2006, the entirety of which is incorporated by reference), the authors discussed the merits of radiation therapy for AMD. Among their general conclusions were the following: ophthalmologists were reluctant to refer patients to the radiation oncologists; it was difficult to localize the radiation from the radiation source because specific methods were not used for the clinical protocol; and fractionation schemes and dosing was not standardized (this is described in further detail below and in the figures). The embodiments described in this disclosure provide for systems and methods that can be performed by the ophthalmologist, without referral to a radiation oncology clinic, that can localize the radiation source through apparatus and protocols specific to the clinical treatments, and fractionation schemes that provide standardized dosing.

Brachytherapy appears to have a highly beneficial effect at least when combined with pharmaceutical therapy as an adjuvant therapy. Brachytherapy provides the radiation dose to the region to be treated and delivers the dose at a high rate. However, brachytherapy is difficult to control as far as a treatment plan (e.g., the surgeon can hold the probe in a variety of positions for any given patient), and the brachytherapy source typically cannot be turned off (e.g., strontium has a 29 year half-life).

Radiotherapy System

The Portable Orthovoltage Radiotherapy Treatment system (PORT) 10 in FIG. 1A can be configured to deliver anywhere from about 1 Gy to about 40 Gy during a treatment period, or from about 10 Gy to about 20 Gy during a treatment period, to regions of the eye including, but not limited to, the retina, sclera, macula, optic nerve, the capsular bag of the crystalline or artificial lens, ciliary muscles, lens, cornea, canal of schlemm, choroid, and conjunctiva. In some embodiments, the system can be configured to deliver from about 15 Gy to about 25 Gy during a treatment period. In some embodiments, the system 10 is capable of delivering x-ray therapy in any fractionation scheme (e.g., about 1 Gy per day, about 5 Gy per day, about 10 Gy per month, or about 25 Gy per year), as the treatment planning system can retain in memory and recall which regions had been treated based on the unique patient anatomical and disease features. These features and previous treatments are stored in the treatment database for future reference.

The system can also deliver different photon energies depending on the degree of disease or the region of the eye being treated. For example, the x-ray generation tube can deliver photons with photon energies ranging from about 20 keV to about 40 keV, to about 60 keV, or to about 100 keV. It may be desirable to use photons with photon energies ranging from about 20 keV to about 50 keV for structures in the anterior portion of the eye because photons with these photon energies will penetrate less. It may be desirable to utilize photons with photon energies ranging from about 60 keV to about 100 keV or greater for structures in the posterior region of the eye for greater penetration to the retina. In some embodiments, the x-ray generation tube can emit photons with photon energies from about 10 keV to about 500 keV, from about 25 keV to about 100 keV, from about 25 keV to about 150 keV, from about 40 keV to about 100 keV, or any combination of ranges described above or herein. In some embodiments, selection of the photon energy can be based on diagnostic calculations, which can include a model of the eye created from anatomic data taken from the actual eye of the patient to be treated. The treating medical practitioner can choose the beam energies based on the disease and then set the machine to the desired energy level. In some embodiments, the system can receive input from the medical practitioner relating to the type of disease, and the energy level can be preset, which can also be subject to modification by the medical practitioner.

Although several embodiments herein are described with respect to ocular applications, PORT can be applied to any superficial body structure within reach of orthovoltage x-rays or to structures accessible during surgical procedures. For example, in regions such as the breast, it may be desirable to use x-rays with energies greater than about 40 keV but less than about 200 keV to reach the structures of interest. Other structures of interest include, for example, skin lesions, facial lesions, mucosal lesions of the head and neck, nails, muscles, soft tissues, anorectal regions, prostate, genital regions, joints, tendons, muscles, and the urogenital tract.

PORT can be applied to specific structures within the eye, while sparing other tissues, because PORT's imaging systems, modeling systems, and finely-tunable collimators can provide precisely directed x-ray beams that can be targeted on specific structures within the eye with small penumbras (for example, about 1 mm to about 5 mm beams with less than about 10-20% penumbra). PORT therapy is also based on individualized, biometric representations of the eye which allows a personalized treatment plan to be created for every patient.

As described above, orthovoltage generators, or other low energy x-ray generators, allow for the system to be placed in a room without requiring thick protective walls, special shielding apparatus, or special controls which would be required with devices generating x-rays with photon energies greater than about 500 keV. Orthovoltage generators, or other low energy x-ray generators, are also more compact than linear accelerators, which allow the smaller generators to be moved and directed with less energy from control motors as well as with less internal and external shielding. The lower energy x-ray generators also facilitate beam collimation and directing schemes, resulting in beams having smaller penumbras and capable of tighter collimation. In addition, in a scheme where it is desired to move the x-ray source, much less energy is used to move the source to different positions, and the entire system is scaled down in size with lower energy x-ray sources.

In some embodiments, the radiotherapy system is used to treat a wide variety of medical conditions relating to the eye. For example, the system may be used alone or in combination with other treatments to treat macular degeneration, diabetic retinopathy, inflammatory retinopathies, infectious retinopathies, tumors in, around, or near the eye, glaucoma, refractive disorders, cataracts, post-surgical inflammation of any of the structures of the eye (e.g., trabeculoplasty, trabeculectomy, intraocular lenses, glaucoma drainage tubes, corneal transplants, infections, idiopathic inflammatory disorders, etc.), ptyrigium, dry eye, and other ocular diseases or other medical conditions relating to the eye. The radiotherapy system also includes controls for maximum beam energy (e.g., ranging between about 30 keV to about 150 keV), beam angles, eye geometries, and controls to turn off the device when the patient and/or eye move out of position.

The radiotherapy treatment system includes, in some embodiments, a radiation source, a system to control and move the source to a coordinate in three-dimensional space, an imaging system, and an interface for a health care professional to input treatment parameters. Specifically, some embodiments of the radiotherapy system include a radiotherapy generation module or subsystem that includes the radiation source and the power supplies to operate the source, an electromotive control module or subsystem that operates to control power to the source as well as the directionality of the source, a coupling module that links the source and control to the structures of interest (e.g., the eye), and an imaging subsystem. In some embodiments, these modules are linked to an interface for a healthcare professional and form the underpinnings of the treatment planning system. The terms "module" and "subsystems" can be used interchangeably in this disclosure.

FIG. 1A illustrates a side view of embodiments of a system 10 for treating ocular diseases using radiotherapy. In some embodiments, as illustrated, the radiotherapy treatment system 10 comprises a radiotherapy generation module or subsystem 110, a radiotherapy control module or subsystem 120, an interface display 130, a processing module 140, a power supply 150, a head restraint 160, and an imaging module 400, which can be a camera.

In some embodiments, the radiotherapy device delivers x-rays to the eye 210 of a patient 220. The power supply 150 preferably resides inside the system 10 or adjacent the system 10 (e.g., on the floor). In some embodiments, however, the power supply 150 can reside in a different location positioned away from the system 10. The power supply 150 can be physically coupled to the x-ray generator 110 (in a monoblock configuration) or can be uncoupled from the x-ray generator (e.g., the x-ray source moves independently of the power supply and is connected through, for example, high power cables). In some embodiments, the power supply is a rechargeable, portable supply. In some embodiments, a cooling system for the x-ray tube is also provided. The cooling system can be water, oil, or air convection, and the cooling system can be attached to or located a distance from the radiotherapy system 10.

Voltage can be wall voltage of about 110V or about 220V (with assistance of a transformer) which can be used for the devices, subsystems, or modules of the system. Currents supplied to the system to generate x-rays may be on the order of about 1 amp or lower down to about 50 mA or even about 5 mA to about 10 mA. In some embodiments, the power supply can deliver currents up to hundreds of milliamps (e.g., about 600 mA). For example, currents ranging from about 100 mA to about 1 amp, or greater, can be used when protocols or features of the system are configured to accommodate these higher current, such as, for example, when the x-ray source is a rotating anode source.

In some embodiments, what is desired of the power supply is that a high voltage be generated to drive the electrons from the cathode in the x-ray tube to the anode of the x-ray; electron movement is performed within a vacuum inside the x-ray tube. The high voltage (e.g., about 30,000 to about 300,000 volts or higher) may be desired to accelerate the electrons inside the vacuum. A second current is typically used with x-ray power supplies in order to generate the electrons from a filament, the electrons are subsequently accelerated through the voltage potential. Therefore, x-ray power supplies typically have two power supplies in order to generate x-rays. Once generated, the electrons speed toward the anode under the influence of the high voltage potential; the anode is where the x-ray generating material typically rests (e.g., tungsten, molybdenum).

The anode is considered the radiation source, and its size and structure has a role in penumbra determinations. For example, a point source may be approximated by a anode with a largest diameter of equal to or less than about 1 mm; points sources can deliver the highest quality beam with the tightest penumbra. Less optimal are sources with anodes greater than about 1 mm; for example, 2-mm, 3-mm, 4-mm, or 5-mm sources can also be used in connection with the embodiments described herein. However, the penumbra is typically larger than it would be with sources having these larger dimensions than for a source having a cross-section dimension that is equal to or less than about 1 mm. The anode is also a major determinant of the x-ray flux. The heat generated by the anode is the major limiting factor in the ultimate flux which can be achieved by the x-ray source. To the extent the anode can be cooled, the x-ray flux can be increased accordingly. This is part of the trade-off in penumbra; larger anodes can tolerate larger currents due to their larger thermal mass. X-ray output is related to current so higher current for a lower temperature allows a greater x-ray flux. In some embodiments, rotating anode sources are used so that the anode is "cooled" by virtue of the anode being moved to different points with time.

Once the electrons strike the x-ray generating material, x-rays are generated. An absorbing metal (e.g., aluminum, lead, or tungsten) within the casing of the system will absorb much of the generated x-rays which have been scattered from the source 110. The x-rays, which are pre-planned to escape, are emitted from the source and travel into a collimator (e.g., a primary or secondary collimator) and optionally through a filter (e.g., an aluminum filter). The collimator is intended to direct the x-rays toward the patient 220. Notably, as described herein, collimators can be designed and manufactured so as to minimize penumbra formation and scatter and to optimize the shape and/or direction of the x-ray beam. The power supply is preferably connected to the x-ray source by a high-power cable that can be highly insulated to reduce power leakage.

Figure 2A:
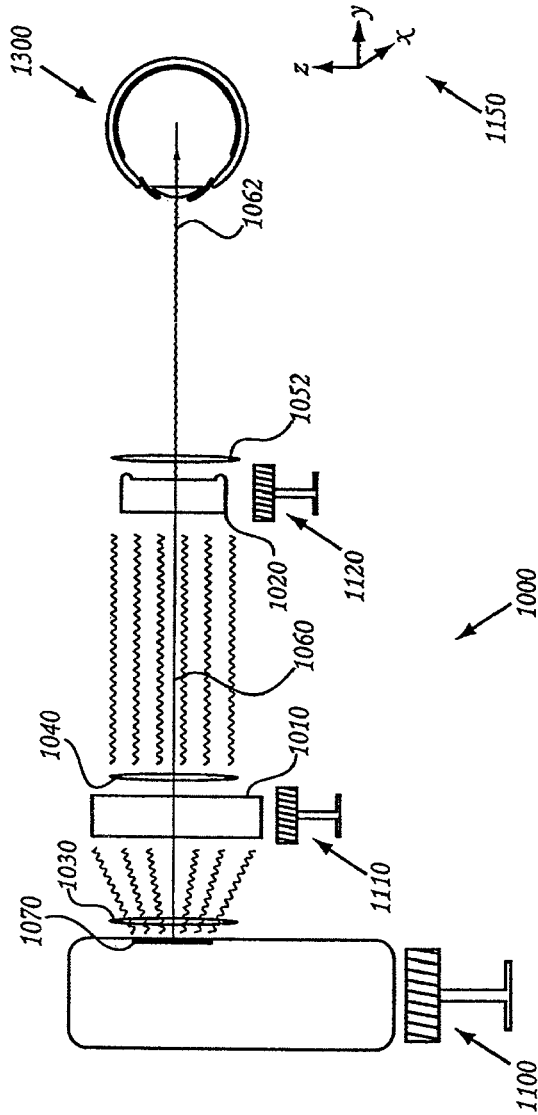
FIG. 2A illustrates a side schematic view of embodiments of a radiotherapy system illustrating some system components of FIGS. 1A-1B.
Figure 2A:
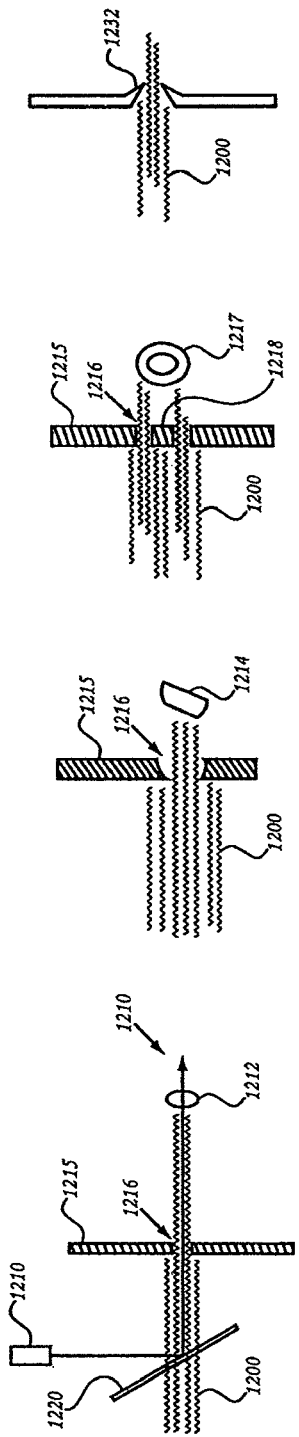

The collimator can be one or more collimators (e.g., as illustrated in FIG. 2A, a primary collimator 1030 and a secondary collimator 1040, and even a third collimator 1052). In some embodiments, a secondary (shaping) collimator is placed close to the eye 1300 (e.g., within 10 cm) of the patient, and the primary collimator 1030 is placed close to the source 1070. This type of configuration can decrease the penumbra generated by the source 1070 on the ocular structures of the eye 1300. The source can include filtration or the collimator can include filtration.

In some embodiments, collimators are specialized apertures. The apertures can be adjustable; for example, the aperture can be adjustable from about 1.0 cm to about 0.5 mm or below 0.5 cm to about 0.01 cm. In some embodiments, the aperture is adjustable (e.g., automatically or manually by the operator of the machine) between about 0.5 mm and about 7.0 mm. In some embodiments, the collimator is constructed from tungsten, lead, aluminum, or another heavy metal. In some embodiments, the collimator has a cylindrical shape for the radiation to pass through; in some embodiments, the collimator has a coned shape for the radiation to pass through. In some embodiments, the collimator aperture has a rounded shape. In certain embodiments, the collimator has a curvilinear shape for the x-ray to pass through. The collimator can be shaped to accommodate the distribution of radiation desired at the target; for example, in some embodiments, it is desirable to avoid the optic nerve while focusing radiation on the macular region. To avoid the optic nerve, it may be desirable for the radiation to be directed through a crescent shaped collimator or another weighted distribution such that the optic nerve side (nasal side) of the macula receives less dose than the temporal side of the macula.

In some embodiments, the collimator is cut using wire-EDM; in other embodiments, the collimator path is cut and polished using a laser. In some embodiments, the collimator has smooth contoured, cut and polished edges that reduces scattering as the radiation passes through the collimation apparatus. In some embodiments, the collimator has a region of thinner metal than another region so that the beam is relatively modified but does not have a sharp contour. In other embodiments, the collimator is not a complete aperture but is a thinning of the material at the region where a greater amount of x-ray energy is desired. For example, a thickness of the filter material may vary depending on the shape or desired filtering properties of the filter material. In some embodiments, reducing a thickness of the filter material by half allows radiation beams to pass through the portion of the reduced thickness of the filter material, but the radiation beams are still substantially blocked from passing through the portions of the filter material that do not have a reduced thickness. In some embodiments, the thickness of the filter remains constant throughout, but materials having different radiopacity are used. For example, a material having a higher radiopacity is used to filter the x-ray emission, and a material having a lower radiopacity is used, for example, in the place of the aperture to permit passage of the x-rays.

In some embodiments (e.g., FIG. 2C), a light pointer 1410 (e.g., a laser beam emitted from a source 1450) is coupled to a collimator 1405, or behind the collimator 1405, so that the light pointer 1410 is coincident with an x-ray beam 1400; the light pointer 1410 can indicate the position on a surface of an eye 1300 through which the radiation source enters by tracking angles of incidence 1420, 1430 of the collimator and x-ray beam. The collimator 1405 is preferably collinear with the light source 1450, which can act as a pointer to indicate the point on the eye through which the radiation enters the eye 1300. In some embodiments, the light pointer position is used to track the radiotherapy source vis-à-vis an image recognition system which identifies the position of the pointer relative to an ocular structure (e.g., the limbus) and the radiotherapy device is then moved based on the image (e.g., to a region further away from or closer to the limbus of the eye). In some embodiments, the physician visualizes the position of the laser pointer relative to the limbus and manually adjusts the x-ray source into position.

In some embodiments, a laser pointer 1210, illustrated in FIG. 2B', sits on top of, or is coincident with the x-ray beam through the primary or secondary collimator 1215. The laser pointer 1210 can be reflected off a reflector 1220 that aligns the laser pointer 1210 with the collimator opening 1216 such that the laser point 1210 strikes substantially the same position of a surface beyond the collimator opening as does the x-ray 1200. In some embodiments, the laser pointer 1210 is aligned with the collimator opening 1216 such that the laser point 1210 has substantially the same trajectory as does the x-ray beam 1200 that passes through the collimator opening 1216. In any case, the direction of the laser pointer 1210 and the x-ray beam 1200 are coupled to one another so that knowledge of the position of either is equivalent to knowledge of the position of the other beam.

The reflector 1220 can be a beam splitter, and the beam splitter can be transparent to x-ray energy 1200 or even act as a filter to create the desired spectrum of x-ray energy. The laser pointer 1210 can emit a wavelength that is detectable by the system camera 1460 (illustrated in FIG. 2C). Because the pointer 1210 is seen on the camera, the pointer 1210 indicates where the radiation beam enters the eye. The pointer 1410 can also serve as a visual verification that the x-ray source is powered on and directed in the proper orientation with respect to the ocular structure, or target tissue 1480, of interest. With a second camera in the system, the angle of incidence of the laser pointer, and by definition, the x-ray beam can be determined.

At least one imaging module 400, 1460, such as a camera, is included in the system to at least track the eye in real time. In some embodiments, the imaging module 400, 1460, or camera, images the eye with or without the x-ray source tracking device (e.g., laser pointer 1210) described above. The camera can detect the position of the eye and relate the direction of the x-ray and collimator system to the position of the eye. An optional display 130 directed to the operator of the radiotherapy system on the system 10 can depict the position of the x-ray device in real time in some embodiments.

In some embodiments (FIG. 4), the camera 2055 detects the position of the eye, and digitizing software is used to track the position of the eye. The eye is meant to remain within a preset position 2060, or treatment field, which can correspond to the edges of the limbus; when the eye deviates from the position 2054 beyond a movement threshold, a signal 2090 can be sent to the radiation source 2000. As used herein, the term "movement threshold" is a broad term and is intended to have its ordinary meaning, which includes, without limitation, a degree or measurement that the eye is able to move and remain within the parameters of treatment without shutting the radiation source 2000 off. In some embodiments, the movement threshold can be measured in radians, degrees, millimeters, inches, etc. The radiation source 2000 is turned off when the eye is out of position 2057 beyond the movement threshold, and the radiation source is turned on when the eye is in position 2054, or within the movement threshold. In some methods of setting the movement threshold, a treating professional delimits the edges of the limbus 2060 and the treatment planning software then registers the edges of the limbus 2060. If the limbus of the eye moves away 2030 from the delimited edge limit, a signal 2090 is sent to the radiation device to shut down.

Figure 1B:
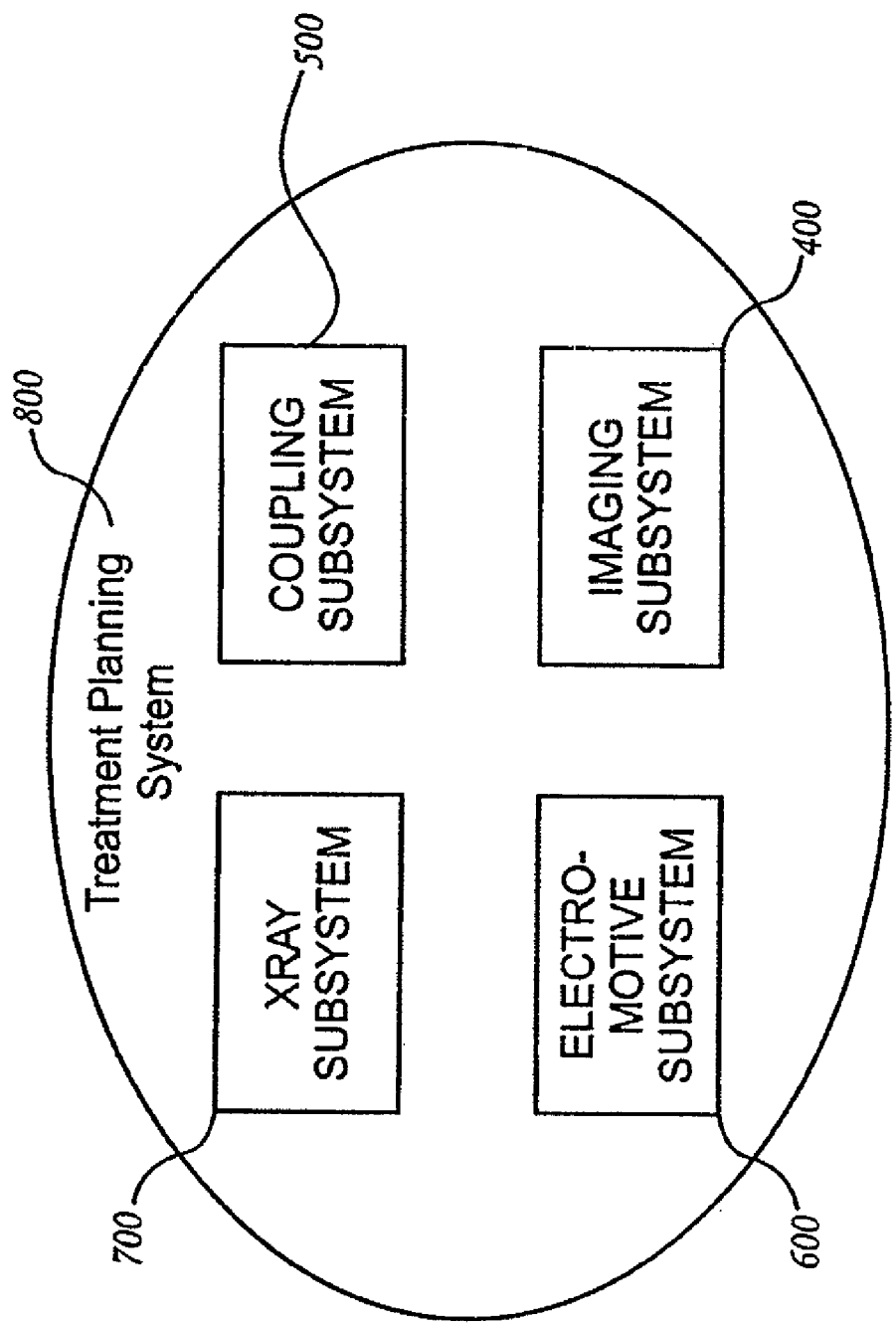
FIG. 1B is a schematic format of embodiments of a radiotherapy treatment system.
Figure 1C:
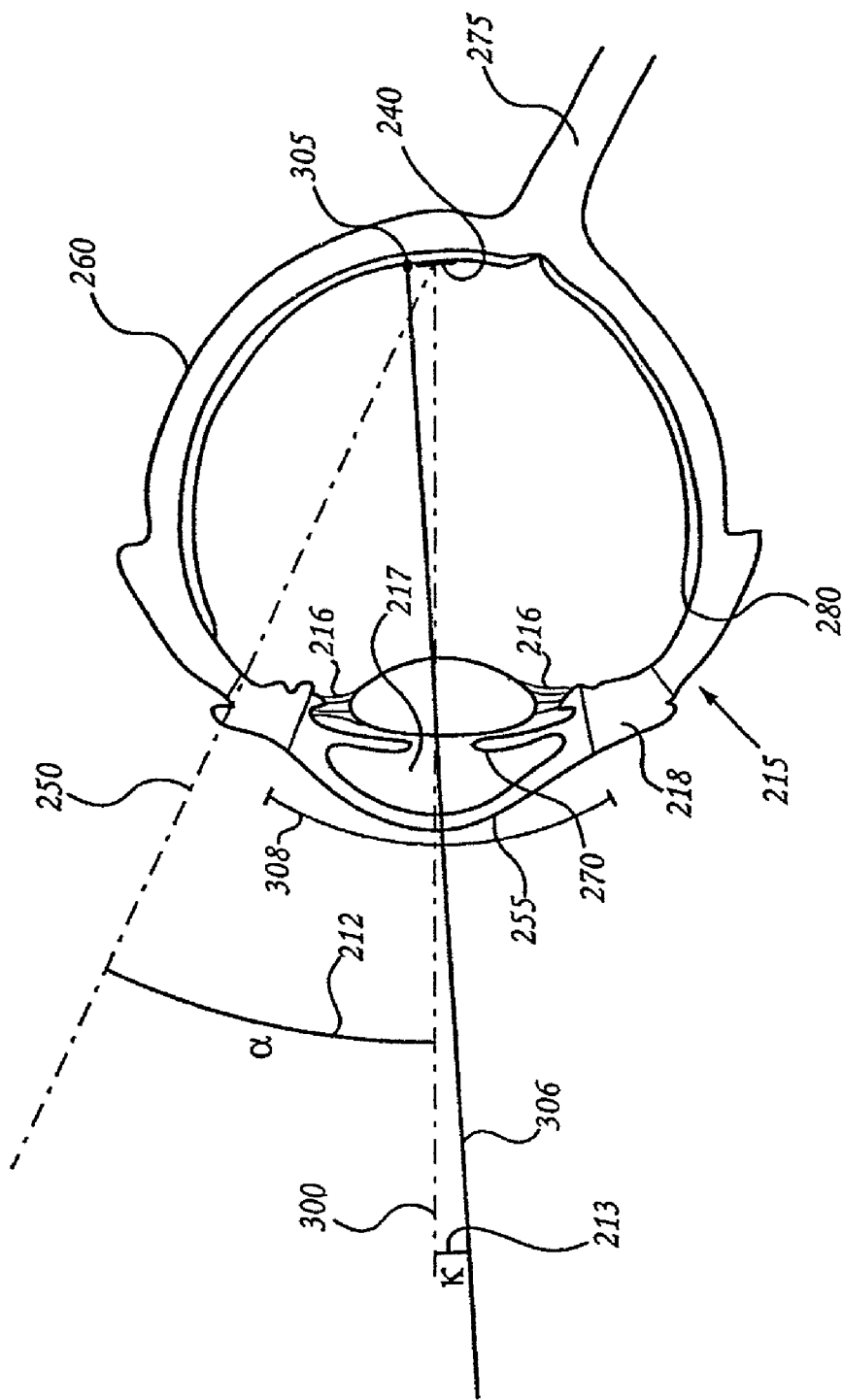
FIG. 1C is a schematic of the eye.
Figure 1D:
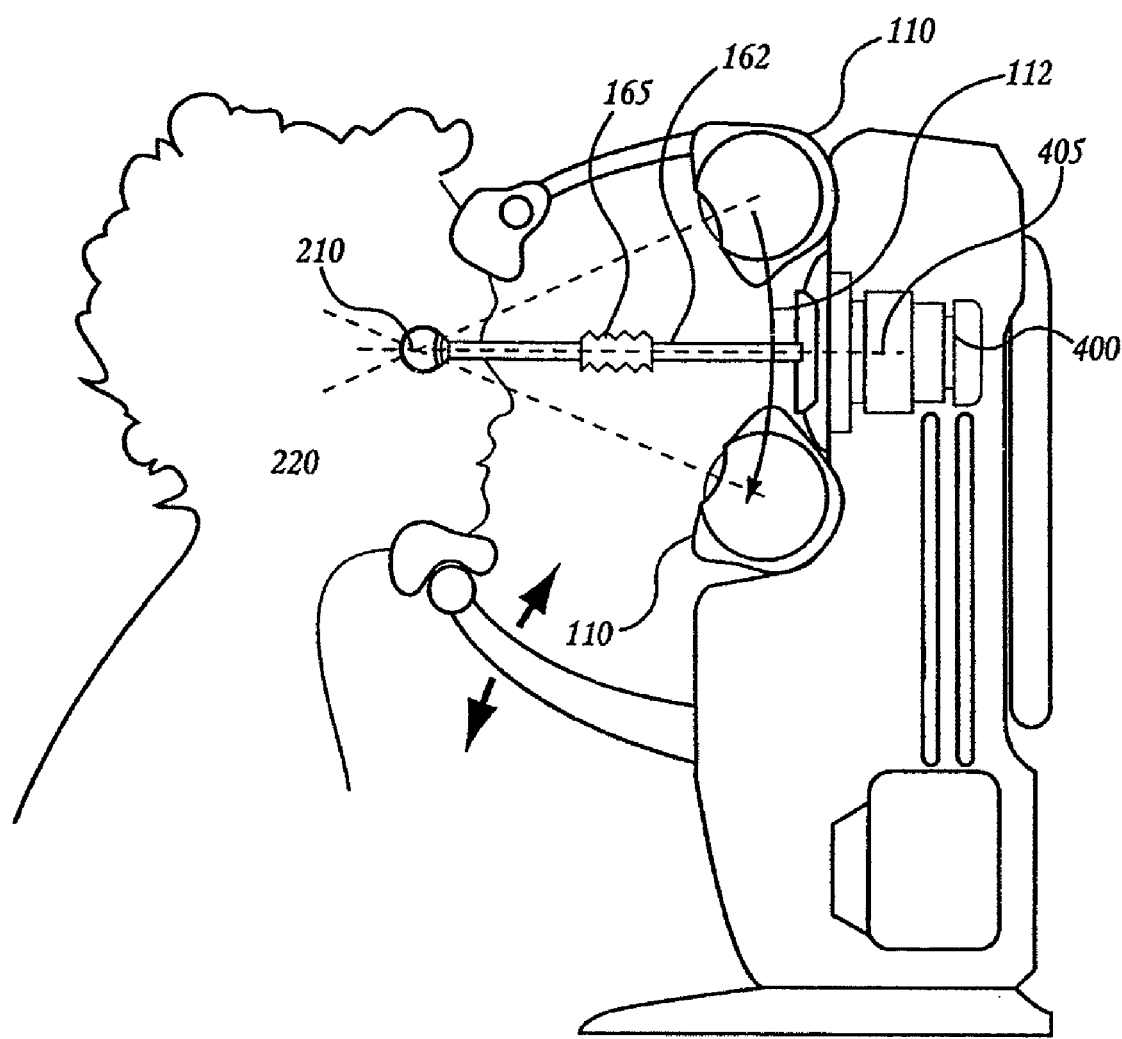
FIGS. 1D and 1E depict embodiments of a radiotherapy system which communicates with a lens on the eye.
Figure 1E:
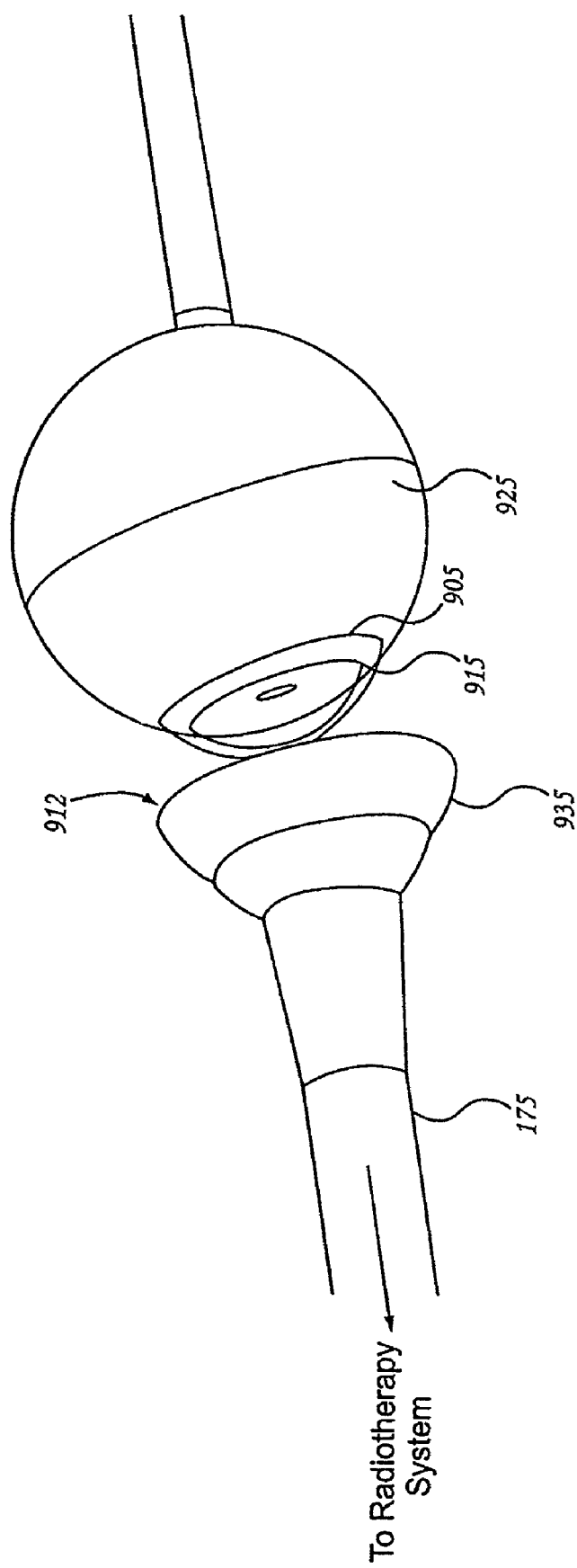

In some embodiments, a connection, or coupling, 162 extends from the system and contacts the eye 210 (FIGS. 1D and 1E). The connection can be a physical connection which can include an optical or other communication between the system and the eye in addition to a mechanical connection. The physical connection 162 can serve several functions. For example, in some embodiments, the connection 162 is a mechanical extension which allows the position of the eye to be determined because it is directly applied to the cornea or sclera. It also provides for inhibition of the eye so that the patient is more inclined to be compliant with keeping their eye in one position throughout the treatment. In addition, the eye can be moved into a pre-determined position, in the case, for example, when the patient's eye has been paralyzed to perform the procedure. Finally, the physical contact with the eye can be used to protect the corneal region using an ophthalmic lubricant underneath the physical contact device. The physical connection 162 from the cornea allows for positioning of the eye with respect to the system.

The physical connection 162 to the eye from the radiotherapy system 10 can contact the limbus 905 in FIG. 1E (also see 308 in FIG. 1C) around the eye or can contact the cornea 915 or the sclera 925. The physical connection can contain a suction type device 912 which applies some friction to the eye in order to move the eye or hold the eye in place with some force. In certain embodiments, the connection 162 contacts the sclera when suction is applied. The physical connection 162 can dock onto a scleral lens 935 or a corneal lens which is inserted separately into the eye. Any of the materials of the physical connection can be transparent to x-rays or can absorb some degree of x-ray.

The physical connection 162 can help to stabilize the eye of the patient, reducing eye movement underneath the lens. If a lubricant is inserted inside the lens, the lens can hold a gel or lubricant to protect the eye during the procedure. The lens can also contain through holes which can provide the cornea with oxygen.

The physical connection 162 can be movable with respect to the remainder of the radiotherapy system; the physical connection 162 can be rigid, substantially rigid, or can contain a spring 165, which allows flexibility in the axial or torsional direction. In some embodiments, the connection 162 is not mechanical at all but is an optical or other non-contact method of communicating between a radiotherapy system and a lens 935 positioned on the eye. The physical connection 162 can signify the coordinate reference frame for the radiotherapy system and/or can signal the movement of the device with respect to the eye. Connection 162 can therefore assist in maintaining eye location in addition to maintaining eye position by inhibiting movement of the patient. Physical connection 162 can contain radiotransmitters, a laser pointer, or features which can be captured on a camera so that the eye can be located in three-dimensional space.

In some embodiments, the physical connection 162 to the eye is docked into position on the eye by the physician so that it identifies the center of the limbus and the treatment axis through its center. The position of the eye can then be identified and tracked by the radiotherapy system. With knowledge of the center of the limbus in combination with the eye model, the radiotherapy system can then be directed about the treatment axis and center of the limbus to deliver radiation to the retina.

Figure 1F:
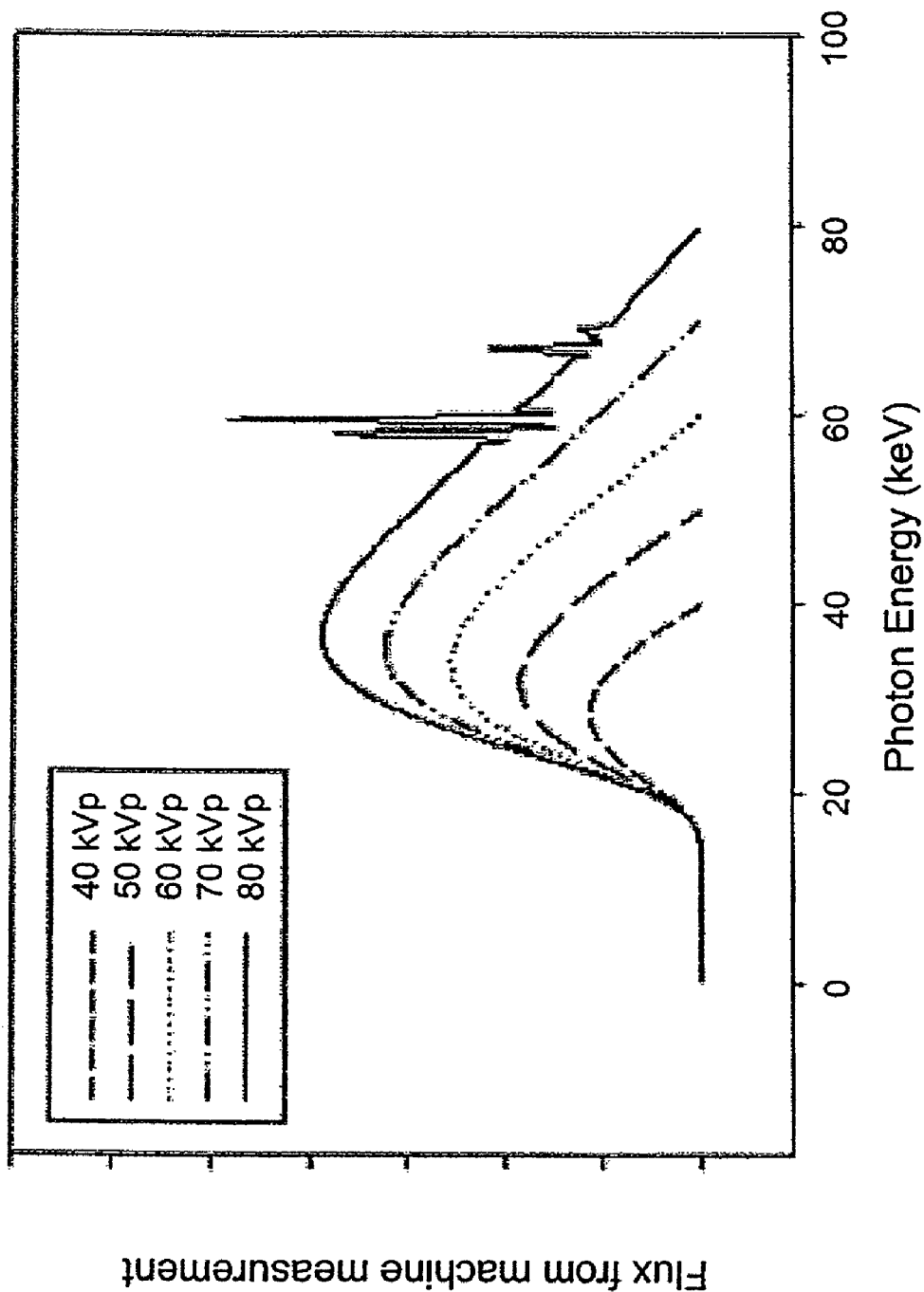
FIG. 1F depicts an x-ray radiation spectrum.
Figure 1G:
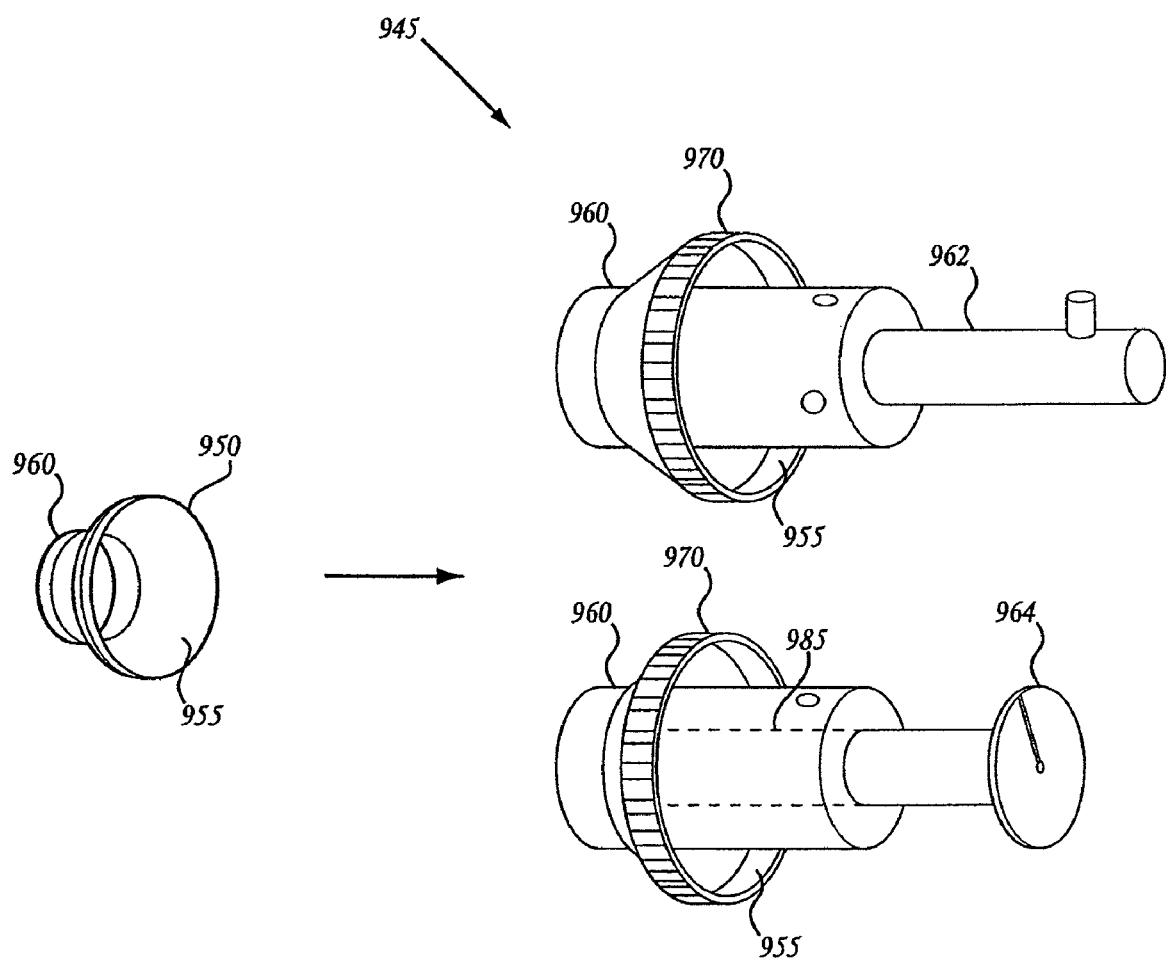
FIG. 1G depicts an interface between the eye and the radiotherapy device.

In some embodiments, the physical connection 162 can include a radiotherapy coupling device 945 (FIG. 1G). The coupling device 945 has an ocular surface 960, which can include, for example, a scleral lens and a radiotherapy coupling surface 950. The ocular surface 960 can cover the cornea and contact the cornea or it can cover the cornea, only contacting the sclera. In some embodiments, the ocular surface 960 can cover and contact both the cornea and the sclera. The ocular surface 960 can be a lens in some embodiments, and in some embodiments, the surface 960 can be a substantially transparent window with little or no refraction. The ocular surface 960 can be used to retain ocular gel or it can be a shell with a hole in the center. The ocular surface 960 can be customized for an individual patient using imaging modalities, such as for example, an IOL master, optical coherence tomography (OCT), corneal surface mapping, MRI, CT scan, and ultrasound. The ocular surface 960 can be flexible or rigid or a composite. Flange 970 can function to hold the eyelids apart or can serve as a fiducial for the radiotherapy device.

Opposite the ocular surface 960 are radiotherapy coupling surfaces, or portions, 950, 955. These surfaces, individually or collectively, couple the coupling device 945 with the radiotherapy system. While the ocular surface 960 interfaces with the eye and structures, the radiotherapy portion 950, 955 couples the ocular surface to the radiotherapy system. The radiotherapy portion, 950, 955 can link the coupling device 945 to the radiotherapy system in a variety of ways. For example, the radiotherapy portion 950, 955 can couple to the radiotherapy device via laser pointer, via infrared coupling, via microwave coupling, via mechanical coupling, via reflection, or via radiofrequency transmitters.

An additional element of the coupling device 945 can be fiducial markers 970 which can define geometry of the device or geometric relationships between the device 945 and the radiotherapy system. An additional component of the radiotherapy coupling device 945 in some embodiments is a lumen 985 which traverses the device and, in some embodiments, extends to the surface of the eye. The lumen 985 can be used to pass probes 962 such as may be used to determine the axial length of the eye (e.g., an A-scan). In some embodiments, the probe 962 can include a laser pointer probe 962, which can point outward away from the eye of the patient. The outward pointing laser pointer can be used to determine alignment of the device, and therefore the eye, relative to the radiotherapy system. In some embodiments, the laser pointer is used to align the radiotherapy device with an axis of the eye and can be used to turn the radiotherapy on (when in position) or off (when not in position). In these embodiments, the patient turns the device on and off, and the radiotherapy system operates when the eye is aligned with the machine and turns off when the device is not aligned with the radiotherapy device.

In some embodiments, the probe 962 contains a mirror 964. The mirror 964 can function as a beam reflector to indicate alignment or misalignment of the radiotherapy device. For example, the mirror 964 will reflect a light such as a laser pointer or an LED. The light originates on the radiotherapy device and its reflection from the mirror 964 on the coupling device 945 is indicative of the direction of the mirror relative to the radiotherapy device. The mirror can be parallel to the surface of the cornea, and therefore, a beam perpendicular to the mirror is approximately perpendicular to the cornea. A perpendicular beam to the cornea will travel through the optical or geometric axis of the eye and reach the center of the posterior pole of the eye (also shown and described in FIGS. 1I and 1J).

In some embodiments, the mirror is a so-called "hot mirror" or a "cold mirror" in which the mirror reflects some wavelengths and transmits others. For example, a "hot mirror" can reflect an infrared laser pointer and transmit visible light so that the patient or treating physician or a camera will be able to see through the lens. A "cold mirror" will transmit infrared and reflect visible so that a visible laser pointer can be reflected while infrared can be transmitted; cold mirrors can be used, for example, in cases where it is desired to utilize an infrared fundus camera during treatment.

Figure 1H:
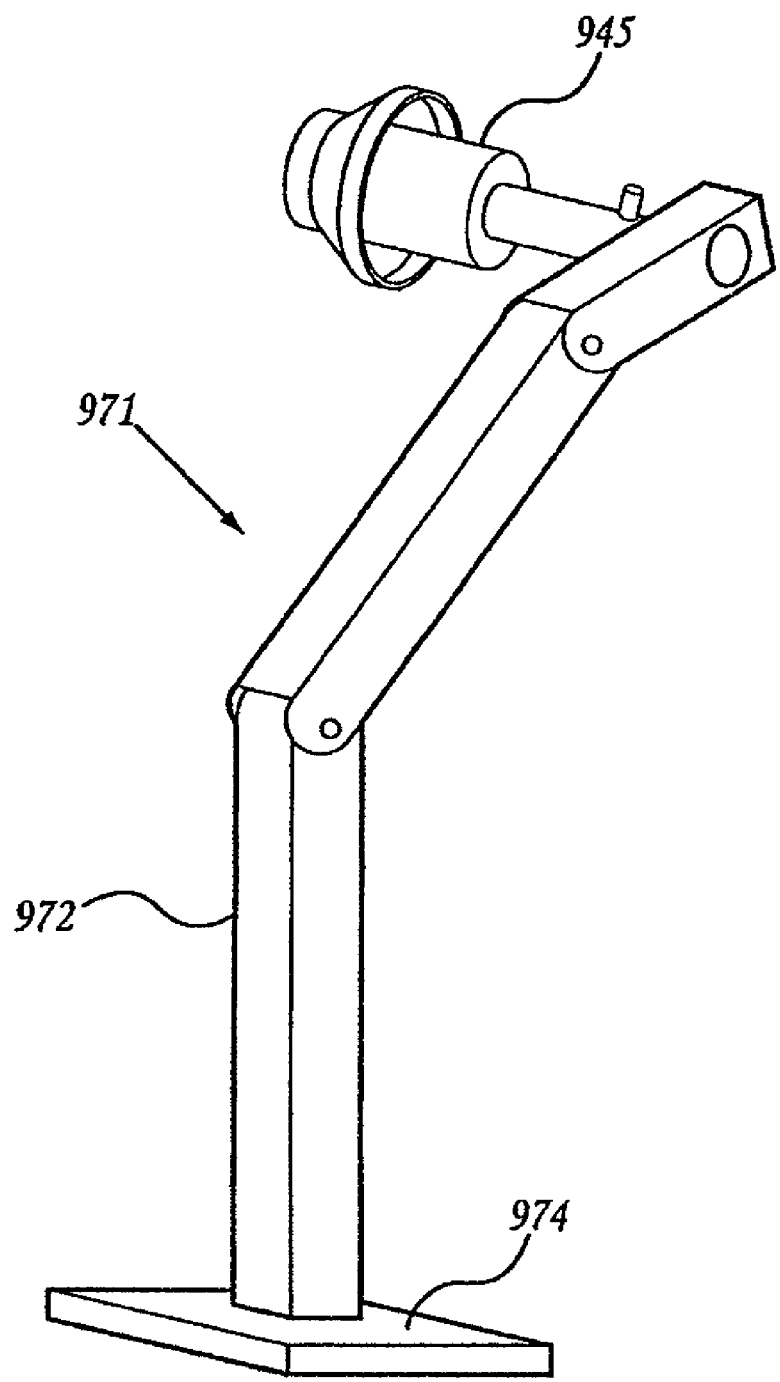
FIG. 1H depicts a mountable holder for the interface.

In some embodiments, the coupling surfaces 950, 955 of the device 945 can be attached to a holder 971 (FIG. 1H) to hold the eye in place. The holder 971 can be attached to the radiotherapy device, but preferably it is attached at a location separate from the radiotherapy device, such as a frame that is attached to the table or platform 974 which holds the radiation device. In some embodiments, the frame 972 has multiple joints, and in some embodiments, the frame 972 is flexible or springy like a cantilever beam. The frame 972 provides for some force against the eye of a patient transmitted through the coupling device 945 when it is attached to the holder 971.

In some embodiments, the coupling device 945 can include material that is radiotranslucent, or that permits at least some radiation to pass. In some embodiments, the radiotranslucent material of the coupling device 945 can be configured to permit the passage of the therapeutic x-ray beams during treatment. For example, the coupling device 945 can engage the eye to maintain position of the eye, and the x-ray beams can be directed to target eye tissue with a trajectory that passes through at least a portion of the coupling device 945. Accordingly, the treatment planning system can plan x-ray beam trajectories without significant consideration of where the coupling device 945 engages or is positioned on the eye.

In some embodiments, the coupling device 945 can include material that is radiopaque, or that reduces or limits the transmission of radiation. In some embodiments, the radiopaque material of the coupling device 945 can be configured to limit transmission through the material of radiation, such as, for example, x-ray beams. For example, the coupling device 945 can engage the eye to maintain position of the eye, and x-ray beams that are directed to target tissue of the eye will not be permitted to pass through, or transmission of the x-ray beams through the material will be substantially limited, the coupling device 945. In these embodiments, the coupling device 945 can be used as a shield for critical structures of the eye (e.g., the lens, the optic nerve, the cornea, as so forth) by limiting radiation exposure to these structures.

The treatment planning system can be configured to identify or recognize the radiopaque material and limit application of x-ray beams having trajectories toward the target tissue that may cross the coupling device 945. For example, when the coupling device 945 engages the eye, a zone is created outside the eye where application of x-ray beams to the target tissue will pass through the coupling device 945. When the coupling device 945 is substantially round, this zone in space will project from the target tissue through the coupling device 945 in the form of a cone, in which if the source of the x-ray beam is placed, the trajectory of the x-ray beam will pass through the coupling device 945 to the target tissue.

An axis extending from the target tissue and passing through the coupling device 945 will represent a beam trajectory that will be required to pass through the coupling device 945 to treat the target tissue. If the coupling device 945 includes radiopaque material, the trajectory that passes through the coupling device 945 may not be an optimal approach, as the material may hinder or otherwise affect the x-ray beams. Accordingly, in some embodiments, the source is relocated outside the space that corresponds to trajectories that pass through the coupling device 945 to treat the target tissues, and a new trajectory can be established that does not pass through the coupling device 945. This new trajectory will be transverse, or not parallel to, the axis that passes through the coupling device. In some embodiments, the new trajectory can be parallel to the axis that passes through the coupling device, but not collinear with the axis and not directed to the same target site as that of the axis. Similar new trajectories can then be replicated with similar relationships to the axis.

In some embodiments, the coupling device 945 can include both material that is radiopaque and material that is radiotranslucent. In some embodiments, the radiopaque material of the coupling device 945 can be configured to limit transmission through the material of radiation, such as, for example, x-ray beams, and the radiotranslucent material can be configured to permit transmission of radiation (e.g., x-ray beams) to pass through the material. The coupling device 945 can further be configured to provide alignment trajectories along which the x-ray beams will pass to the target tissue. In some embodiments, the coupling device 945 can further operate as a tertiary collimator by limiting the beam size or shape. For example, the radiotranslucent material of the coupling device 945 can be sized and shaped as the aperture through the secondary collimator. In such embodiments, when the x-ray beam is emitted through the radiotranslucent material, any penumbra at the coupling device 945 can be blocked by the surrounding radiopaque material. In some embodiments, apertures in the radiopaque material may be provided instead of radiotranslucent materials. Accordingly, the coupling device 945 can further provide shielding or targeting functions.

Some embodiments provide that the coupling device 945 have a plurality of apertures or portions of radiotranslucent material positioned radially around a center of the coupling device 945. The apertures can be shaped as circles, squares, rectangles, ovals, curvilinear, irregular, annular, concentric rings, and so forth. In some embodiments, the coupling device 945 is configured to include an aperture or portion of radiotranslucent material only in a center portion of the device to permit transmission of radiation therethrough to target tissue.

In some embodiments, the coupling device 945 can have a radiopaque material that comprises substantially a central portion of the coupling device 945 (e.g., a portion of the ocular surface 960), and a portion of the coupling device 945 extending around a periphery, or the edges, of the central portion comprises radiotranslucent material. Accordingly, the central portion can operate as a shield to structures of the eye, and the x-ray beams can pass through the radiotranslucent material during radiotherapy. Thus, the coupling device 945 can have a larger ocular surface 960 to engage the eye while still permitting x-ray beams to reach the target tissues substantially unimpeded by the radiopaque material.

FIGS. 1I and 1J depict a mechanism by which the coupling device 975 can be used to align the radiotherapy system 990. Laser pointer beam 977 (which is collinear with the radiation beam in some embodiments) is emitted from radiotherapy device 990 through a collimator opening 979 and reflects off a mirror 976 of the coupling device 975. In the non-alignment case depicted in FIG. 1I, the laser pointer beam 977 will not bounce back collinearly with the collimator opening 979, but will be off-axis, as shown by reflection point 980. The orientation of the radiotherapy system 990 can be manually or automatically adjusted by direct visualization of the location of the reflection point 980 or by sensors that detect the location of the reflection point 980 and adjust the radiotherapy system 990 to bring the laser pointer beam 977 into alignment. In the case where the laser pointer is in fact aligned (FIG. 1J), the laser pointer 977 is reflected, and the reflection point 980 is substantially collinear with the collimator opening 979.

Figure 1K:
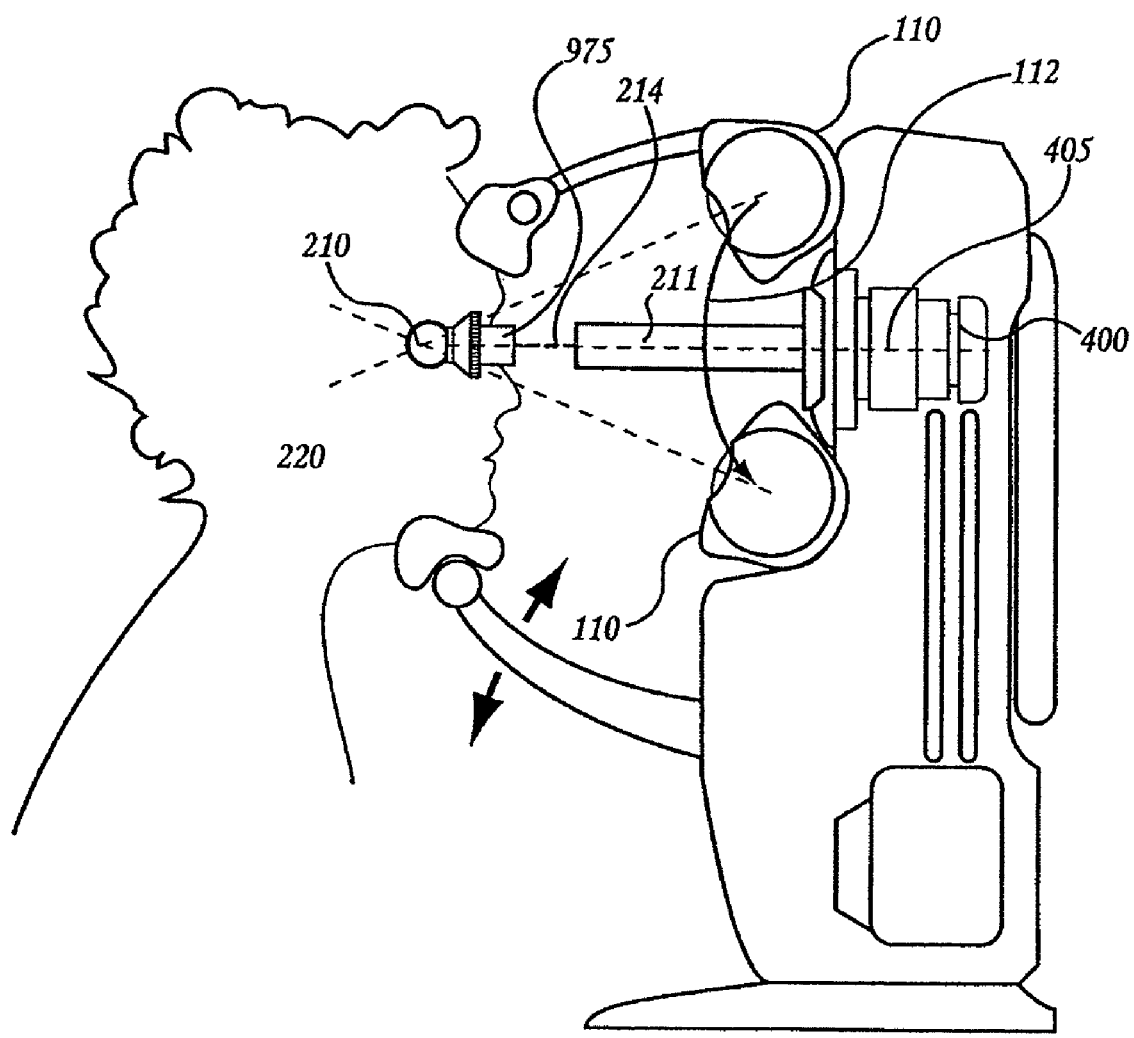
FIG. 1K depicts a radiotherapy system with an alignment system, which includes a lens interface.

FIG. 1K depicts the radiotherapy system with coupling device 975 in place. A treatment axis 214, which provides a reference about which application of the radiation beams are applied, is now coupled to or aligned with an system axis 211 of the radiotherapy system, about which the x-ray source 110 can be rotated, as indicated by arrow 112. The x-ray source 110 can rotate about the system axis 211 with or independent from the imaging subsystem 400 and its corresponding axis 405 (also illustrated in FIG. 1D). With the treatment axis 214 aligned with the system axis 211, and with the coupling device 975 engaging the eye 210, trajectories of the radiation beams can be determined to direct the radiation beams to be coincident with the target tissue of the eye 210 of the patient 220. The defined space of the treatment axis 214, the system axis 211, the location of the coupling device 975, and the location of the x-ray source 110 provides a confined coordinate frame that can be used, for example, for directing orientation and administration of the radiation beams.

In some embodiments, the x-ray source 110 can travel around a floating focal point, such as one that is defined by the treatment planning system and virtual model of the eye. A floating focal point is a focal point that can be programmed or located anywhere in the eye and moved to different locations during treatment, as opposed to a fixed focal point, such as the macula. In some embodiments, the x-ray source 110 can move with six degrees of freedom around a fixed or moving axis. In some embodiments, the x-ray source 110 remains fixed in one spot to treat an eye structure in the anterior portion of the eye, or even the posterior portion of the eye, depending on how large an area is to be treated and the dose required.

In some embodiments, the x-ray source 110 focuses x-rays on a target by moving to different positions around the eye 210 and delivering x-rays through the sclera at substantially different entry points on the sclera, but each x-ray beam reaching a substantially similar target within the eye. In some embodiments, the x-ray source 110 remains in one location, delivering x-ray energy to and through the sclera and to regions of the eye, such as the retina, and specifically the macula. In some embodiments, the x-ray source 110 is moved with six degrees of freedom, five degrees of freedom, four degrees of freedom, three degrees of freedom, or two degrees of freedom. In some embodiments, the x-ray source 110 is stationary and the collimator is moved or the eye or the patient is moved to project the beam to different regions of the eye. In some embodiments, the retina is treated by maintaining the x-ray beam in one position with respect to the sclera. The x-ray source 110 can be moved automatically by a robotic arm or manually by the operator of the system. The ultimate three-dimensional position of the x-ray source 110 can be dictated by the treatment plan which communicates between a model of the eye and with the robotic arm to determine the position of the x-ray beam relative to the eye.

In some embodiments, only a small amount of movement is required of the x-ray source 110 to treat a disease of the retina, such as macular degeneration and/or diabetic macular edema. In these embodiments, six degrees of freedom can be applied to the x-ray source 110, but the range of each degree of freedom is preferably limited so that the movement system only travels within a space of about 1000 cm$^3$, 500 cm$^3$, 100 cm$^3$, or about 50 cm$^3$. The speed of the robot within these volumes can be defined such that the robot moves 0.5 cm/s, 1 cm/s, 3 cm/s, 5 cm/s. Because each fractional treatment dose is relatively short and applied over a small distance, the robot can sacrifice speed and travel distance for smaller size.

In some embodiments, multiple x-ray sources are used, each positioned at different points in space so as to deliver a plurality of x-ray beams which will all converge on the target tissue, which can be one point on or in the eye. For example, the radiation system can have 3, 4, 5, or 6 x-ray sources that each have different, aligned trajectories that are all configured to intersect at a treatment location within the eye, which can include, for example, the fovea 240, depicted in FIG. 1C. Application of the x-ray beams can be performed simultaneously or in series. Treatment with a plurality of x-ray sources operating simultaneously can reduce treatment time, and consequently, reduce the likelihood of patient movement during the treatment period.

In some embodiments, it is a goal of the treatment system to deliver radiation therapy substantially through the pars plana region of the eye (see FIG. 1C). Pars plana 215 is the region of the eye between the pars plicata 218 and a peripheral portion of the retina 280, the ora serrata. The pars plana 215 region of the eye contains the fewest critical structures enroute from the sclera 260 to the retina 280. It is through this the region that surgeons can inject pharmaceuticals into the eye or to perform vitrectomies because the risk of damage to ocular structures is reduced with this approach. Likewise, radiotherapy can be delivered to the posterior region of the eye through the pars plana region 215 to minimize the potential for damage to structures, such as the lens, and yet still reach posterior regions, such as the fovea 240, with minimal radiation reaching the optic nerve 275. The image-guided orthovoltage therapy described herein allows such specific treatment.

In some embodiments, when a patient has an artificial intra-ocular lens, which may be unaffected by exposure to x-ray radiation, the radiotherapy can be delivered through the cornea and lens to the retina, directly through the central axis, the visual axis of the eye, or through the cornea. In some embodiments, treatment by x-ray radiation may be provided at the same time as a procedure for implanting an artificial intra-ocular lens.

With continued reference to FIG. 1C, the central axis 300 of the eye is typically defined by the geometric axis 300 and begins at the center of the curvature of the cornea 255; this axis 300 can also be called the optical axis or the treatment axis. The treatment axis can include any axis that is coincident with the treatment target. The visual axis 306 is represented by a line from the center of the fovea 305 through the center of the pupil 217. Angle kappa (k) 213 represents the angle between the visual axis 306 and optical axis 300. The geometric axis 300 can be defined by a perpendicular straight line or axis extending from the center of the cornea straight back to the retina 280. In this description, this axis can also be referred to as the treatment axis. The limbus 308 is generally the transition area where the cornea meets the sclera or visually, the point where the pigmented region of the eye meets the white region of the eye. The pars plana angle α 212 can be measured from the geometric central axis 300 and can range from about 10 degrees to about 50 degrees off the central geometric axis 300. The pars plana 215 region of the eye can be related to the central axis 300 of the eye through angle α 212. In some embodiments, x-rays with a tight collimation (e.g., smaller than about 6-8 mm in diameter) and a small penumbra (e.g., less than about ten percent at the sclera) enter the pars plana region 215 of the eye along a trajectory 250, avoiding some of the critical structures of the eye, to reach structures which are to be treated, such as the retina 280. In some embodiments as described herein, during the treatment, the eye can be stabilized with the assistance of physical or mechanical restraint or by patient fixation on a point so that the x-rays enter the eye substantially only in the pars plana region 215.

In certain embodiments, the patient is stabilized with respect to the axis of the eye. If the patient or device moves, then the imaging subsystem 400, or camera, detects the movement and turns the device off or closes a shutter over the region where the x-rays leave the device or the collimator. In some embodiments, the x-ray source 110 is moved about the eye to one or more positions determined by a treatment planning system, delivering radiation through the pars plana region 215 of the eye to reach the retina 280. The defined treatment axis and the trajectory through the tissue of the eye dictate the angle of delivery of the x-ray beam by the system relative to the treatment axis. The total dose is divided across different regions of the sclera but penetrates through the pars plana 215 region to reach the desired region of the retina (for example, the macula or the fovea).

As shown in FIGS. 1I-1J and as explained above, the mirror 976 can reflect the laser pointer beam 977 back toward the radiotherapy system 990. The reflected laser pointer beam 977 can activate a sensor 992 which can provide feedback relating to the position of the laser pointer beam 977 and inhibits or disinhibits the radiotherapy system 990. Alignment or misalignment of the radiotherapy system 990, as detected by the sensor 992, can be the trigger for the inhibition or disinhibition for the radiotherapy system 990. For example, in some embodiments, the laser pointer beam 977 can be configured such that the laser pointer light is reflected onto the sensor 992 when the eye is within an acceptable operational orientation. Accordingly, when the laser pointer light is reflected onto the sensor 992, the sensor 992 detects the reflected light and provides indication of the incident light to the radiotherapy system 990 or a processing module of the sensor 992 or system 990. The radiotherapy system 990 or processing module can be programmed such proper orientation of the eye and the system 990 is identified when the sensor 992 indicates that it has received reflected laser pointer light. The system can then be free to emit the radiation beams, and the radiation source can be powered to emit radiation beams or shutters on the system can be opened to permit radiation beams to be emitted to the eye.

If, during a treatment procedure, the eye moves, and the reflected laser pointer light no longer is incident upon the sensor 992, the system is notified by the sensor 992, indicating that the eye has moved and that the eye is no longer within the acceptable operational orientation. Power to the radiation emitter can then be terminated, or shutters on a collimator can be drawn, to stop emission of radiation to the eye.

In some embodiments, the reflected light or laser pointer 977 can indicate the degree of alignment between the coupling device 975 and mirror 976 and the radiotherapy device 990 from which the light source 977 originates. FIGS. 1I and 1J illustrates substantial coaxial alignment of the radiotherapy device 990 with the scleral lens 950 (FIG. 1P) and the geometric or visual axis of the eye 952 (FIG. 1J). In this instance, the reflected beam 977 and the incident beam 978 are indistinguishable as the reflected beam reflects 980 back onto the collimator 979 where the laser pointer originates. FIG. 1I depicts the case of misalignment where the incident beam 978 and its reflection 977 reflect back do not meet on the collimator 980, 979. A camera monitoring the status of alignment can signal the system to turn off when the incident beam 978 and its reflection 977 are not coaligned.

The head restraint 160 portion of the radiotherapy system 10 may be used for restraining the head of the patient 220 so as to substantially stabilize the location of the patient's eye 210 relative to the radiotherapy treatment system 10. The physician applying the treatment can align the central axis 300 of the patient's eye with the x-ray source 110. The restraint 160 can be configured to maintain the patient's position during the treatment. If the patient moves away from the restraint 160 or moves their eyes from the restraint, then the x-ray system can be turned off (e.g., by gating) manually or automatically and the patient's position readjusted.

In general terms, the patient's head is maintained in position with the head restraint 160 while the eye 210 is tracked by the imaging system 400 and/or treatment planning system and the x-ray source 110 is moved so that the x-ray beam enters the eye through the pars plana region 215; the x-rays, therefore, penetrate to the target regions of the retina and reduce the likelihood of significant damage as they pass through eye tissue toward the retina.

The treatment planning system 800 (FIGS. 1B and 2E) provides the physician interface with the system 10. The treatment plan is developed based on pre-treatment planning using a combination of biometric modalities including an imaging subsystem 400 that can include, for example, fundus photography, or optical coherence tomography, CT scans, MRI scans, and/or ultrasound modalities. The information from these modalities are integrated into a computer-generated virtual model of the eye which includes the patient's individual anatomic parameters (biometry) as well as the individual's specific disease burden. Any or all of these modalities can be utilized by the system in real time or integrated into the system prior to treatment. The treatment plan is output, for example, on the interface display 130 module of the radiotherapy system 10. The physician can then use the virtual model in the treatment plan to direct the radiation therapy to the disease using the radiotherapy system 10.

As used herein, "eye model" or "model of the eye" refers to any representation of an eye based on data, such as, without limitation, an anteroposterior dimension, a lateral dimension, a translimbal distance, the limbal-limbal distance, the distance from the cornea to the lens, the distance from the cornea to the retina, a viscosity of certain eye structures, a thickness of a sclera, a thickness of a cornea, a thickness of a lens, the position of the optic nerve relative to the treatment axis, the visual axis, the macula, the fovea, a neovascular membrane, a curvature of a cornea or a retina, a curvature of a scleral region, and/or an optic nerve dimension. Such data can be acquired through, for example, imaging techniques, such as ultrasound, scanning laser opthalmoscopy, optical coherence tomography, other optical imaging, imaging with a phosphor, imaging in combination with a laser pointer for scale, CT scan with or without contrast, and/or T2, T1, or functional magnetic resonance imaging with or without contrast. Such data can also be acquired through keratometry, refractive measurements, retinal nerve-fiber layer measurements, corneal topography, direct caliper measurement, etc. The data used to produce an eye model may be processed and/or displayed using a computer. As used herein, the term "modeling" includes, without limitation, creating a model.

The eye model is a virtual model which couples the anatomy of the eye with the coordinate system of the radiotherapy device. The eye model can be based on the geometry of the ocular structures and can be derived with parametric data and mathematical formulas to generate the model. Alternatively, the ocular geometries are derived from cross-sectional imaging, such as from CT scans or MRIs. With the treatment axis defined and the ocular anatomy defined, the coupling device can contact the ocular surface and link to the radiotherapy device via the eye model. The radiotherapy device is then positioned based upon the eye model.

In some embodiments, real time visualization of the eye can be utilized by emitting a laser that is aligned with the trajectory of the radiation beam. Observation of the location of the laser can be used to visually indicate proper orientation of the radiation beam trajectory. For example, it may be desired that the edge of the radiation beam be placed about 1 mm to about 4 mm from the limbus so as to avoid critical structures. As the laser pointer from the radiotherapy device reaches a spot 1-4 mm from the limbus, the radiotherapy eye model then uses the axial parameters of the eye to direct the radiotherapy device to the correct angle relative to the structure within the eye.

In some embodiments, the laser pointer is oriented on the sclera at a point that is desired to pass through the sclera. Once the laser pointer locates the desired location, the laser pointer is fixed on that portion of the sclera while the radiation source is oriented with respect to the desired location on the sclera, such that when the radiation source is activated and a radiation beam is emitted therefrom, the radiation beam will pass substantially through the desired location and a target location within the eye. A portion of the eye through which the radiation beam passes can be referred to herein as a traversal zone (e.g., 515 on FIG. 2D), or intersecting zone.

With continued reference to FIG. 1B, which shows a schematic overview of the treatment planning system 800, depicted by the background oval shape, and illustrating a global interconnect between four subsystems. The treatment planning system 800 directs the four subsystems toward treatment of the region and/or disease indicated by the physician. The four subsystems in general terms include an x-ray subsystem 700, a coupling subsystem 500, an electromotive subsystem 600, and an imaging subsystem 400. These subsystems or modules interact to provide an integrated treatment to the eye of a patient.

The subsystems work together to coordinate the treatment planning system 800. The treatment planning system (TPS) 800 also provides the interface between the physical world of the eye, the physical components of the system, and a virtual computer environment which interacts with the physician and treatment team and contains the specific patient and disease information. The coupling system 500, primarily, and the imaging system 400, secondarily, help link the physical world and the virtual world.

Within the virtual world, the treatment planning system creates a computer-generated virtual model of the patient's eye 505 based on physical and biometric measurements taken by a health practitioner or the imaging system 400 itself. The computer model 505 (FIG. 2D) in the virtual world further has the ability to simulate the projection 510 of an x-ray beam 520 from a radiation system 524 through an anterior region of the eye, which can include a traversal or intersecting zone 515, to the structure 514 to be treated based on different angles of entry into the eye. The model can also identify and include important eye structures, such as the optic nerve 512, to consider during the treatment planning process. The virtual world also contains the physician interface to control the device 524 and interface the device with respect to the physical world, or that of the actual physically targeted structure. After integrating the inputs from the physician and modeling the beam angles and desired direction to direct the therapy, the virtual world outputs the information to the electromotive subsystem to move the x-ray device to the appropriate position in three-dimensional space. The coupling subsystem 500 (in the physical world) can include a mechanism to determine the angle of incidence of the x-ray beam with respect to the surface of the eye using one or more laser or angle detectors, as discussed above.

In some embodiments, the coupling system 500 contains a camera 518 which can image a spot (real, reflected, fiducial, or projected fiducial) 516 on or in an eye; the camera can also visualize structures such as the pupil, cornea, sclera, limbus, iris, fundus, optic nerve, macula, or a lesion to be treated. Information from the camera is then preferably transferred to the virtual eye model 522 and again to the motion and radiotherapy system 524. In certain embodiments, the coupling system 500 is a physical connection with the eye. In some embodiments, the coupling system 500 is not a physical link but is a communication link between a lens on the eye and a detection system. For example, a lens can be a communication beacon to relay eye position to the system 500. In some embodiments, the lens can contain markers that are imaged by the imaging camera 518, through which the next stage in the therapy can be determined. In some embodiments, a combination of these techniques is used.

In some embodiments, the position of the eye and the x-ray source are known at all times, and the angles of entry of the x-ray can therefore be realized. For example, the central axis of the eye can be determined and defined as the treatment axis; the x-ray source offset a known angle from the central axis. The central axis, or treatment axis, in some embodiments can be assumed to be the axis which is perpendicular to the center of the cornea or limbus and extends directly posterior to the retina, as discussed previously. In some embodiments, the coupling subsystem can detect the "glint" or reflection from the cornea. The relationship between the glint and the center of the pupil is constant if the patient or the patient's eye is not moving. If the patient moves, then the glint relative to the center of the pupil is not in the same place. A detector can detect when this occurs, and a signal can be sent from the virtual world to the x-ray device to turn the x-ray device off or to shutter the system off. Alternatively, the coupling system can compare the center of a scleral lens relative to the center of the cornea. Both the lens and the cornea have respective glints and their alignment ensures that their centers are perpendicular to one another.

The information obtained from the coupling subsystem is preferably sent to the computer system and to the virtual eye model. The imaging subsystem 400 captures an image of the eye in real time with a camera 1460, depicted in FIG. 2C, and feeds the data into the software program that creates a virtual model of the eye. In combination with the physical world coupling system 500, the predicted path of the x-ray beam through the eye can be created on the virtual image. Depending on the region to be treated, the electromotive system and/or x-ray system can be readjusted; for example, a robot arm can move the x-ray source 110 to a position to send a radiation or x-ray beam to a location on or in the eye based on the model of the eye as created by the TPS and as captured by the imaging system 400.

In certain embodiments, the radiotherapy generation system 100 can include an orthovoltage (or low energy) radiotherapy generator as the x-ray subsystem 700, as discussed in further detail with reference to FIG. 1A, a schematic of the device. The radiotherapy generation subsystem 110 generates radiotherapy beams that are directed toward the eye 210 of the patient 220 in FIG. 1A. In certain embodiments, the radiotherapy control module 120 includes an emitter 200 that emits a directed, narrow radiotherapy beam generated by the radiotherapy generation subsystem 110.

As used herein, the term "emitter" is intended to have its plain and ordinary meaning, and the emitter can include various structures, which can include, without limitation, a collimator and/or a filter. In some embodiments, the control module 120 is configured to collimate the x-ray beams as they are emitted from the radiotherapy generation subsystem 110.

The x-ray subsystem 700 can direct and/or filter radiotherapy rays emitted by the x-ray tube so that only those x-rays above a specific energy pass through the filter. In certain embodiments, the x-ray subsystem 700 can include a collimator through which the pattern or shape of an x-ray beam is determined. The filtering of the source preferably determines the amount of low energy inside the x-ray beams as well as the surface-depth dose as described in ensuing figures. In some embodiments, it is desirable to deliver orthovoltage x-rays with a surface-to-depth dose less than about 4:1 to limit dose accumulation at the surface of the eye. In some embodiments, it is desirable to have a surface-to-depth dose less than about 3:1 or about 1.5:1 but greater than about 1:1 when using orthovoltage x-rays. The surface-depth dose can also be altered by changing the maximum beam energy leaving the x-ray tube. For example, for a disease on the surface of the eye such as pterygia or to treat post-trabeculoplasty scarring, the maximum beam energy leaving the x-ray tube may be lower, such as about 40 keV, about 50 keV, or about 60 keV. In these diseases it may be desirable to have about a 30:1, 50:1, or 100:1 surface to depth ratio. Therefore, the radiotherapy control system can control one or more of the power output of the x-ray, the spectrum of the x-ray, the size of the beam of the x-ray, and the penumbra of the x-ray beam.

In certain embodiments, the electromotive subsystem 600 of the radiotherapy system may move the x-ray source and the collimator to direct a narrow radiotherapy beam emitted from the x-ray source to irradiate specific regions of the patient's eye 210 by directing energy onto or into targeted portions of the eye 210, while at the same time avoiding irradiation of other portions of the eye 210. For example, the system 10 may target a structure of the posterior region of the eye, such as the retina, or a structure on the anterior region of the eye, such as the trabecular meshwork, the sclera, the cornea, the ciliary processes, the lens, the lens capsule, or the canal of schlemm. The system 10 can deliver radiotherapy to any region of the eye, including, but not limited to, the retina, the sclera, the macula, the optic nerve, the ciliary bodies, the lens, the cornea, Schlemm's canal, the choroids, the capsular bag of the lens, and the conjunctiva.

In certain embodiments, the x-ray subsystem 700 can collimate the x-ray to produce a narrow beam of specified diameter and shape. For example, in certain embodiments using a collimator, the diameter of the collimator outlet may be increased or decreased to adjust the diameter of the radiotherapy beam emitted by the collimator. In certain embodiments, the x-ray subsystem 700 can emit a beam with a diameter of about 0.1 mm to about 6 mm. In certain embodiments, the x-ray subsystem 700 can emit a beam with a diameter of less than about 0.1 mm. In certain embodiments, the x-ray subsystem 700 can emit a beam with a diameter of between about 0.5 mm and about 5 mm. As described in further detail below, narrow beams and virtual models are useful to ensure that the energy is applied to a specific area of the eye and not to other areas of the eye.

In some embodiments (FIG. 2B'-2B'''), the radiation control module can emit an x-ray beam with a circular 1212 or non-circular 1214 shape; in some embodiments, the radiation control module can emit an x-ray beam with a rectangular shape 1214 or a square shape. In some embodiments, the radiation control module can emit an x-ray beam with an arc shape or an elliptical shape or a doughnut configuration 1217 through a circular collimator 1215 with an opaque region 1218 in the center. In some embodiments, the collimator 1215 can include a conical-shaped opening 1232, such as depicted in FIG. 2B'''', for providing a precisely shaped beam 1200. In some embodiments, the collimator 1215 has multiple openings (see, e.g., FIG. 2B'''') such that the x-ray has a specular, dotted configuration when it reaches the sclera and retina. The speckled configuration of the x-ray, which can be termed "micro-fractionation", may allow for an improved safety profile because less radiation will be applied to the retina and choroid normal blood vessels.

In certain embodiments, the radiotherapy system 10 allows for selective irradiation of certain regions of the eye without subjecting other areas of the eye to radiation by using a narrow, directed treatment beam, the treatment beam dictated by the specific anatomy of the patient's eye. For example, the radiotherapy control module 120 can direct radiotherapy beams generated by the radiotherapy generation module 110 to a patient's macula, while substantially avoiding radiation exposure to other portions of the patient's eye, such as the lens, the trabecular apparatus, and the optic nerve.

By selectively targeting specific regions of the eye with radiation based on knowledge of the anatomy of the eye and linking the radiation system to the anatomy for treatment purposes, areas outside of the treatment region may avoid potentially toxic exposure to radiation. In some embodiments, the x-ray beam follows a trajectory 250 that enters the eye through the pars plana region 215 which is a zone of the sclera 260 between the iris 270 and the retina 260. By directing the beam to this region and limiting the penumbra or scatter of the beam using specialized collimators, the beam can be localized onto an eye structure with minimal photon delivery to other structures of the eye, such as the cornea 255, the ciliary body and fibers 216 and other structures.

In certain embodiments, the radiotherapy treatment system 10 can include a shutter for controlling the emission of radiotherapy beams. The shutter may comprise a material opaque to the radiation generated by the radiation generation module 110. In certain embodiments, a shutter may be used to control the emission of beams from the radiotherapy generation module 110. In certain embodiments, a shutter may be used to control the emission of beams from the radiotherapy control module 120. In certain embodiments, the shutter may be internal to either of said modules 110 and 120, while in certain embodiments, the shutter may be external to either of said modules 110 and 120. In some embodiments, the system 10 is turned off to stop x-ray delivery, and in certain embodiments, the x-ray source 110 is turned off or its intensity turned down to limit or stop x-ray delivery to the target. In certain embodiments, the shutter or aperture changes shape or size.

In certain embodiments, and as explained above with respect to FIG. 1A, the radiotherapy treatment system 10 can deliver radiotherapy beams from one angle. In certain embodiments, the radiotherapy treatment system 10 can deliver radiotherapy beams from more than one angle to focus the beams on the treatment target. Certain embodiments of the system 10 that can deliver radiotherapy beams from more than one angle can include a plurality of stationary radiotherapy directing modules. The stationary radiotherapy modules can be positioned in a wide variety of locations to deliver radiotherapy beams to the eye at an appropriate angle. For example, certain embodiments of the radiotherapy treatment system 10 include five radiation source module-radiation directing module pairs that are connected to the radiotherapy treatment system 10 in such a way that they are spaced equidistantly around a circumference of an imaginary circle. In these embodiments, the power supply could be a switching power supply which alternates between the various x-ray generators. Certain embodiments of the system 10 that can deliver radiotherapy beams from more than one angle can also include moving the radiotherapy directing module. Certain embodiments of the system 10 that can deliver radiotherapy beams from more than one angle can also include moving the radiotherapy source using an electromotive subsystem 700 (FIG. 1B), such as a robot.

In some embodiments of the present disclosure, orthovoltage x-rays are generated from the x-ray generation module 700. X-ray photons in this orthovoltage regime are generally low energy photons such that little shielding or other protective mechanisms can be utilized for the system 10. For example, diagnostic x-rays machines emit photons with orthovoltage energies and require minimal shielding; typically, only a lead screen is used. Importantly, special rooms or "vaults" are not required when energies in the orthovoltage regime are used. Diagnostic x-ray machines are also portable, being transferable to different rooms or places in the clinical environment. In contrast, linear accelerators or LINACS which typically deliver x-rays with energies in the MeV range require thickened walls around the device because higher energy x-ray photons have high penetration ability. Concomitant with the higher energy photons, LINACS require much greater power and machinery to generate these high energy photons including high voltage power supplies, heat transfer methodologies, and internal shielding and protection mechanisms. This increased complexity not only leads to higher cost per high energy photon generated but leads to a much heavier device which is correspondingly more difficult to move. Notably, as described above and demonstrated experimentally, as discussed below, MeV photons are not necessary to treat superficial structures within the body and, in fact, have many disadvantages for superficial structures, such as penetration through the bone into the brain when only superficial radiation is required.

X-Ray Subsystem

The x-ray subsystem 700 generates x-rays and can include a power supply, a collimator, and an x-ray tube. In certain preferred embodiments, the x-ray subsystem 700 includes an orthovoltage x-ray generation system 1070 to produce orthovoltage x-rays with energies between 10 keV and 500 keV or even up to 800 keV. This type of x-ray generation scheme includes a high voltage power supply that accelerates electrons against a tungsten or other heavy metal target, the resulting collision then generating electromagnetic energy with x-ray energies.

Orthovoltage or low energy x-ray generators typically emit x-rays in the range from about 1 keV to about 500 keV or even up to about 1 MeV. In some embodiments, the system described herein emits x-rays with photon energies in the range from about 25 keV to about 100 keV. The use of low energy x-ray systems allow for placement of these x-ray treatment systems in outpatient centers or other centers and will not require the overhead and capital requirements that high energy (MeV or gamma) x-ray systems require. In the treatment of opthalmologic disorders, such as AMD, placement in the ophthalmologist office or close to the opthalmologic office is important because the ophthalmologists can treat many more patients, a very important component when treating a disease that afflicts millions of patients. If the device were limited to operating within vaults inside radiation oncology centers, the number of treatable patients would be much more limited because of access, cost, competition with other diseases, and other logistics.

The radiation generation module in some embodiments is composed of components that are arranged to generate x-rays. For example, a power supply generates current which is adapted to generate and accelerate electrons toward an anode, typically manufactured from a heavy metal such as tungsten, molybdenum, iron, copper, nickel, or lead. When the electrons hit one of these metals, x-rays are generated.

An exemplary set of x-ray spectra is shown in FIG. 1F. The term "kVp" refers to the maximum (peak) voltage of the x-ray power supply. It is typically identical to the maximum photon energy delivered by the x-ray source (keV). When x-rays are generated by high voltage electricity, a spectrum of x-ray at various x-ray levels is obtained, a typical spectrum set shown in FIG. 1F. The maximum voltage is typically identical to maximum x-ray photon energy. For example, the 80 kVp spectra in FIG. 1F has a maximum of 80 keV with a leftward tail of lower energy radiation. Similarly, the 60 kVp spectrum has a maximum of 60 keV with a similar leftward tail. All spectra in the figure have been filtered through 3 mm of Aluminum. Filtering shapes the spectral curve. Lower wavelengths are filtered to a greater degree than the higher wavelengths. Filtering of the raw spectra is important to customize the x-ray energy for the application at hand where the superficial energy, if not filtered, would be absorbed by the superficial structures of the eye (e.g., sclera). To the extent that it is desired that x-ray energy reach the structures of the retina with minimal energy absorption by the anterior structures of the eye, filtering of the raw spectra is important to the system; with filtering, the resulting spectrum contains a greater amount of high energy photons than low energy photons, essentially a low-pass filter. As described, for some disease processes, it is desirable to have a predominance of low energy x-ray reach the anterior structures of the eye in which case the lower voltages will be used with correspondingly lower keV peaks. Adjustment of the power on the power supply will result in a decrease in the peak voltage of x-rays, limiting the amount of higher energy photons. In some embodiments, it may be desirable that a non-uniform filter be used. For example, the filter may have varying thicknesses across it to accommodate varying differences in the x-ray spectra in one treatment region.

A power supply 150 as shown in FIG. 1A powers the radiation module. The power supply 150 is rated to deliver the required x-ray with a given current. For example, if 80 KeVp x-rays are being delivered from the source at 10 mA, then the power required is 800 W (80 kilovolts×0.01 A). Connecting the power supply to the x-ray source is a high voltage cable which protects and shields the environment from the high voltage. The cable is flexible and in some embodiments has the ability to be mobile with respect to the power supply. In some embodiments, the power supply is cooled with an oil or water jacket and/or convective cooling through fins or a fan. The cooling fluid can move through the device and be cooled via reservoir outside the system 10.

Electromotive Subsystem

Figure 12A:
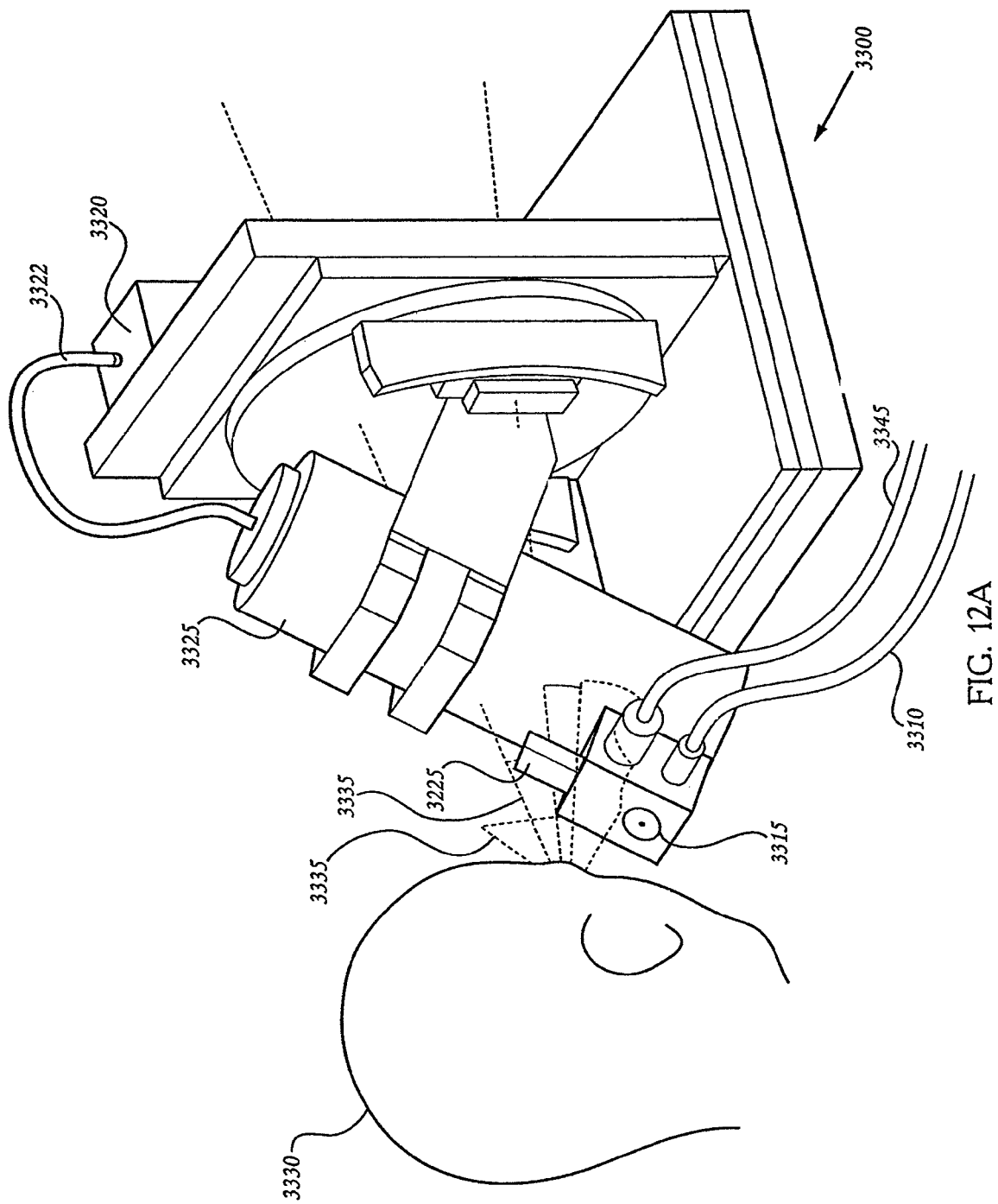
FIGS. 12A-12B depict embodiments of robotic systems, as described herein.

FIGS. 2A and 12A depict embodiments of the electromotive subsystem 600 of the treatment system 1000 illustrated in FIG. 1B. The subsystem is an advantageous component of the therapeutic system because it controls the direction and the size of the x-ray beam in relation to the anatomy of the eye and the disease to be treated. In general terms, the electromotive subsystem is directed in the space of the global coordinate system 1150 by the personalized eye model created from the patient's biometric data. The data from the model is transferred through the treatment planning system to the electromotive subsystem 600 to direct the x-ray beam to the target on or in the eye.

In certain embodiments, the system can include a collimation system 3315, a shutter system, and an electromechanical actuation system to move the x-ray source and/or collimators. Referring to FIGS. 2A and 12A, orthovoltage x-ray source, or tube, 1070, 3325 is depicted. Collimators 1030, 1040, 1052, 3315 are calibrated to produce a small collimated beam 1062 of x-ray photons; in a preferred ophthalmic embodiment, the tightly collimated beam 1062 has an area of from about 1 $mm^2$ to about 20 $mm^2$ in a circular or other shape and a diameter of from about 0.5 mm to about 6.0 mm. Multiple collimators allow for improved penumbra percentages; the smaller the penumbra, the finer the application of x-rays to a specified structure. FIGS. 2B'-2B''' depict embodiments of collimator designs in which a variety of collimator configurations are depicted. For example, FIG. 2B''' depicts a collimator configuration in which a doughnut, or annular, shape of x-rays is generated; FIG. 2B'''' depicts a collimator configured with a nozzle, or conical, shape 1232 to limit the penumbra or create a substantially uniform radiation beam. Other cross-sectional shapes can include, for example, concentric rings, an ellipse, a circle, a polygon, and a crescent. The collimators, operating in conjunction with filters 1010, 1020 preferably cause the x-rays to leave the collimator in a beam 1062 having a substantially parallel configuration.

In certain embodiments, electromotive system 3300 is customized to treat the eye with doses of radiation in a range of positions 3335. The range of positions 3335 is limited because the eye and treatment volume are small, and the source is positioned relatively close to the treatment region. As determined by the other components of the system as well as the ocular geometry, x-ray tube 3325 may only move within a volume of about 1 $cm^3$ to about 5 $cm^3$ for the entire treatment program. Also dictated by the x-ray tube size and energy, the time for movement through this volume may take place over a period of minutes which limits the size of the motors required to run the electromotive system and allowing for a table top positioning system 3300. The limited movement of the positioning system also allows the cooling tubes 3345 and power supply tubes 3322, leading from the power supply 3320, to be relatively constrained and not move with the tube, further simplifying the system. Because the system is customized for treating the eye, many elements of the x-ray generation system are smaller than, for example, linear accelerators. Customization for the eye allows more flexibility of the system as far as placement in a greater number of locations and physician useability.

The electromotive subsystem, or control system, 600 interacts with and is under the direction of the global treatment planning system 800 in FIG. 1B. The electromotive subsystem 600 receives commands from the treatment planning system 800 which can dictate among other things, the length of time the x-ray machine is turned on, the direction of the x-ray beam with respect to the eye target using data from the eye model or treatment planning system, the collimator size, and the treatment dose. The eye target 1300 and the control system 600 can be linked in global coordinate space 1150 which is the basis of the coupling system. The treatment planning system 800 directs the therapy using global coordinate system 1150. The x-ray control system 600 dictates the direction and position of the x-ray beam with respect to the ocular target and moves the x-ray source into the desired position as a result of commands from the treatment planning system 800.

In some embodiments, the collimators and/or the x-ray source can be placed on a moving wheel or shaft (1100, 1110, 1120) with one or more manual or automated degrees of freedom allowing the beam to be moved to a multitude of positions about the globe of the eye. In some embodiments, the x-ray source 1070 is movable with greater than one degree of freedom such as with a robot or automated positioning system 3300. The robot moves the x-ray source with respect to a global coordinate system such as a cartesian coordinate system 1150 or a polar coordinate system. The origin of the coordinate system can be anywhere in physical space which is convenient. In some embodiments, the x-ray source is movable with four, five, or six degrees of freedom. In some embodiments, a robot is also utilized to move any of the other components of the x-ray control system such as the collimators. In some embodiments, the collimators are controlled with their own electromechanical system.

The electromotive subsystem can also contain one or more shutters to turn the beam on and/or off in an instant if desired (for example, if the patient were to move away). The x-ray source 1070 and/or collimators can move in any axis in space through an electromechanical actuation system (1100, 1110, 1120).

Figure 2C:
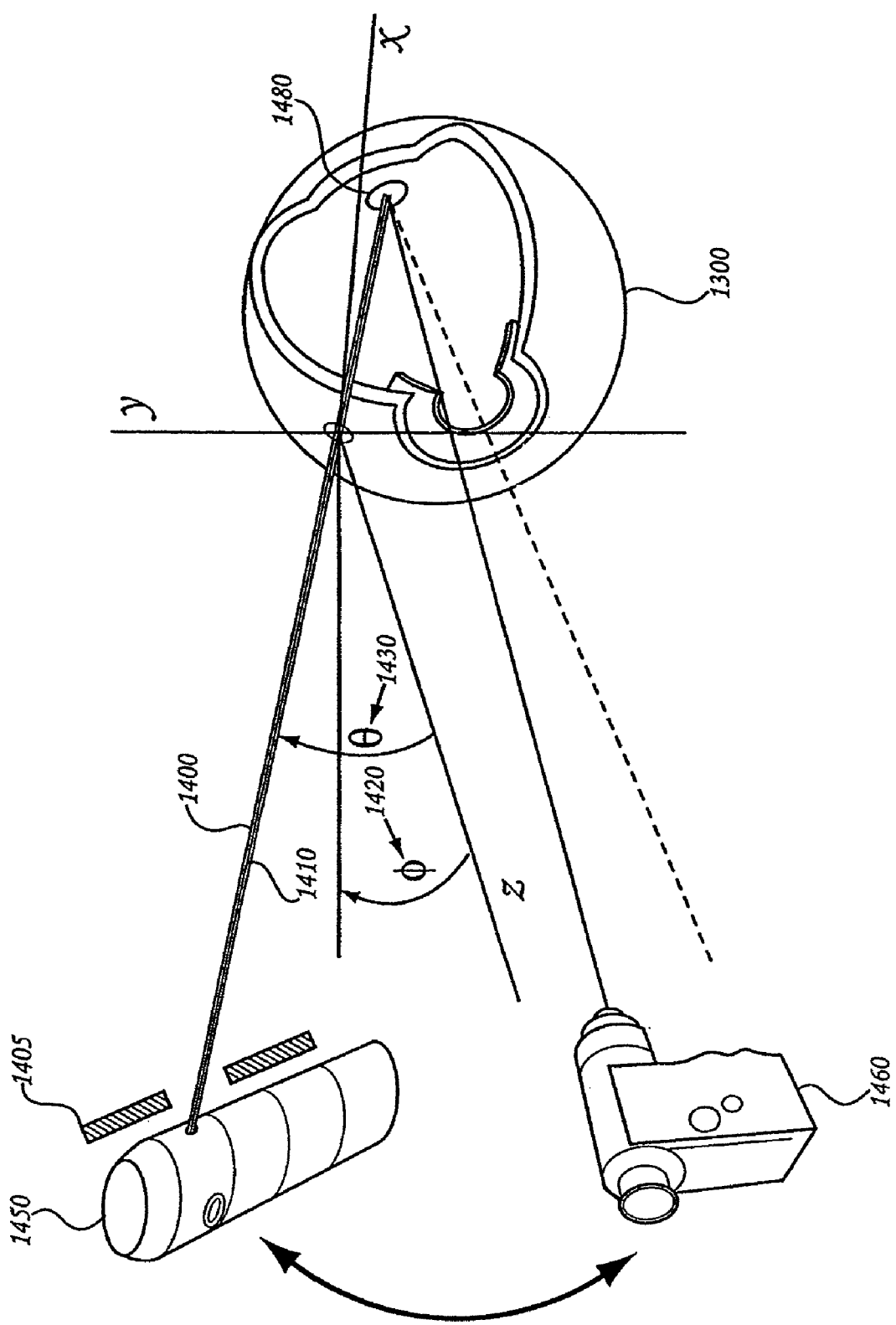
FIG. 2C illustrates embodiments of a radiotherapy system targeting a location within an eye for treatment.
Figure 2D:
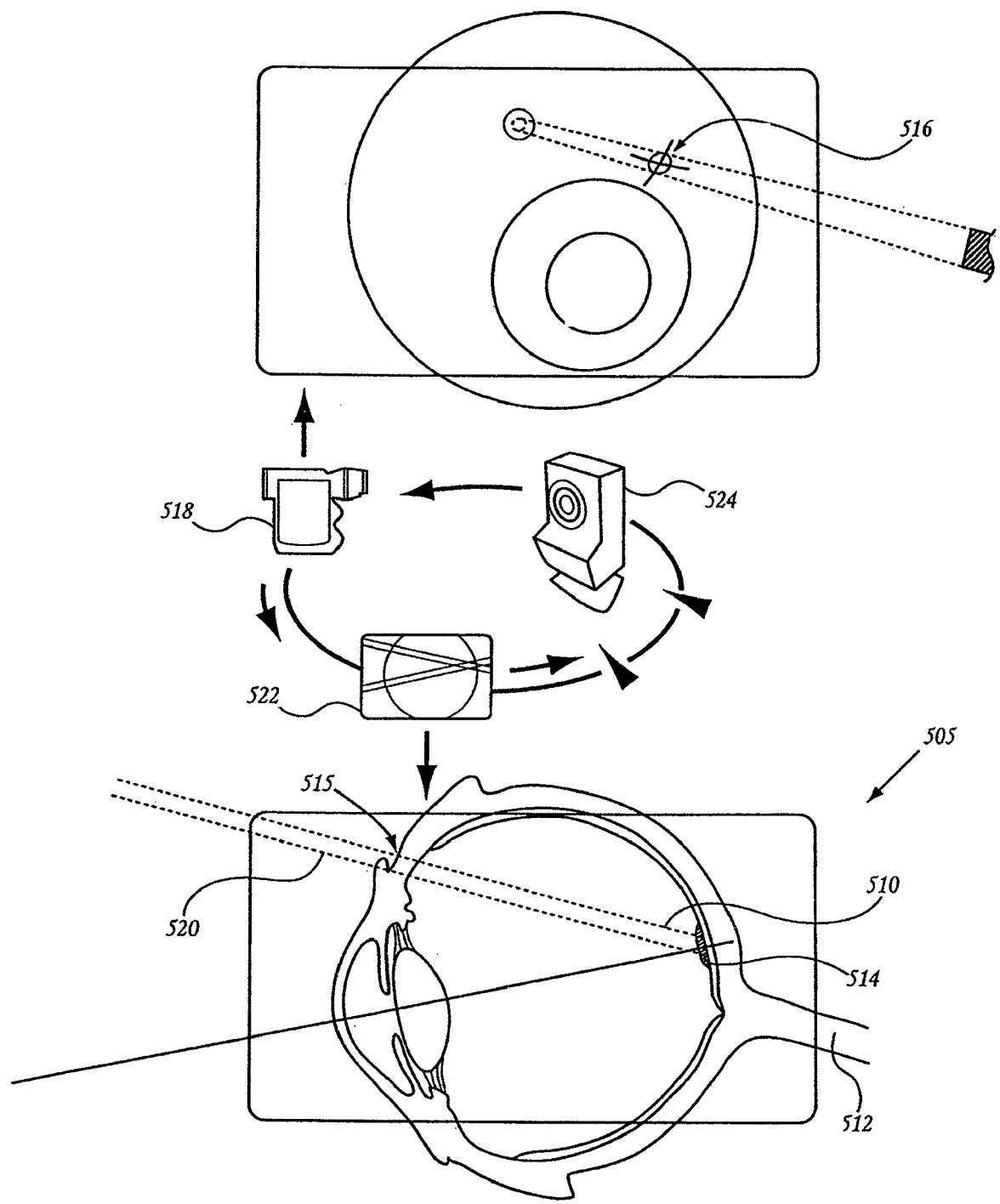
FIG. 2D illustrates some embodiments of a radiotherapy system targeting a location within an eye for treatment.

The x-ray coupling subsystem 500 integrates with the x-ray generation subsystem 700 under the umbrella of the treatment planning system 800. Also depicted in FIG. 2A, and in more detail in FIG. 2C, is at least one laser pointer or other relatively collimated light source (e.g., a light emitting diode with a small angle of divergence) 1060 (1410 in FIG. 2C) which can serve multiple purposes as described. In some embodiments, the laser pointers 1060 couple with the direction of the collimated x-ray beam 1062 so that the centroid of the laser beam is approximately identical to the centroid of the x-ray beam 1062 so as to have a visible marker as to where the x-ray beam is being delivered. Because x-rays are not visible, the laser pointers serve to identify the direction of the x-ray beam relative to other parts of the radiotherapy system. Where the center of the x-ray beam is directed, the center of the laser beam is correspondingly directed as well as shown in FIG. 2C.

Radiotherapy Coupling Subsystem

A third major subsystem of the present disclosure is the coupling subsystem or module 500. In general terms, the coupling module 500 coordinates the direction of the x-ray beam position to the position of the eye. As depicted in FIGS. 2A-2D and described above, some embodiments include laser pointer 1060 (one or more may be desired) that is collinear with the x-ray beam. In some embodiments, the laser pointer(s) allows for detection of the angles of incidence of the laser beam 1500 (FIG. 3A) with respect to the sclera or other surface they impinge upon. The angles of incidence 1510, 1520 can be defined by two orthogonal entrance angles (θ, φ) on the sclera or other surface. Centroids of the one or more laser pointers 1060 preferably coincide with the centroid of the x-ray beam as it impinges on the sclera or other surface.

As will be described in greater detail below, the laser pointer can also serve an important purpose in the imaging subsystem which is to provide a visual mark (FIG. 3A) 1570 on a surface of an eye 1600 when the eye is imaged by the camera 1550 and digitized or followed in the imaging subsystem. With the visual mark 1570 on the digitized image and the angles of incidence 1510, 1520 of the laser beam 1500, computer generated projections 1700, 1730 of the x-ray (or laser) (FIG. 3B) can be produced on a computer-generated (virtual) retina 1720. In some embodiments, the projections 1700, 1730 are the same, and in some embodiments, the projections can be distinct. For example, in some embodiments, the projection 1700 external to the eye may have different characteristics (e.g., trajectory, penumbra, etc.) than does the projection 1730 within the eye.

The computer-generated virtual retina 1720 (FIG. 3B) is described in further detail below and is a component of a virtual ocular model and is obtained via real data from an imaging system such as, for example, an OCT, CT Scan, MRI, A- or B-scan ultrasound, a combination of these, or other ophthalmic imaging devices such as a fundoscopy and/or scanning laser opthalmoscopy. In addition to the retina 1720, x-ray delivery to any structure within the eye can be depicted on the virtual ocular model 1725.

Figure 3A:
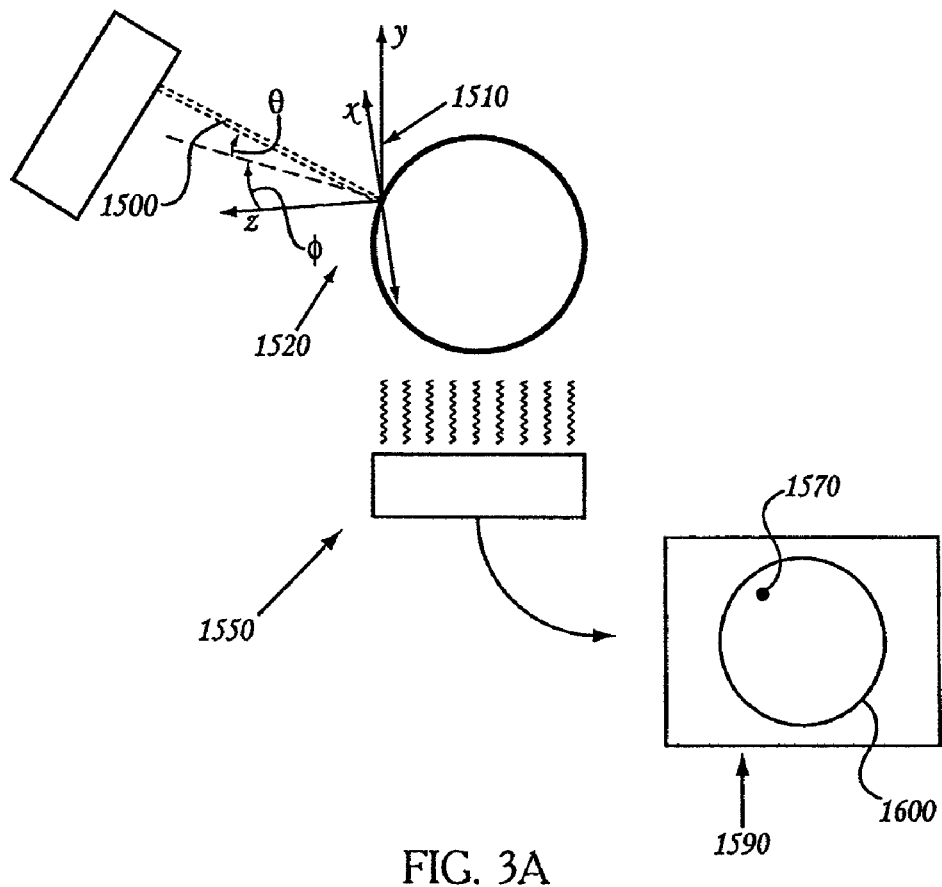
FIGS. 3A and 3B depicts embodiments of a subsystem of a radiotherapy control module.
Figure 3B:
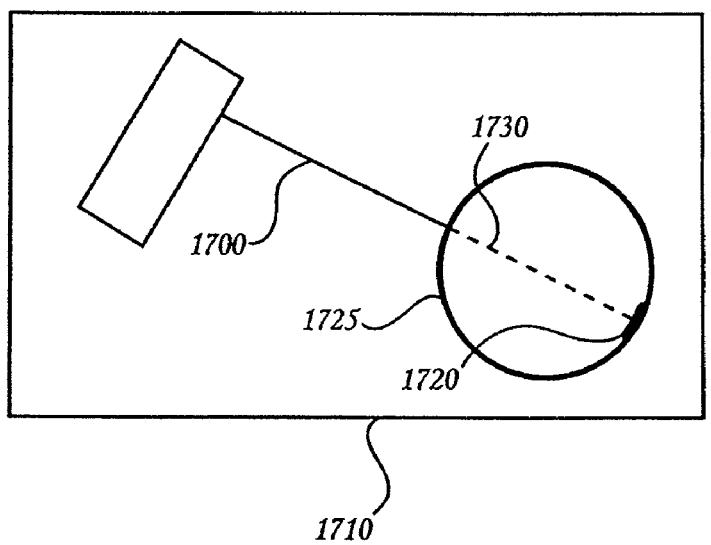

As shown in FIG. 3A, laser beam 1500 is shown as the mark 1570 on screen 1590, which is a depiction of the image seen by the camera 1550 and then in digitized form within the treatment planning system 800. With angles θ1520 and φ1510 and the location of the mark 1570 of the laser pointer on the digitized image of the eye 1600, the path 1730 through a "virtual eye" 1725 can be determined in a computer system 1710 (FIG. 3B). If the position is not correct, a signal can be sent back to the electromotive module in order to readjust the targeting point and/or position of the laser/x-ray.

In certain embodiments, a second camera can be used so as to detect the angles of the laser pointer and x-ray beam. These angles can be used to detect the direction of the x-ray beam and send a signal to the electromotive system for re-positioning. This feedback system can ensure proper positioning of the electromotive subsystem as well as correct dosing of the x-ray irradiation to the eye.

In some embodiments, an analogue system is used to detect the position of the eye. In these embodiments, the target structure, the eye, is assumed to be in a position and the x-ray control system positions the x-ray source around the globe of the eye, then applying the pre-determined amount of radiation to the eye structure.

In certain embodiments, as depicted in FIG. 1E, a physical connection to the eye is used for direct coupling between the eye and the radiotherapy system. In these embodiments, a connection between the eye and the system can be mediated by a lens, such as a scleral contact lens 935. A physical link between the lens 935 and the system 10 is then provided by structure 175 which directly links to the radiotherapy system 10. The scleral lens 935 can be a soft or hard lens. The lens 935 can further contain one or more connections so that suction can be applied to the sclera so as to stabilize the eye during the therapy.

The scleral lens 935 and associated attachments can be used to localize the eye in space. When the position of the sclera is known with the lens, the position of the eye is known as well. The eye is then coupled to the radiotherapy device 10. In some embodiments, the connection between the contact lens and the radiotherapy device 10 is a non-mechanical connection in that the connection is an optical one such as with a laser pointer or one or more cameras to detect the actual position of the eye relative to the radiotherapy system. The position of the eye in physical space is used to simulate the position of the beams in the virtual eye model and then back to the physical world to place the x-ray system to deliver the desired beam direction, angles, positions, treatment times, etc.

In some embodiments (e.g., see FIG. 2G), a schematic of the alignment system is depicted for radiosurgery device 2745. The treatment axis 2735, as described, is represented by a line perpendicular from the system, through a patient interface (e.g. a scleral lens), to the posterior pole of the eye 2720. A camera 2740 can image the region at the front of the eye or the region where the laser pointer 2765 exits. The macular lens and guide 2730 can contain a mirror which can reflect the laser pointer beam back on to the radiosurgery system, the reflection being detectable by the camera 2740. When the radiosurgery system and the mirror are perpendicular to one another, the entire system is then aligned along the treatment axis 2735 (as described above with respect to FIGS. 1I and 1J). Similarly, this type of alignment system can also be used to gate the radiotherapy system to misalignment or to patient/eye movement. For example, the reflection from the mirror can communicate with a sensor. In the absence of direct communication between the reflected beam and the sensor, the radiotherapy system can be gated off.

In some instances, it is desirable to know the scatter dose of the x-ray beam being delivered to a treated structure within the eye. For example, when neovascularization is being treated in the retina with a beam traveling through the sclera, scatter to the lens or optic nerve may be modeled. In some instances, it may be desired to know the dose to the neovascular membrane on the retina, the primary structure to be treated.

Imaging Subsystem

Figure 4:
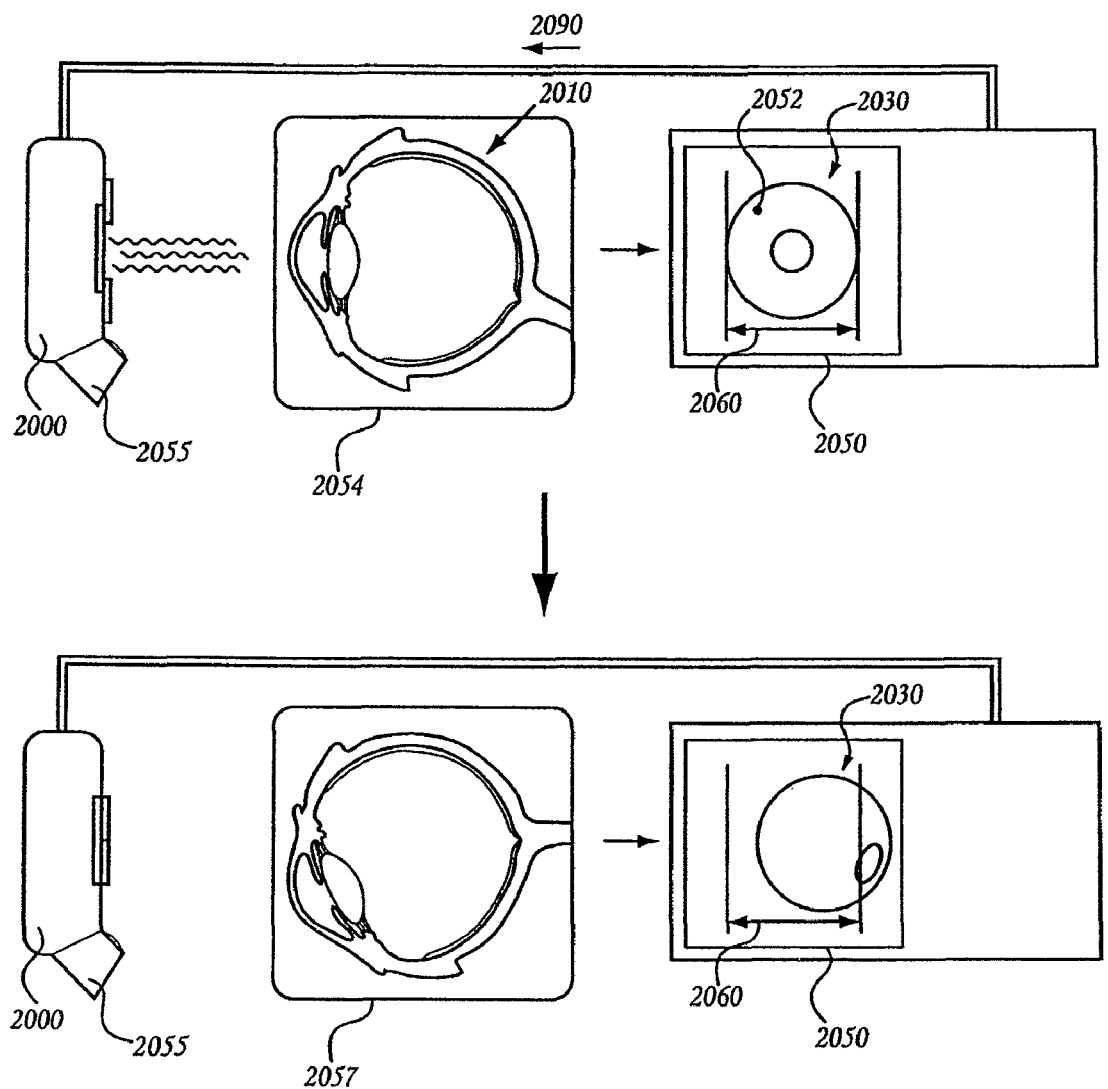
FIG. 4 illustrates a side view of an eye wherein eye location is tracked according to methods described herein.

Another advantageous feature of embodiments described in this disclosure is the imaging subsystem 400, which can also serve as an eye tracking system (FIG. 4) and offers the ability to couple patient movement or eye movement with the other subsystems above. This subsystem 400 advantageously ensures that the patient's eye 2010 does not grossly move out of the treatment field 2060. Camera 2055 can be the same camera 1550 in FIG. 3A. The camera 2055 delivers an image to screen 2050. The imaged laser spot 2052 is also shown on screen 2050. The video screen 2050 can be the same video screen 1710 in FIG. 3B. Field 2060 in FIG. 4 is the zone within which the eye can move; if the eye 2010 moves outside the zone 2060 on the screen, then the radiation source is either turned off, shuttered off, or otherwise disengaged from the eye 2010. In some embodiments, when an image of the eye 2030 reflects that the eye 2010 has moved out of field 2060, a signal 2090 is sent to the x-ray control system (FIG. 2A) to turn the shutter off. Aside from ensuring that the eye remains within the treatment field, the imaging system couples to the other subsystems by enabling projection of the laser pointer/x-ray beam 2052 on the back of the computer generated virtual eye.

In some embodiments, the imaging subsystem is composed of two or more cameras which are used to create a three-dimensional rendering of the eye in space, the three-dimensional rendering then integrated into the overall treatment scheme.

Treatment Planning System

The treatment planning system 800 is, in part, a virtual system and is depicted in FIG. 1B; it integrates all of the inter-related modules and provides an interface for the health care provider as well. The planning system 800 is the "brains" of the system 10 and provides the interface between the physician prescribing the therapy and the delivery of the therapy to the patient. The treatment planning system integrates anatomic, biometric, and in some cases, geometric assumptions about the eye "the virtual eye model" with information about the patient, the disease, and the system. The information is preferably incorporated into a treatment plan, which can then direct the radiation source to apply specific doses of radiation to specific regions of the eye, the doses being input to and output from the treatment planning system 800. In certain embodiments of the treatment planning system 800, treatment with radiation may be fractionated over a period of days, weeks, or months to allow for repair of tissues other than those that are pathologic or to be otherwise treated. The treatment planning system 800 can allow the physician to map the treatment and dose region and to tailor the therapy for each patient.

Figure 2E:
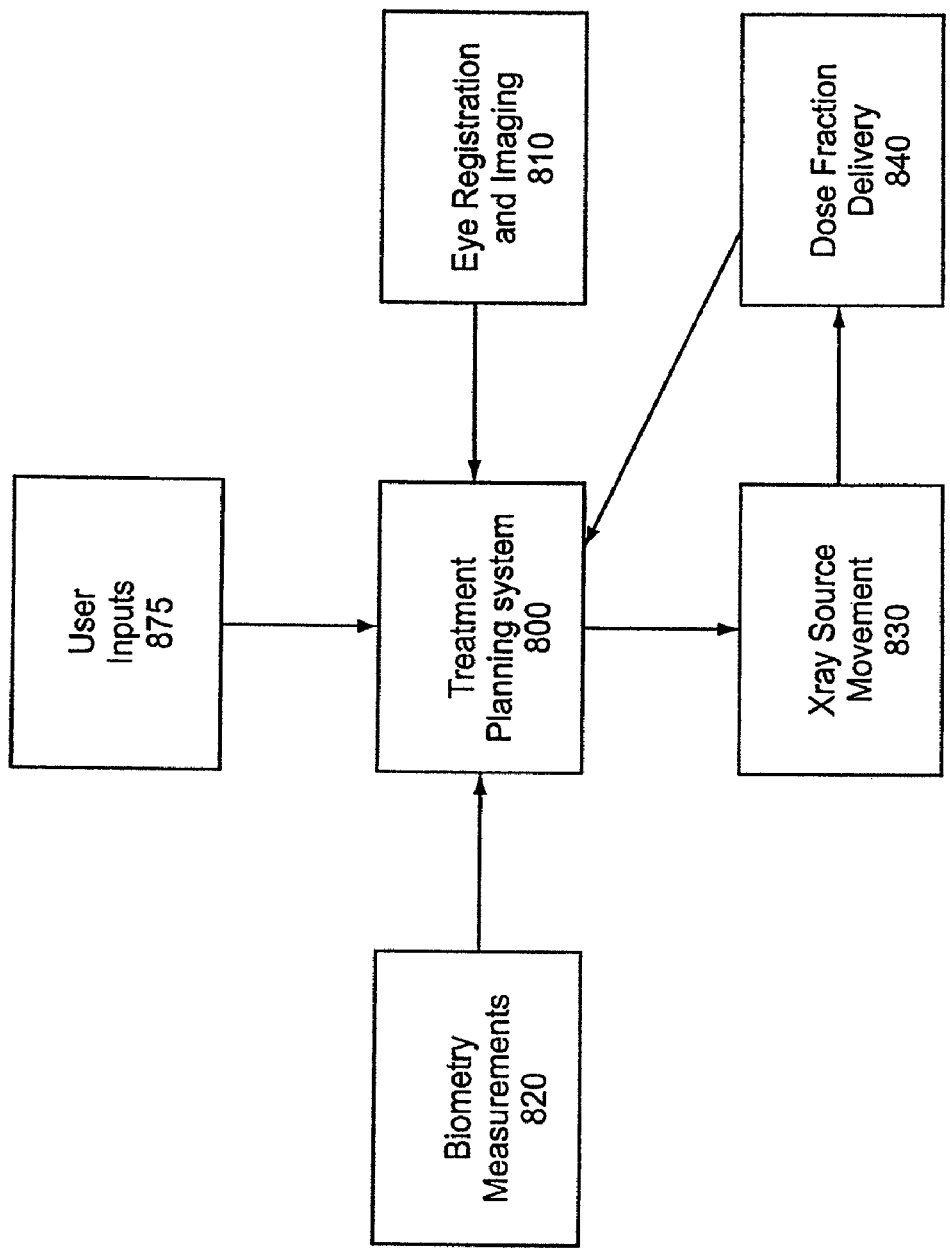
FIG. 2E illustrates a schematic view of a radiotherapy system and a method of clinical application of the system.

Referring to FIG. 2E, the treatment planning system 800 forms the center of a method of treatment using radiosurgery system 10. In certain embodiments, the imaging module 400 of the system 10 includes an eye registration and imaging system 810. In certain embodiments, the eye-tracking system is configured to track patient movement, such as eye movement, for use by the treatment planning system 800. The eye-tracking system 810 can calculate a three-dimensional image of the patient's eye via physician inputs, and can include real-time tracking of movement of the patient's eye. The eye-tracking system obtains data that becomes a factor for determining radiotherapy treatment planning for a number of medical conditions relating to the eye, as described above. For example, the eye-tracking system may create an image of the posterior region of the patient's eye using the data it obtains. In certain embodiments, the data can be transferred via cable communication or other means, such as wireless means, to the processing module 140 of the radiotherapy treatment system 10. In certain embodiments, the processing module 140 may process data on the patient's eye and present an image of the patient's eye on the interface display 130. In certain embodiments, the interface display 130 may present a real-time image of the patient's eye, including movement of the eye.

In certain embodiments, the eye-tracking system obtains data on the patient's eye while the patient's face is placed approximately upright on and secured by the articulated head restraint 160 such that the patient's eyes face substantially forward, in the direction of the imaging module 400. In certain embodiments, the eye-tracking system may include an alignment system, adjustable using a joystick. The joystick can be tilted horizontally, vertically, or both horizontally and vertically, on a fixed base, in order to adjust the location and/or image displayed on the interface display 130 by the imaging module 400.

Another feature of the present disclosure is an integrated plan for treatment. The scale of the device as well as a limitation that the device treat a specific anatomy limits the scope of the treatment planning system which also allows for economies of scale. It is preferable that the x-ray beams be focused so that they apply radiation selectively to target regions of the eye and not to other regions of the eye to which high x-ray doses could be toxic. However, in some embodiments, the eye is the only anatomic region that is treated. In certain embodiments, the retina is the target for the ophthalmic treatment system; one or more beams would be directed to regions of the retina as they pass through the sclera. For treatment planning purposes, it is preferable to know the three-dimensional position of the eye and retina with respect to the output beam of the system. The treatment planning system incorporates detailed images and recreates the geometry of the eye and subsequently directs the x-ray system to manipulate the x-ray output so that the output beam points in the target direction. In some embodiments, the x-ray system is directed and moved automatically.

The treatment planning system 800 may utilize, or be coupled to, imaging systems such as, for example, optical coherence tomography systems (OCT), ultrasound imaging systems, CT scans, MRI, PET, slit lamps microscopy systems, direct visualization, analogue or digital photographs (collectively referred to as Biometry Measurements 820). In some embodiments, these systems are integrated into real-time feedback systems with the radiotherapy device such that second be second system updates of eye position and status can take place. Although relatively sophisticated, the system 800 may be limited to the ophthalmic region and therefore takes advantage of specific imaging equipment only available for the eye.

In some embodiments, the treatment planning system incorporates the entire soft tissue and bony structures of the head of a patient. The model incorporates all the anatomic structures so that obstructing anatomic regions can be excluded from the treatment. For example, the treatment plan incorporates the nose, the forehead, and associated skin and cartilage to dictate the directionality of the radiotherapy beam with respect to the eye. In some embodiments, these structures are related to the global coordinate system and aid in tracking and treating regions of the eye.

In some embodiments, the treatment planning system incorporates physical modeling techniques such as Monte Carlo (MC) simulation into the treatment plan so that the real time x-ray doses can be delivered to the ocular structures. In these embodiments, the inputs to the treatment planning system 800 are integrated with Monte Carlo simulation of the planned treatment plan and the effects of the plan, both therapeutic and potentially toxic, can be simulated in real time. In some embodiments, geometric ray tracing models are used with estimates based on prior Monte Carlo simulation. Ray tracing models with prior Monte Carlo support rapid and real time simulation of dosimetry.

The method depicted in FIG. 2E is as follows. Biometry measurements 820 and user controls 875 such as structure and dose are entered into the treatment planning system 800. Other inputs include information from an eye registration and imaging system 810. The output from the treatment planning system 800 consists of commands sent to the x-ray source and electromotive subsystem to move and position the source as well as to direct the on and off times (dose control) of the x-ray source 830. In some embodiments, maximum beam energy is set by the treatment planning system in order to create doses and plans for specific diseases. After a dose 840 is delivered, the treatment planning system 800 then signals x-ray source movement to deliver an additional dose 840. This cycle can iterate several times until the treatment is completed.

Figure 2F:
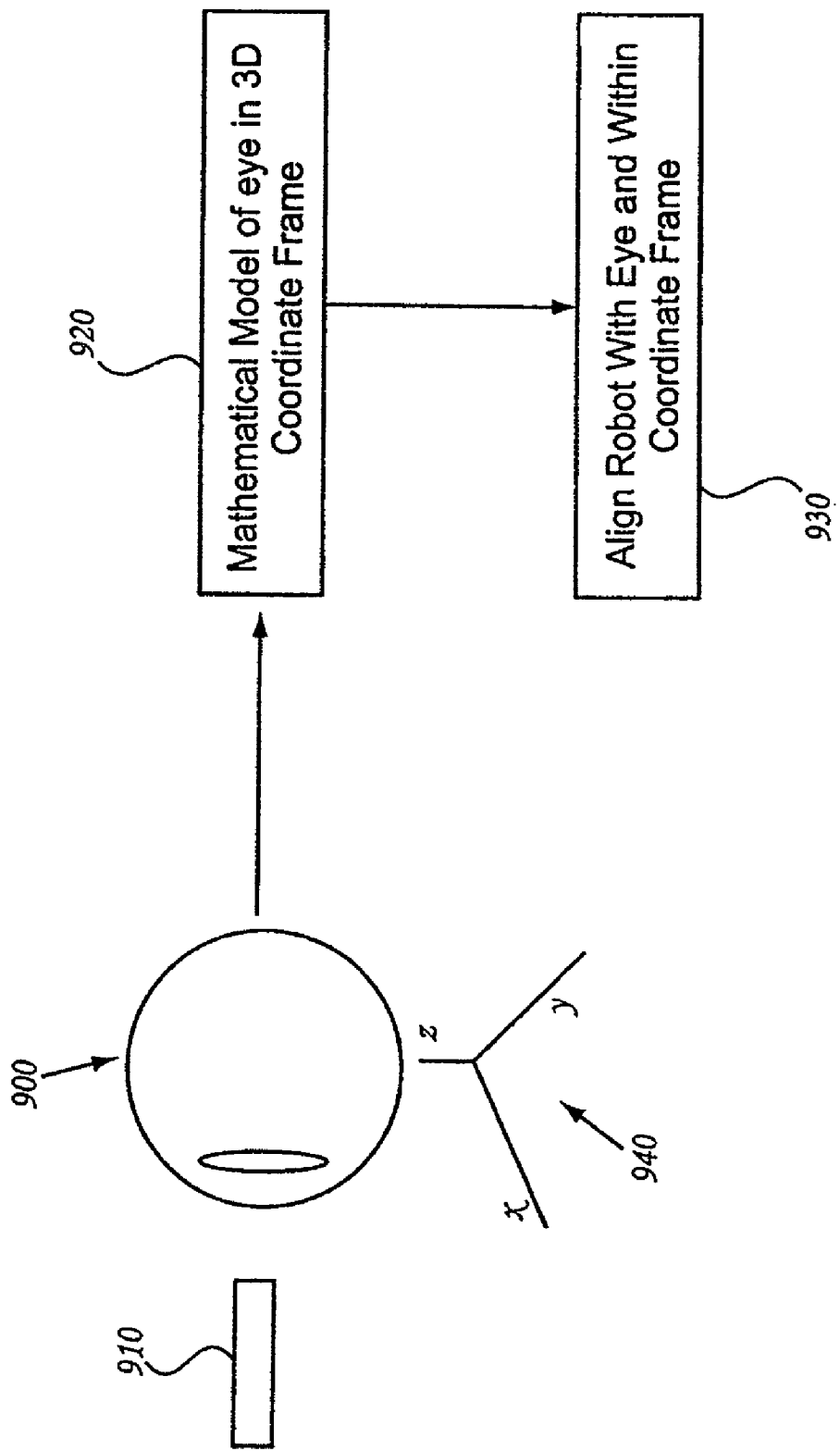
FIG. 2F depicts a procedural scenario for determining eye biometry and using it with systems described herein.

FIG. 2F depicts embodiments of the use of biometric measurements 910 to create an eye model and subsequently align a radiotherapy apparatus to the eye 900 within the coordinate reference frame 940. In some embodiments, an A-scan ultrasound 910 is used to obtain biometric data such as axial length, anterior chamber depth, and corneal thickness, which can then be combined with measured parameters such as white-white distance and/or corneal thickness, and then entered into a computerized model 920 that parameterizes the data and places the parameterized data into the coordinate reference frame 940. Subsequent to this step, the robot is placed within the same coordinate reference frame 930 as the eye.

Figure 2G:
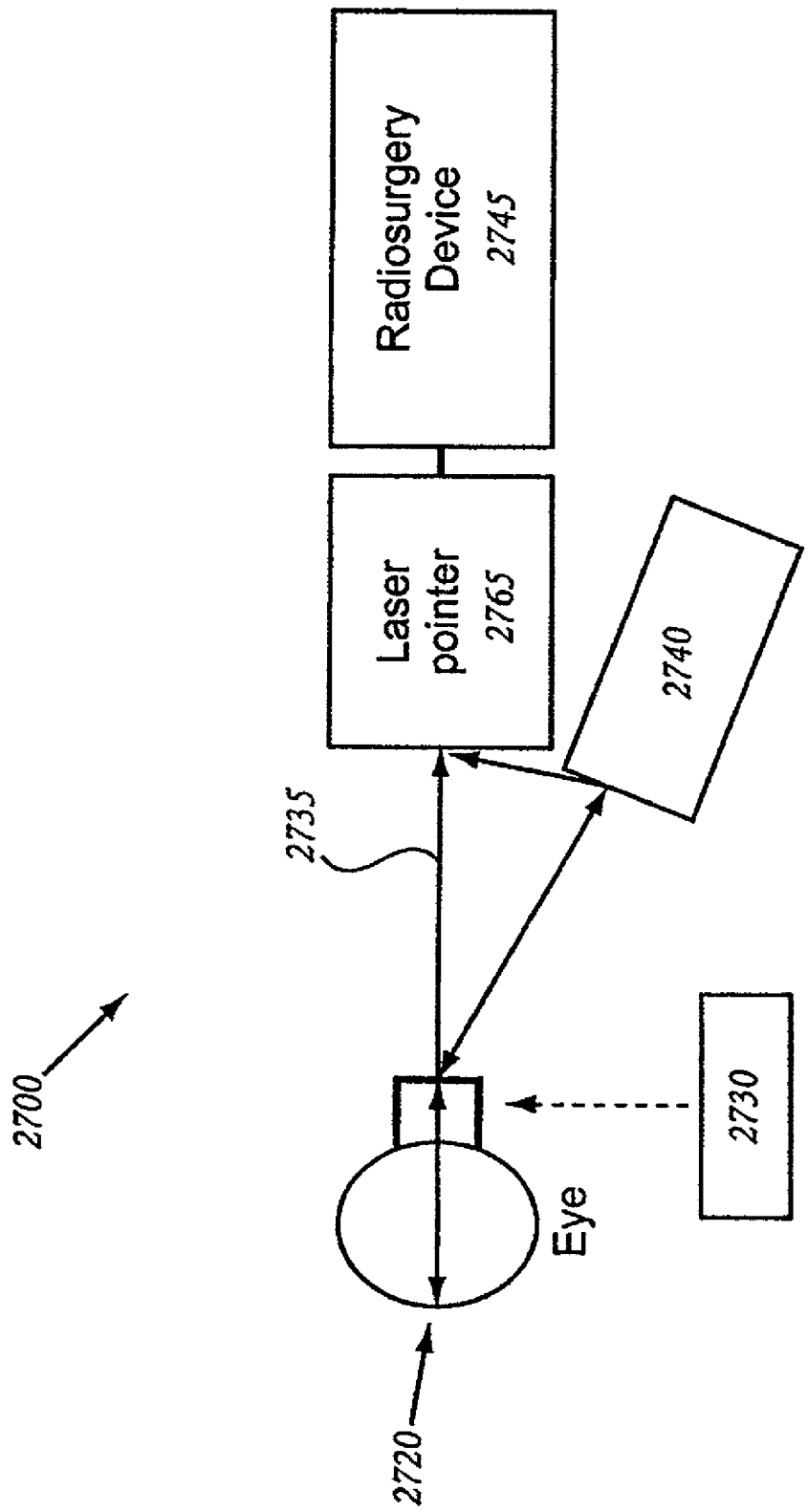
FIG. 2G depicts a schematic arrangement of embodiments of a radiotherapy system and alignment system.

FIG. 2G depicts an arrangement 2700 to align the radiosurgical device 2745. The goal of alignment is to align the output of the radiosurgical device 2745 and optionally the laser pointer 2765 with the treatment axis 2735 or any other defined axis of the eye. When the device 2745 is aligned with the treatment axis, the device 2745 is aligned approximately with a posterior pole 2720 of the eye. The posterior pole of the eye is approximately the position of the macula. In some embodiments, the collimator assembly is created so that the focused radiation is applied to the entire posterior pole 2720 including the extension of the treatment axis 2735 to the posterior pole 2720 as well as the macula. A camera 2740 is used to verify and/or maintain position of the combined radio-surgery and laser pointing device. The camera can base its verification on the eye contacting device 2730 or purely based on imaging of visible structures on the eye.

In some embodiments, the camera 2740 detects the laser pointer position and based on the position of the pointer on the target, the radiosurgical device is moved into an alternate position with the new laser pointer position used to verify the position.

Figure 2H:
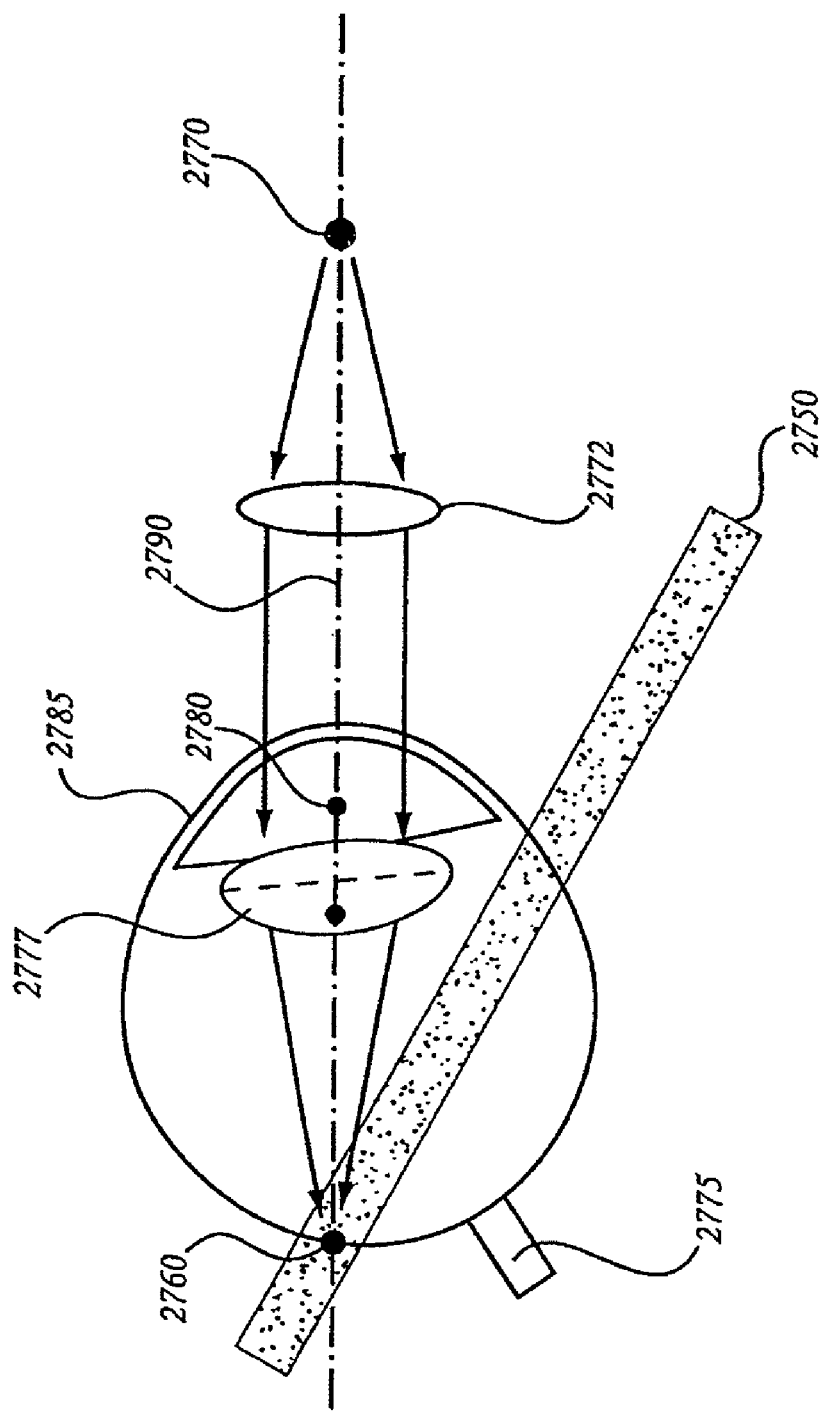
FIG. 2H depicts a schematic arrangement of embodiments that can be used to align a radiotherapy system with a visual axis of an eye.

In some embodiments, patient fixation (depicted in FIG. 2H) on a target is utilized to align the radiosurgical device to a visual axis 2790. The line of site between an object and the retina is directed to the fovea, located at the center of the macula, which is an area the radiotherapy systems described herein are configured to treat. In some embodiments, the patient is requested to fixate on an object so that the visual axis can be identified and the device aligned with this axis 2790. The patient fixes their eye on a fixation point 2770, which in some embodiments is a circular target. A line can be drawn between the object and the center of the pupil 2780 which, when projected toward the posterior pole of the eye, intersects the macula or fovea 2760. In one embodiment, the fixation point 2770 is the center of a circle so that a line through the center of the circle to the retina via the pupil center 2780 is the visual axis. A lens 2772 is used to collimate or align light from the fixation point 2770 so that the rays from the fixation point 2770 do not diverge and the central region of the fixation point 2770 can be used as the starting point for the visual axis. The visual axis 2790, then, by definition, becomes the treatment axis in this embodiment in place of the geometric axis in other embodiments. Once this line is defined in space, then the radiotherapy device can rotate about this imaginary line, delivering the radiation beam 2750 to the target tissue, which is depicted as the fovea. The beam 2750 from the radiotherapy device can then be placed at the proper angle to reach the macula 2760 yet avoid the cornea 2785, lens 2777, and optic nerve 2775.

For example, if a single beam can deliver the desired amount of radiation, the treatment planning system determines the direction of the x-ray beam relative to the patient specific anatomy and then the x-ray source is turned on. If two beams are desired to create the dose accumulation to the target, then the treatment planning system determines the size of the beams, their angles relative to the target and the specific patient anatomy, then applies the first beam to the eye in a first angle and a second beam at a second angle relative to the target. A similar method is used for three, four, five, or six beams.

Monte Carlo Simulation and Experimental Validation

Monte Carlo (MC) simulations are used to model x-ray absorption, scatter, and dosing to structures impinged on by x-rays. Monte Carlo methods are a widely used class of computational algorithms for simulating the behavior of various physical and mathematical systems, and for other computations. They are distinguished from other simulation methods (such as finite element modeling) by being stochastic, that is, non-deterministic in some manner. Monte Carlo simulation forms an integral part of all treatment planning systems and is used to assist in treatment planning where radiation is involved. Monte Carlo simulation can also be used to predict and dictate the feasibility and other elements of the radiotherapy system 10 (e.g., optimization of the collimator and treatment planning schemes); for example, the collimation designs, the energy levels, and the filtering regimes, can be predicted using Monte Carlo simulation. The designs predicted by Monte Carlo simulation should be experimentally verified and fine-tuned, but MC simulation can predict the initial specifications. In some embodiments of radiotherapy where the anatomy, beam energies, and treatment volume are similar, the Monte Carlo simulations can be run once and then the path variables altered (e.g., through ray tracing or other geometric methodology) without need to go back to Monte Carlo simulation.

In some embodiments, MC simulation is integrated into the treatment planning systems and in other embodiments, MC simulation dictates the algorithms used by the treatment planning system 800. MC simulation is often used in the back end of the treatment planning system to create boundaries of treatment. For example, MC simulation can predict the penumbra of an x-ray beam. The penumbra of the x-ray beam is used in the virtual world to direct the x-ray beam and set boundary limits for the x-ray beam with respect to the lens, optic nerve, etc.

In some embodiments, age-related macular degeneration (AMD) is the disease treated with the x-ray generation system. In some embodiments, the x-ray system 10 is used to treat post-surgical scarring in procedures such as laser photocoagulation and laser trabeculotomy or laser trabeculectomy. In some embodiments, the x-ray system is used to treat pterygia, ocular tumors or premalignant lesions such as hemangiomas and nevi. Importantly, the x-ray treatment system allows for selective irradiation of some regions and not others. In some embodiments, radiation is fractionated over a period of days, months, or weeks to allow for repair of tissues other than those which are pathologic or to be otherwise treated.

In order to 1) prove that lower energy radiation can be delivered to the retina to treat AMD in a clinically relevant time period with a device on the size scale in FIG. 1; 2) from a clinically relevant distance; and 3) optimize some of the parameters of the treatment system for initial design specifications for the x-ray tube, an MC simulation was performed.

Figure 5:
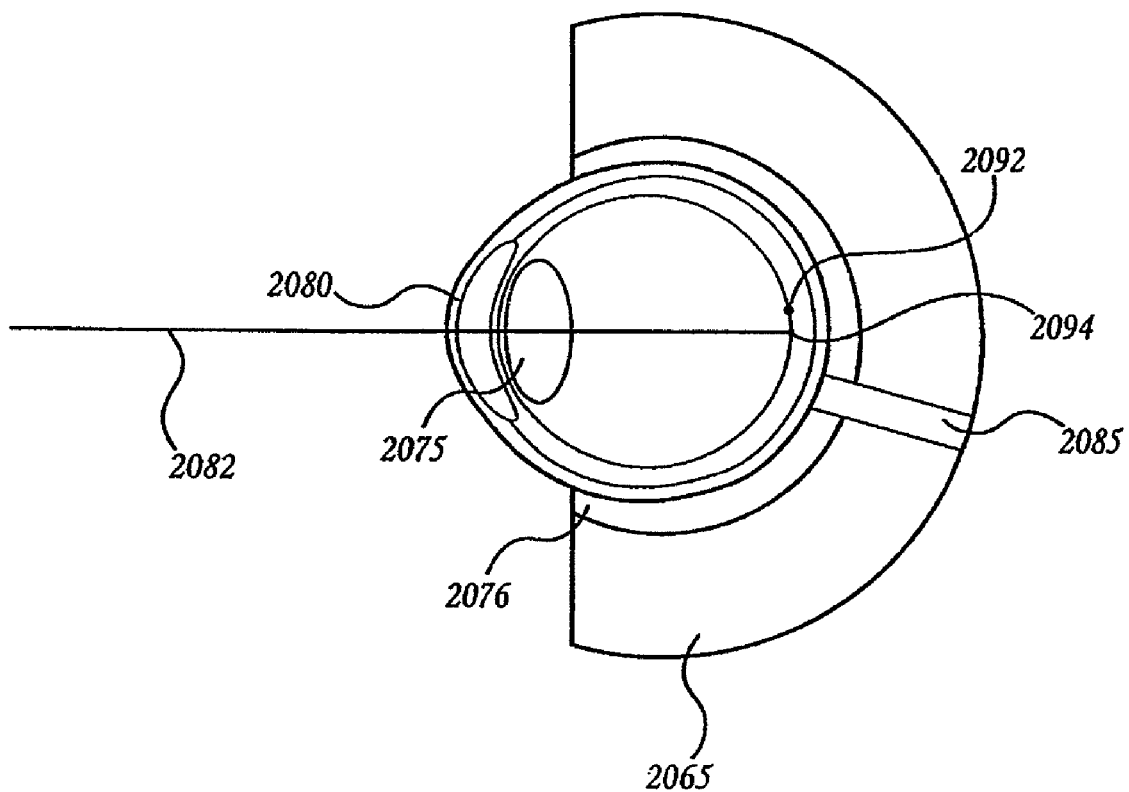
FIG. 5 illustrates a representative geometric model of the eye used for modeling purposes.
Figure 6:
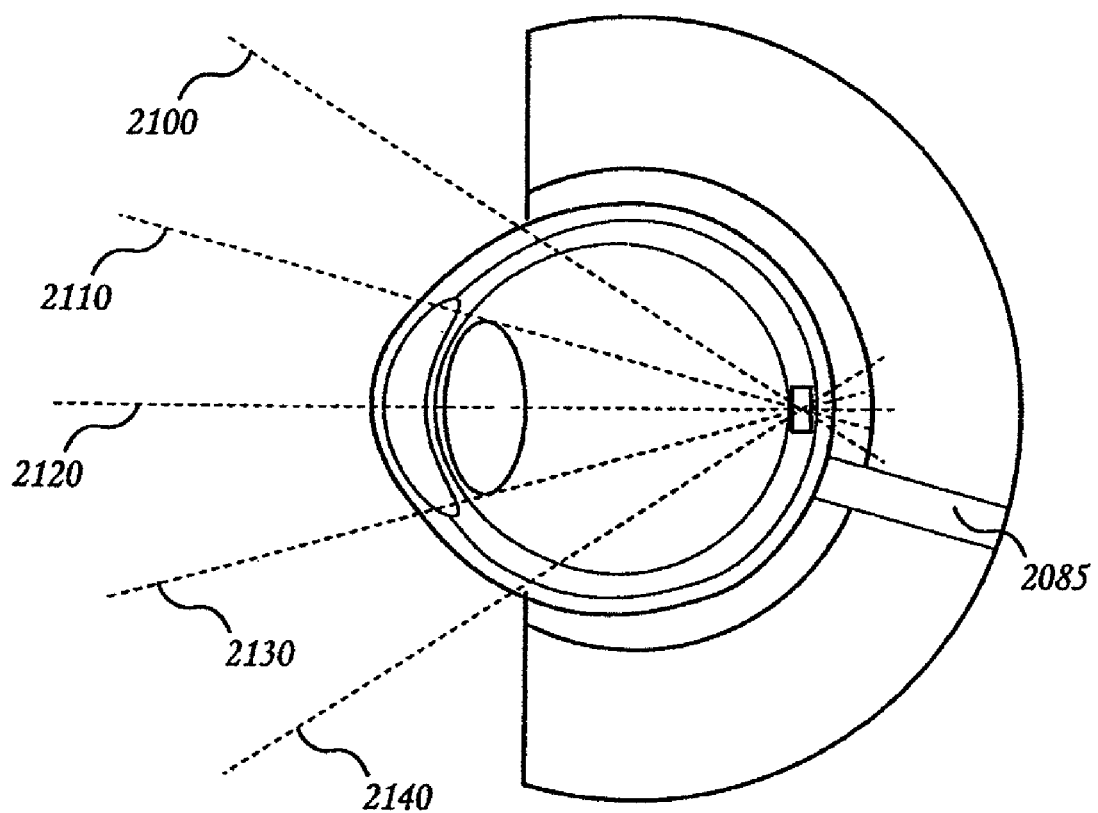
FIG. 6 illustrates representative beam angles with respect to an anterior surface and geometric axis of the eye.

Eye geometry was obtained and a two-dimensional, then three-dimensional virtual model created, as shown in FIG. 5. Soft tissue and hard tissue (e.g., bone 2065) was incorporated into the model in FIG. 5. Axis 2082 is the geometric axis, also termed the optical axis, of the eye. FIG. 6 depicts different beam angles (2100, 2110, 2120, 2130, 2140) with respect to the optical axis of the virtual eye which were modeled in this system to simulate therapy to the macular region to treat AMD in this example. In this simulation, each beam enters the eye at a different angle from the geometric central axis 2082. In this example, the geometric axis is assumed to be the treatment axis of the eye. Each beam cuts a different path through the eye and affects different structures, such as, for example, the macula 2094, optic nerve 2085, lens 2075, sclera 2076, cornea 2080, and fovea 2092 differently depending on the path through the eye. This modeling is used to determine the angle of radiation delivery of the radiotherapy device and is incorporated into the treatment planning algorithm. For example, in FIG. 6, beam 2120 enters the eye directly through the eye's geometric axis and beam 2100 enters through the pars plana. A series of x-ray energies were modeled using a range of energies from about 40 keV to about 80 keV. A proposed collimation scheme was used to produce a near parallel beam as was a series of different filters (about 1 mm to about 3 mm thickness aluminum). The combination of angle of entry of the beam, photon energy of the beam, and filtration of the beam all factor into the relative amounts of energy deposition to the various structures.

FIGS. 7A-7E depict some of the results from the MC simulation with the 80 keV energies showing that the x-ray beams can indeed penetrate through the sclera 2200 and to the retina 2250 with minimal scatter to other ocular structures such as the lens 2260 and the optic nerve 2085. The higher density of dots indicate actual x-ray photons in the MC simulation so that the relative absence of photons on the lens for example (FIG. 7A) in certain beam angles is indicative of lack of photon absorption at the level of the lens. These simulations reveal that low energy x-ray beams with widths up to 8.0 mm will substantially avoid critical structures of the anterior portion of the eye at certain angles off of the central axis. This modeling is incorporated into treatment planning for each patient and for each disease being treated.

Figure 7F:
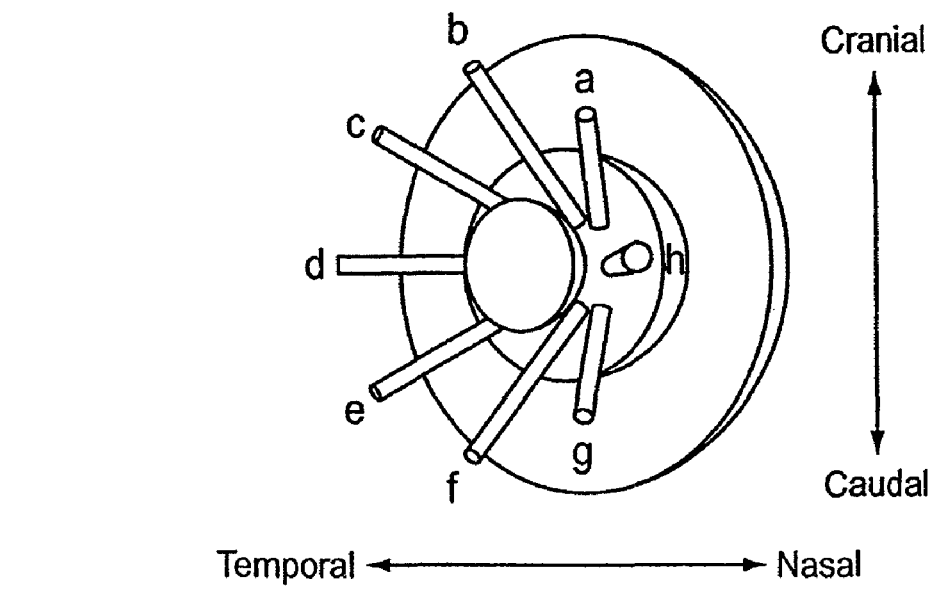
Figure 7F:
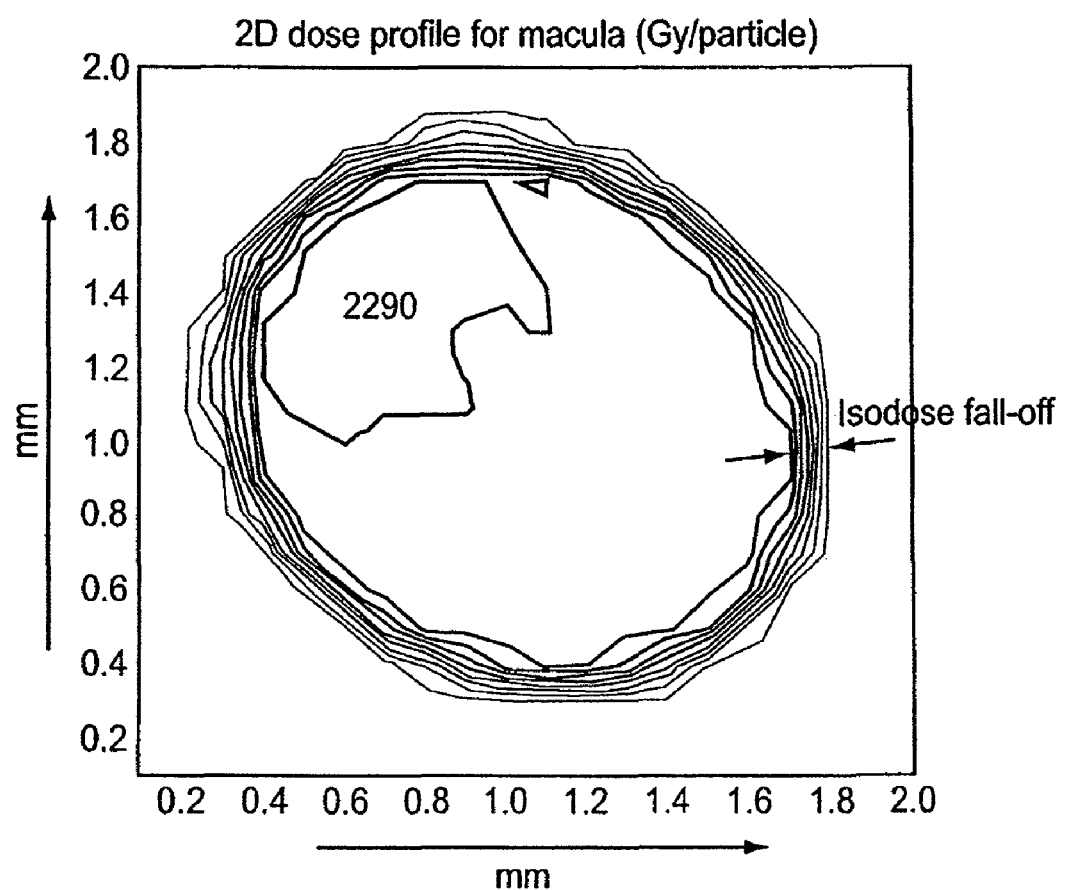

FIG. 7F (top picture) depicts the results of a simulation of a series of beams which enter the eye through the pars plana region. These angles are the clock angles (a-h; counterclockwise looking at the eye and their penetration through the eye affects the structures of the front part of the eye similarly but affect the structures which are asymmetric behind the eye (e.g., the optic nerve) differently. This simulation was done to plan how to minimize dose to the optic nerve while maximizing dose to the target regions and can be performed for each patient with varying geometries. In some embodiments, simulations are performed by directing the beam toward the eye through the pars plana direction and from various clock-face incident angles (a-h in FIG. 7F) which each correspond to varying nasal-temporal and caudal-cranial positions. In some embodiments, these beams are between about 2 mm and about 5 mm in cross-section, such as diameter, and have an energy of between about 60 keV and about 150 keV (also see FIG. 11H). Beams e, f, g, h, a which are generally directed from the inferior to superior direction and/or from the nasal to temporal direction, shown in FIG. 7F, have the most optimum profile with respect to the optic nerve 2085 and lens 2260.

In some embodiments, certain angles or directions are identified as corresponding to certain structures that are desirable to avoid during treatment. Consequently, the angles that correspond to these structures are not used for the trajectory of the x-ray during treatment, thus avoiding the optic nerve. For example, in some embodiments, the angle b (FIG. 7F) may correspond with an x-ray trajectory that would pass through the optic nerve 2085. In these embodiments, the angle b may not be used to reduce the likelihood of exposing the optic nerve to the x-ray. Accordingly, the angles can be used to optimize the treatment plan and present as little risk as possible to existing structures that are sensitive to radiation. FIG. 7F depicts eight trajectory angles. In some embodiments, the x-ray trajectory can include less than eight or more than eight trajectory angles. For example, in some embodiments, four, six, ten, or twelve trajectory angles are presented. In these embodiments, optimal beam directions are provided by those beams (e.g., b, a, g, h, f) which are considered to come from the nasal direction. Beam entry angle on the sclera and its transmission to the retina are chosen by the treatment plan and are used to optimize radiotherapy to target structures by the treatment planning system.

The lower picture in FIG. 7F shows the dose on the retina of one of the angled beams in the picture above. The predicted isodose fall-off for these beams is greater than about 90% within about 0.05 mm to about 0.1 mm of about a 1 mm to about a 2 mm beam which is less than ten percent greater than the 100% isodose region. Region 2290 depicts a region of higher dose within the iso-dose profile. This higher dose region 2290 results from the fact that the beam enters the eye at an angle. The increase in the dose is moderate at approximately ten to twenty percent higher than the average for the entire region. Furthermore, because there are multiple beams entering the eye, the areas of increased dose 2290 average out over the region of the retina. Therefore the higher dose region is incorporated into the treatment plan to account for the uneven distribution.

Figure 8:
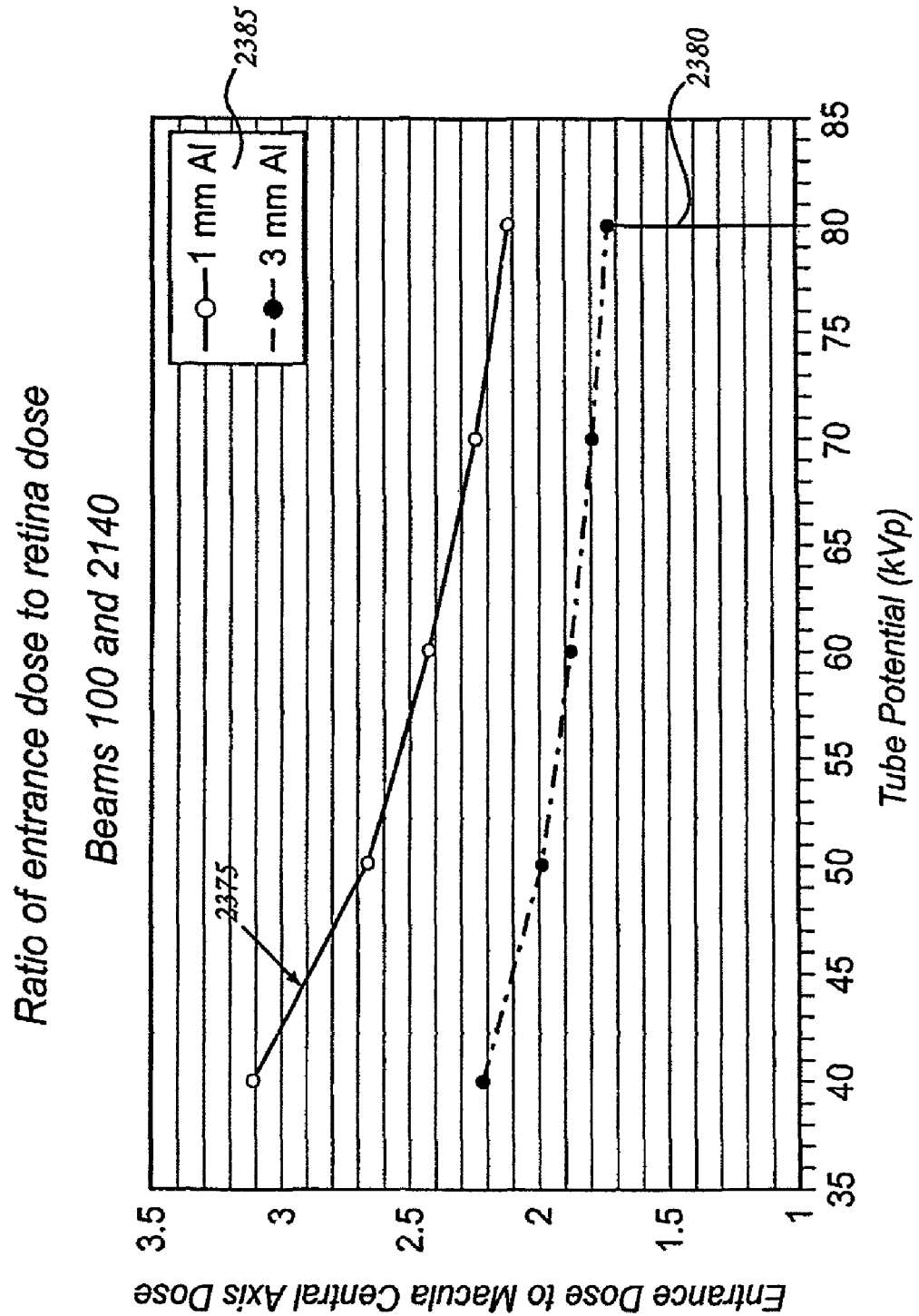
FIG. 8 depicts results of Monte Carlo simulations performed to analyze the effect of different energies and doses on the structures of an eye.

FIG. 8 is a quantitative, graphical representation of the data in FIGS. 7A-7E. What is shown is the surface to retina dose for different x-ray tube potentials and for different aluminum filter thicknesses 2385. This graph is the data for beams 2100 and 2140 in FIG. 6. The ratio of surface to retina dose is shown in FIG. 8 (i.e., the dose of entry at the sclera to the dose at the retina); what can be seen is that the dose to the sclera is not more than 3 times the dose to the retina for most beam energies (tube potentials). For energies greater than about 40 kVp, the ratio of surface dose to retina dose 2375 is less than about 3:1. What this says is that if the spot were maintained in the same position as about 25 Gy was delivered to the retina, the maximum dose to the sclera would be about 75 Gy. Of course, as the beam is moved around the eye, the about 75 Gy is averaged over an area and becomes much less than the dose of about 25 Gy to the macula. This is depicted in FIG. 6 which shows the results of the movement to different points along the sclera with the x-ray beam. At 80 keV 2380, the ratio of surface to depth dose is closer to about 2.2 with about 1 mm of filtering. These data are integrated into the treatment plan and the design of system 10 and, in part, determine the time and potential of the x-ray tube. The surface-depth dose of the beam is also integral in determining the treatment energy levels and corresponding tube potentials for various disease treatment and is therefore incorporated into the treatment planning system.

Therefore, in some embodiments, tightly collimated x-ray radiation at energy levels greater than about 40 keV with greater than about 1 mm of filtration delivered through the pars plana region of the eye can be used to deliver a therapeutic dose of radiation to the retina with a relatively lower dose buildup on the sclera, the lens, or the optic nerve than the therapeutic dose delivered to the retina. For example, if a therapeutic dose to the retina is about 25 Gy or less, the dose to any region of the sclera penetrated by the beam will be less than about 25 Gy.

Figure 9:
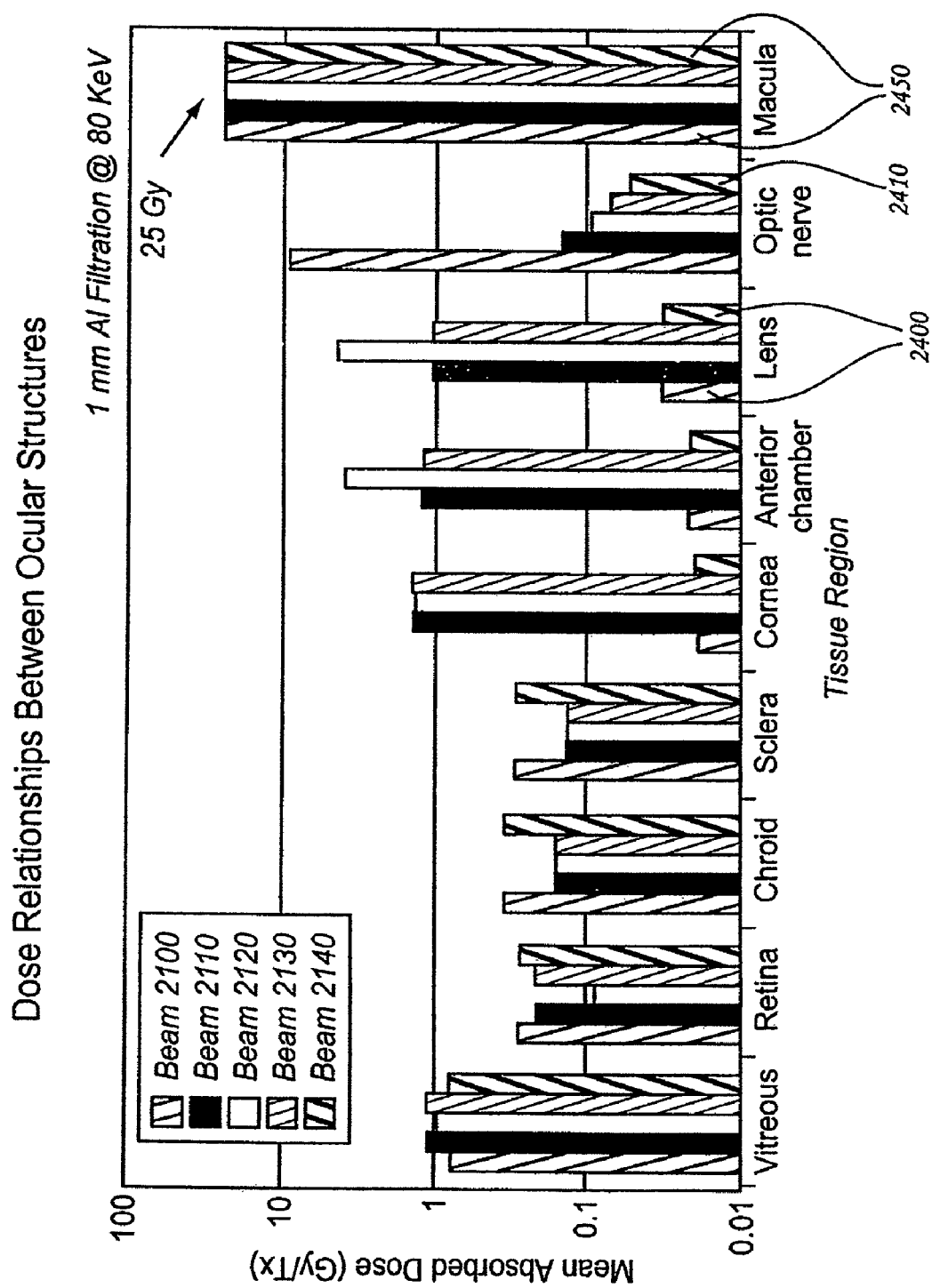
FIG. 9 depicts results of Monte Carlo simulations performed to analyze the effect of various treatment regimes on the various structures of the eye.

FIG. 9 is a bar graph representation showing scatter doses to ophthalmic regions other than the retina and comparing them to the retina. As can be seen in the logarithmic figure, the dose to the lens 2400 (beams 2100 and 2140) and optic nerve 2410 (beam 2140 alone), the two most sensitive structures in the eye, are at least an order of magnitude lower than the dose delivered to the macular region 2450 of the retina. Other beam angles result in distinctly higher doses to these structures. Therefore, a 25 Gy dose of radiation can be delivered to a region of the retina through the pars plana region of the eye with at least an order of magnitude less radiation reaching other structures of the eye such as the lens, the sclera, the choroids, and so forth. These simulations dictate the design specifications for the x-ray generation systems and subsystems. These simulations can also be integrated into the treatment planning system 800 as a component of the plan so that doses to therapeutic targets are higher than doses to critical structures. For example, the planning system, which incorporates the unique anatomy of each patient, can simulate the amount of radiation delivered to each structure dependent on the angle and position of delivery through the sclera. Depending on the angle, beam size, and beam energy, the radiation delivered to the ocular structures will vary and alternative direction can be chosen if the x-ray dose is too high to the structures such as the lens and the optic nerve.

Figure 10:
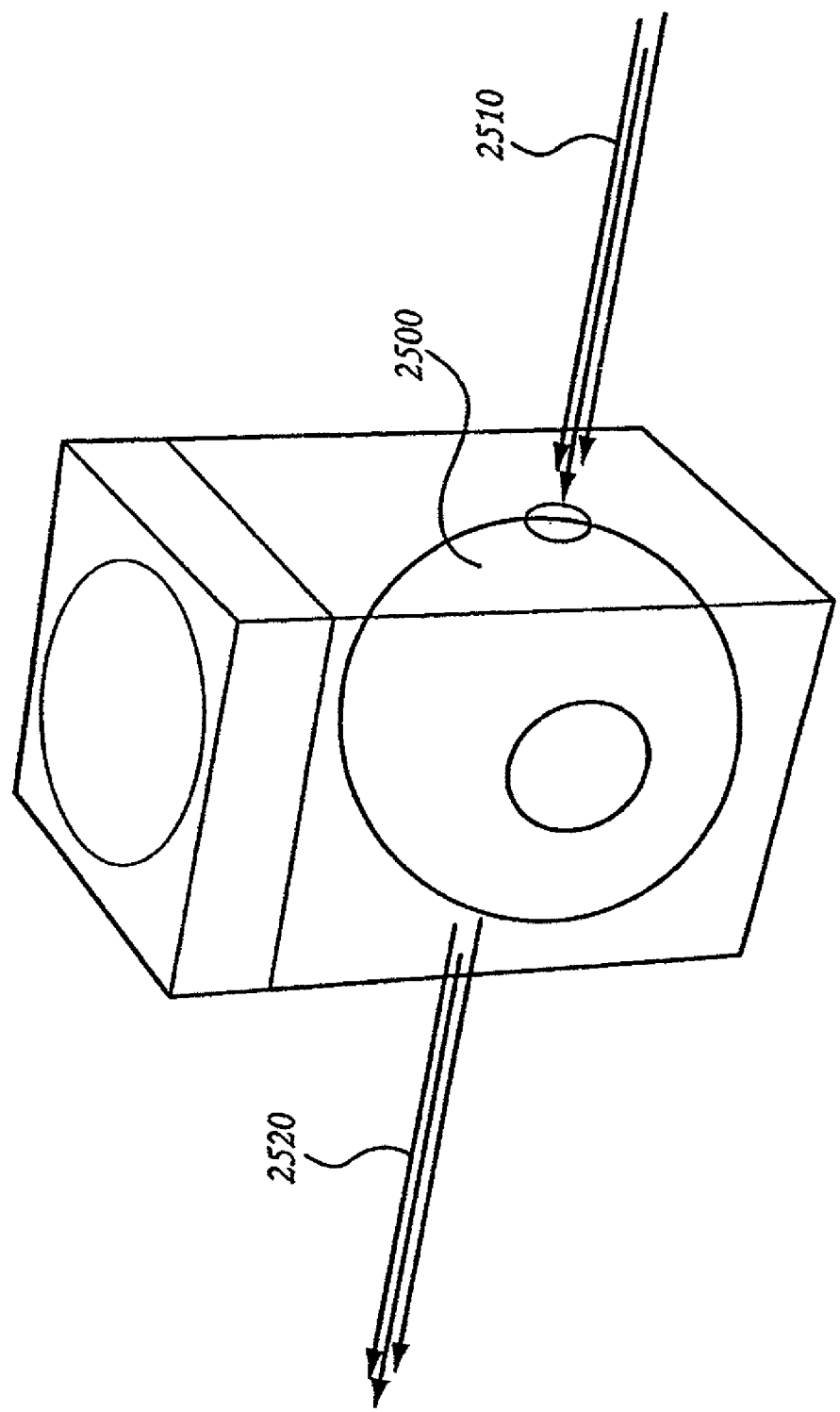
FIG. 10 depicts experimental results of thin x-ray beams traveling through a human eye to validate a Monte Carlo simulation model.

With reference to FIG. 10, to verify the validity of the MC simulations and verify that the eye can be assumed to be a sphere of water, a human cadaver eye 2500 was obtained and the ratio of surface to depth dose of an x-ray source was experimentally determined. Among other things, parameters of an emitted x-ray beam 2510 were compared with parameters of the beam 2520 emerging from the eye 2500. The ratio from the experimental set-up in FIG. 10 proved to be identical to that when the eye is assumed to be water in the MC simulations. For example, the ratio of surface to 2 cm depth for 80 keV with 2 mm filtration was indeed 3:1 as predicted by the MC model. Additional work verified that the dose fall off at each depth was likewise identical. This experimental work confirms that the modeling predictions using MC are accurate for ocular structures and that secondary interactions typically required of MC simulations with high energy x-rays are not necessary for lower energy x-rays. These observations significantly simplify the MC simulations and allow for quick real time simulations at the time of treatment planning using geometric relationships and predicted beam divergence. Furthermore, the design criteria which are used in the system 10 design can be accurately modeled using water for their prediction rather than the time and expense involved in obtaining human tissue.

Further analysis and experimentation reveals that to deliver 25 Gy to the macula in a clinically relevant time period (e.g., not longer than 30 minutes), the system in FIG. 1 will draw about 1 mA to about 40 mA of current through the x-ray source. The exact number of mA depends on how close the x-ray tube is to the eye and the maximum spectral energy (e.g., about 50 keV) delivered which is also dependent on the maximum penetration depth desired. These parameters are integrated into a treatment plan which is used by the operator of the system to set the system parameters. If the tube is very close to the eye a low degree of penetration is desired, then the system will draw less current than if the system is further away from the eye. In some embodiments, it may be that the about 15 Gy to about 25 Gy needs to be delivered to the retina in a period shorter than 10 minutes. In such embodiments, the tube current may need to be upwards of 25 mA and the x-ray tube closer than 25 cm from the retina. These parameters are for energies of about 60 to about 100 keV and from about 1 mm to about 3 mm filtration with aluminum, lead, tungsten, or another x-ray absorbing metal. In certain embodiments, the collimator is less than about 5 cm from the anterior surface of the eye and the photon energy is about 100 keV with 1, 2, 3, 4, or 5 beams with diameters of between about 1 mm and about 6 mm entering the eye through the infero-nasal region. The nasal region affords the greatest distance from the optic nerve and the inferior region is preferred so as to avoid the bones of the nose and the anterior skull. These assumptions are for an eye which is positioned to look straight outward from the skull. In this embodiment, the treatment time may be less than about 5 minutes within a range of currents between about 15 mA and about 40 mA. Each beam of the 1-4 beams can be turned on for between about 3 seconds and about 5 minutes. In some embodiments, 3 beams are used for the treatment. In some embodiments, the collimator is placed within about 3 cm from the surface of the eye, and in some embodiments, the collimator is placed within about 10 cm of the surface of the eye.

Figure 11B:
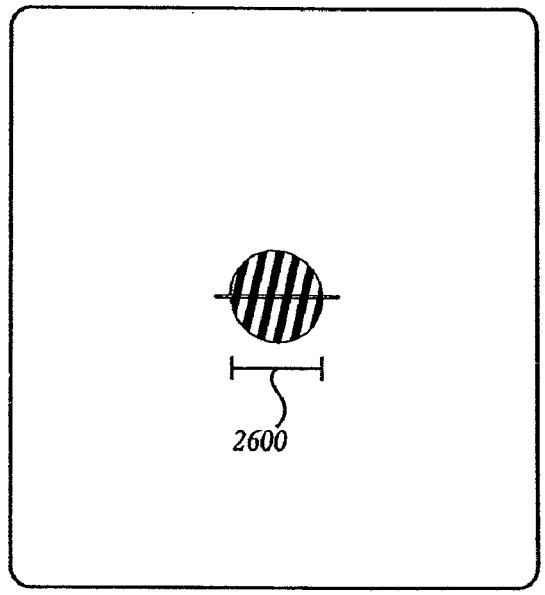
FIGS. 11A$^1$-11B depict results of thin x-ray beams penetrating through an eye model.
FIGS. 11C-11G depict embodiments of a treatment plan based on theoretic and experimental data.
FIGS. 11H-11I depict images of radiation beams, in which orthovoltage radiation beams as described herein are compared to other radiation beams.
FIG. 11J depicts results of an experiment in which three beams were focused on the back of an eye using a robotic system.
Figure 11B:
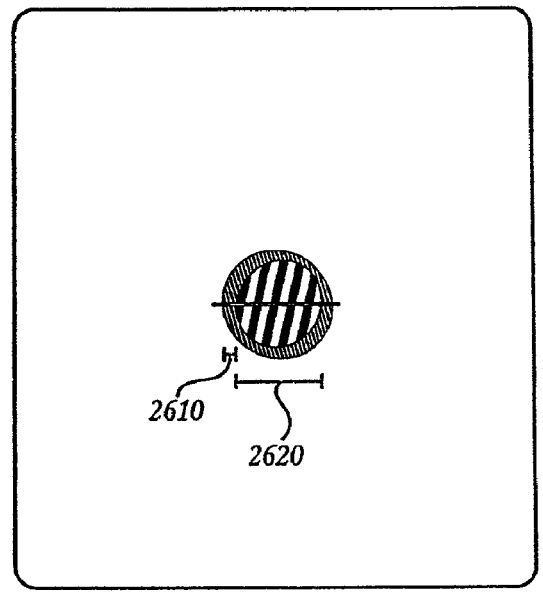
Figure 11B:
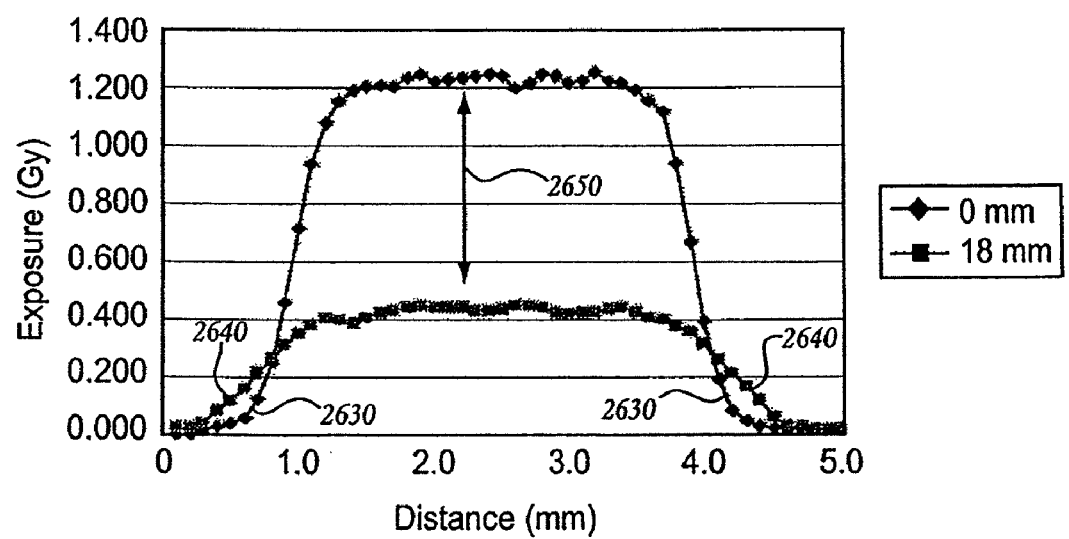

FIG. $11A^1$ depicts the results of a single collimated x-ray beam 2600 and FIG. $11A^2$ depicts the beam 2620 after it has penetrated through approximately 2 cm of water (an eye); the shaping collimator is approximately 5.0 cm from the surface of the water. As can be seen in FIG. $11A^2$, there is a small penumbra width 2610 about an original beam width 2620 after penetration through the eye which is less than 10% of the shaping beam shown in FIG. $11A^1$. These data incorporate both divergence as well as isodose drop off from scatter and reveal that for a collimator within about 10 cm of the target, the penumbra can be very small. The beam energy in this example is approximately 80 keV. FIG. 11B depicts a graphical representation of the penumbra from measurements within an x-ray detection film. Delta 2650 represents the absorption in the energy between the surface and the depth as recorded by x-ray sensitive film. The tails seen in 2640 versus 2630 indicate a small degree of penumbra effect as the beam loses energy through the eye. Indeed, the penumbra for a 0.5 mm to 6 mm spot size can be as low as about 0.01% and as high as about ten percent depending on the placement of the collimators with respect to the target.

Figure 11D:
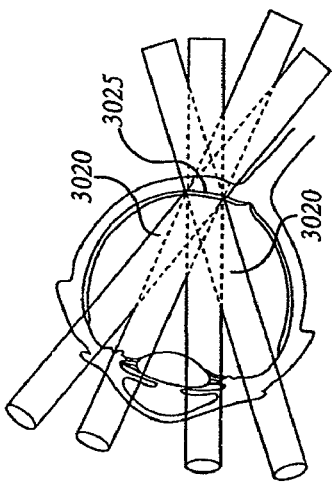
Figure 11C:
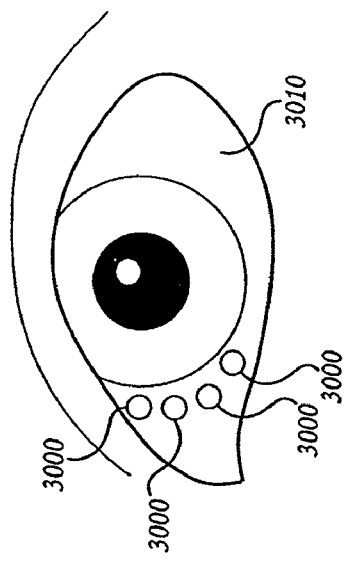

FIGS. 11C-11G depict simulations of the summation of the beams as described above. The simulation was accomplished using Monte Carlo simulation based on the device parameters discussed above, which created the experimentally verified single beam profiles shown in FIGS. $11A^1$ and $11A^2$. Alternatively, the beams can be created using ray tracing geometries or geometric models of beams which are verified by the Monte Carlo simulation such that the error between the ray tracing and the Monte Carlo simulation is relatively constant given that beams travel through a similar amount of tissue with minor changes to beam width, beam energy, and amount of tissue through which the beam travels. In FIGS. 11C-11D, radiosurgical beams are depicted on an anterior portion of the eye in some embodiments of a method of delivery of radiosurgical beams. In FIG. 11C, traversal zones 3000 on the sclera 3010 of an eye are depicted where radiosurgical beams are depicted traversing, or intersecting, the sclera 3010. Because the scatter and isodose fall of these beams are known to be low (e.g., within 10%), these beams can be placed within one beam diameter of one another without substantial overlap.

The angles of the beams with respect to the center of the posterior pole and the macular regions are determined by the eye model and treatment plan. FIG. 11D depicts a saggital view of the beams depicted in FIG. 11C with the radiosurgical beams 3020 extending through the sclera and converging at the macula region 3025. Radiosurgical beams 3020 can be placed as little as about 100 microns apart and as far apart as about 2 mm or about 3 mm depending on the target region to be treated. Beams 3000 enter the sclera from the inferior or nasal region of the eye Furthermore, it is now known based on modeling data, that the beams 3020 can be placed about 50 microns to about 500 microns apart from one another at the target region without appreciable build up of dose on structures such as the lens, the sclera, and the optic nerve. It is also known from the modeling and experimentation that to deliver a dose of greater than about, for example, 20 Gy to a target region of the retina, greater than 1 beam can be advantageous, with treatment plans including up to and beyond about 5 beams for delivering the desired radiation dose.

As described above, the surface to depth ratio of the beam to target is a factor in planning delivery of the dose. In the case of radiosurgical beams with energies in the 100 keV range, the surface to target dose can be as low as about 2:1 or up to about 5:1. Within these ranges of energies and surface-to-target ratios, any particular region of the sclera will not receive an unacceptable dose of radiation. For example, with 4 beams and 24 Gy to the retina (6 Gy per beam) the dose to each individual region on the sclera is approximately 15 Gy, a dose that has been determined to be well tolerated by the sclera. Indeed doses of up to 40 Gy can be tolerated well by the sclera. As shown by Pajic and Grener (Long-term results of non-surgical, exclusive strontium-/yttrium-90 beta-irradiation of pterygia; Radiation and Oncology 74 (2005) 25-29), doses up to even 50 Gy on the sclera is not harmful even up to 10 years later in young patients. In this case, 50 Gy could be delivered to a single point on the sclera and 18-24 Gy delivered to the macular region. Such a therapeutic regimen might then require only beam.

Figure 11G:
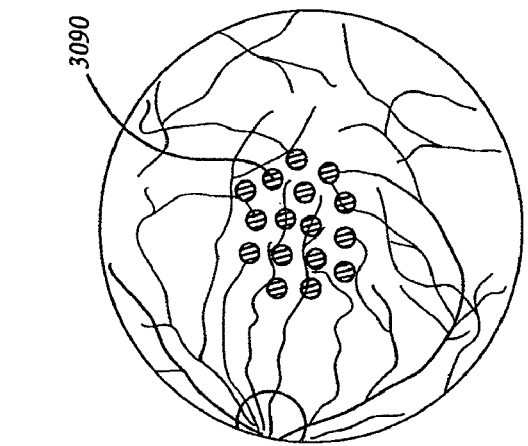
Figure 11F:
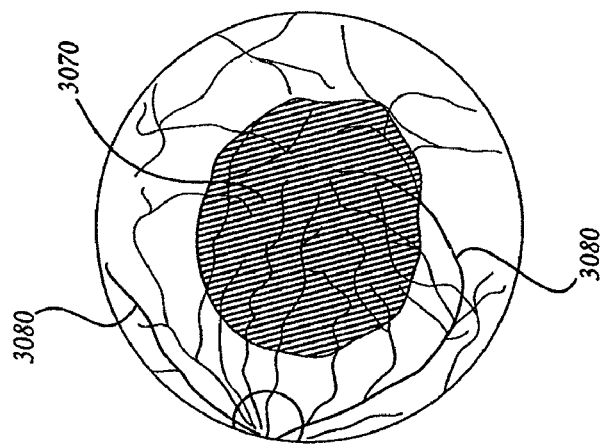
Figure 11E:
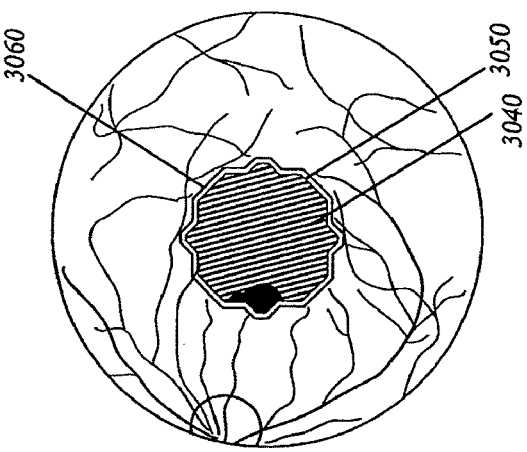

FIG. 11E depicts a summation of the beams 3040 on the retina, and specifically the macula in this example. Notably, the fall-off in penumbra 3050 is very rapid at about 98% by a few millimeters from the edge 3060 of the beam.

FIG. 11F depicts embodiments of a summated beam in which an oblong shape is created by collimators custom shaped to create a flared type of radiosurgical spot 3070 on the region between the vascular arcades 3080 which covers the macula.

FIG. 11G depicts embodiments of a target region in which there is a checkered appearance 3090 of the dose (microfractionation) caused by passage through a collimator with multiple separate holes or collimated regions. Such "microfractionation" can allow for improved therapy to the target region with reduced side effects. To the extent that side effects are mediated by effects on the vasculature underlying the retina, by limiting the amount of radiation to these blood vessels and allowing for local collateralization around each microfraction, the retinal vasculature can be spared without sacrificing therapeutic effect. In some embodiments, origination of the neovascularization of the region is identified and incorporated into the treatment plan. In such embodiments, the radiation dose can be focused at this region to stop vascularization of the region. In some embodiments, a halo or annular treatment region is identified and treated to stop or reduce vascularization into a center portion of the halo or annular region.

Figure 11H:
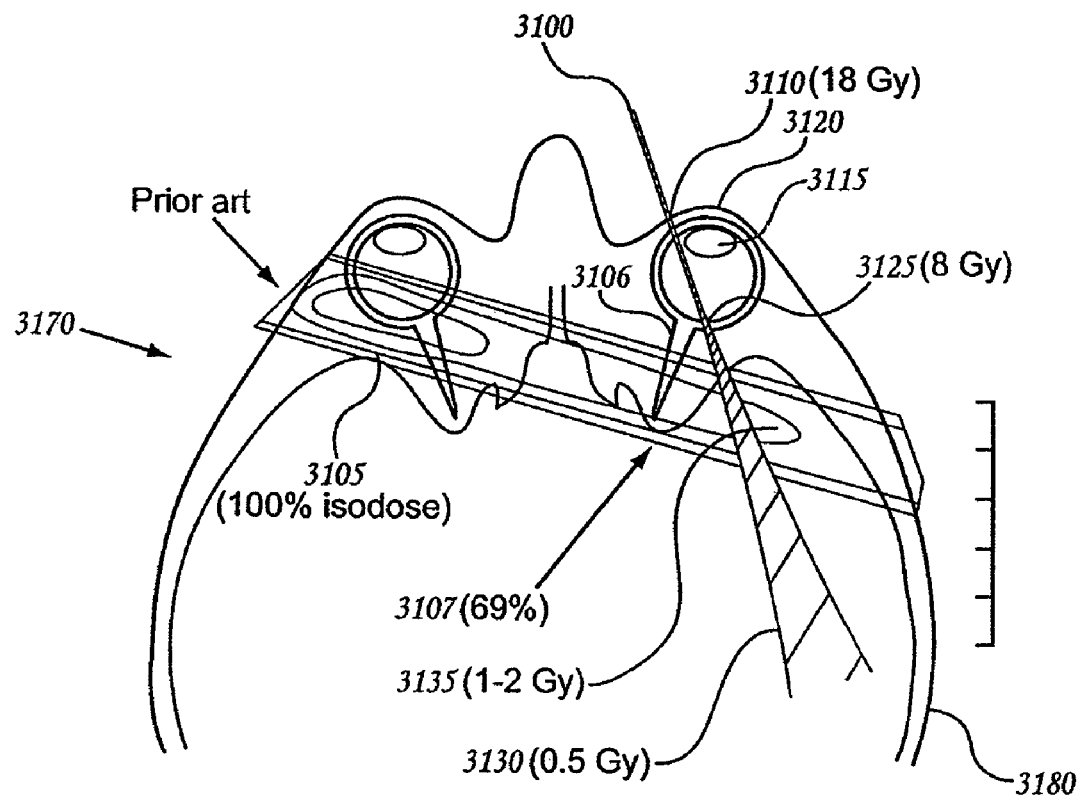

FIG. 11H depicts a comparison on a brain CT 3170 between a finely collimated orthovoltage radiosurgery beam 3100 and a prior art treatment beam 3105 in what has been attempted in the past (Marcus, et. al., *Radiotherapy for recurrent choroidal neovascularization complicating age-related macular degeneration*; Br. J. Opthalmology, 2004; 88 pps., 114-119). In the prior art treatment beam 3105, large linear accelerators were used without localization or customization specifically for the eye. The prior treatment beam path 3105 depicts the isodose calculations on the CT scan 3170. The figure depicts that the 90-100% isodose volumes emcompass the ipsiliateral entire optic nerve and retina. Even the contralateral optic nerve 3106 received 63% 3107 of the dose. As a result, the treatments performed in Marcus et. al. required fractionation of the dose over many days and with small fractions in order to prevent damage to normal tissues. Such fractionation and minimalist dosing and planning schemes likely lead to the lack of efficacy in those studies. In addition, these prior art attempt at applying radiation to the macula did not consider eye movements or eye position.

In contrast, the beam path 3100 of a finely collimated orthovoltage beam is also depicted. This experimentally and theoretically verified microcollimated 100 keV beam enters the sclera in the pars plana region 3110 delivering 18 Gy to the sclera and completely misses the optic nerve 3106, the lens 3115, and the cornea 3120, and delivering a therapeutic dose of 8 Gy to the macular region 3125. Thereafter, in the brain, the radiation is scattered by the bone behind the eye to 1-2 Gy 3135 and quickly attenuates to 0.5 Gy 3130 in the brain tissue and the bone of the skull 3180. With three of these beams at different clock angles on the eye, the summation on the macula will be 24 Gy, with only 18 Gy to the sclera at three different entry points on the sclera.

Figure 11I:
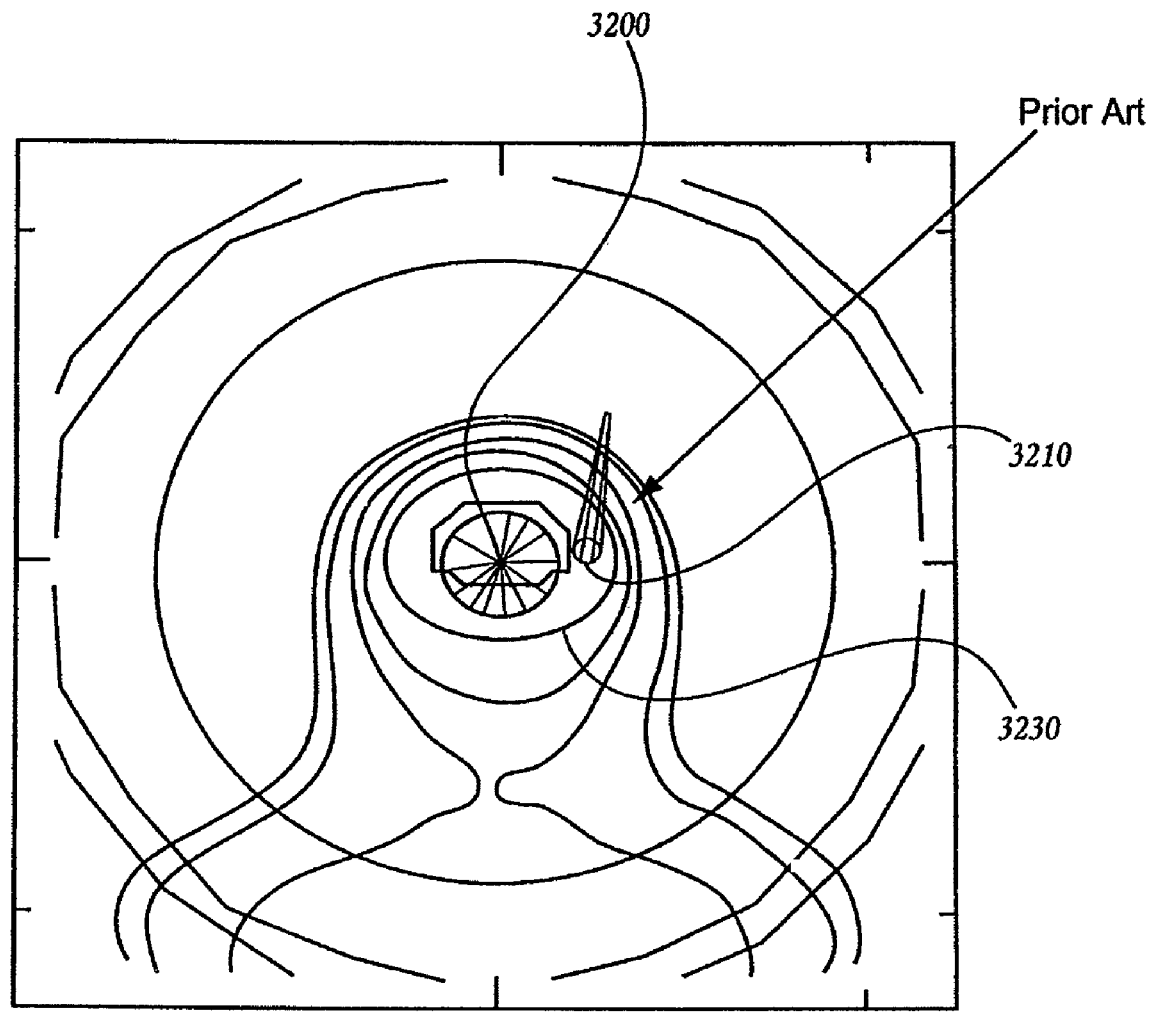
Figure 11J:
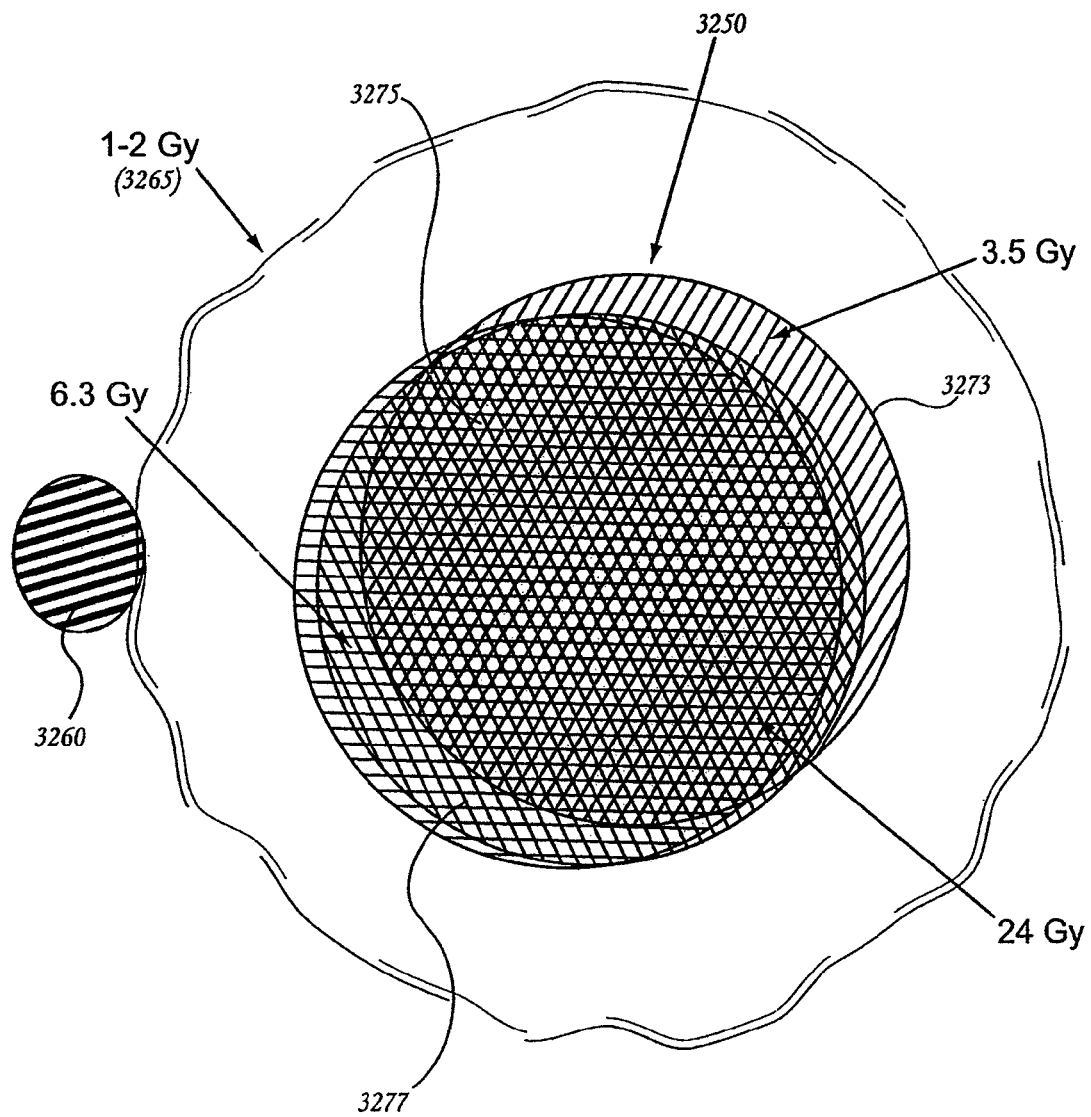

FIG. 11I similarly depicts prior art treatment beams (Adams, J. et. al; Medical Dosimetry 24 (4) 233-238). In this study, a proton beam study, the 90% isodose line 3230 encompasses the optic nerve 3210 and the macula 3200. In addition, eye location and movement were not controlled in this study. The authors of this study reported significant complications, likely due to the very broad coverage of the retina with 20-24 Gy of proton beam radiation in 12 Gy fractions. Such complications likely negated any benefit of the therapy. The x-ray delivery described herein allows for delivery only to the macula where the disease exists while limiting or avoiding delivery of x-rays to other regions that are not diseased, FIG. 11J depicts a schematic of radiochromic film after benchtop delivery of 100 keV overlapping x-rays at a target site 3250. The region of overlapping x-ray beams 3275 are shown at their overlap region where the dose is 24 Gy. The optic nerve 3260 is depicted lateral to the overlapping set of beams at a scaled distance from the center of the overlap. A rapid isodose fall off 3273, 3277 occurs lateral to the overlapping region 3275 and well away from the optic nerve 3260. Notably, the isodose depicted at region 3265 is indeed between about 1% and about 10% of the dose (0.24 Gy-2.4 Gy) at the treatment spot 3275. These data are a consequence of the overlapping beam geometry as well as the fine beam collimation; they are physical proof of the ability of finely collimated overlapping orthovoltage x-ray beams to create well-defined treatment regions. Due to the 10-100 fold difference in treatment dose to optic nerve dose, fractionation is not required, and the entire dose can be given to the treatment region in one session with minimal concern for injury to important structures, such as the optic nerve. These overlap regions can be optimized and/or placed anywhere within the eye which is determined by the treatment planning system and depends on the beam energies, collimation, and filtering. The degree of overlap is also to an extent determined by system parameters. For example, treatment of the entire region of the retina for macular degeneration may be different than that for tumors or for hemangioma.

These modeling techniques, parameters, and imaging system described above allow for an integrated system to be devised and developed. Some embodiments are depicted in FIG. 12A in which a five degree of freedom positioning stage is used so as to produce the desired beam angles to deliver radiosurgery to the retina. The collimator 3315 is positioned close to the eye of the patient 3330, so as to allow for an acceptable penumbra as well as a tightly collimated radiation beam as described above. The collimator is typically between about 1 mm and about 4 mm so that the spot size on the back of the retina is approximately about 4 mm to about 7 mm. Laser pointer 3225 travels through a beam splitter and exits the collimator with its center aligned with the radiation beam. Region 3335 is the space through which the device can move. The space can be planned based on imaging performed on the patient. The space is a small region which allows for simplification of the motion system moving the x-ray source 3325. The system 3300 also contains a hose system 3310, 3345 to deliver cooling fluid into and from the x-ray tube 3325.

Figure 12B:
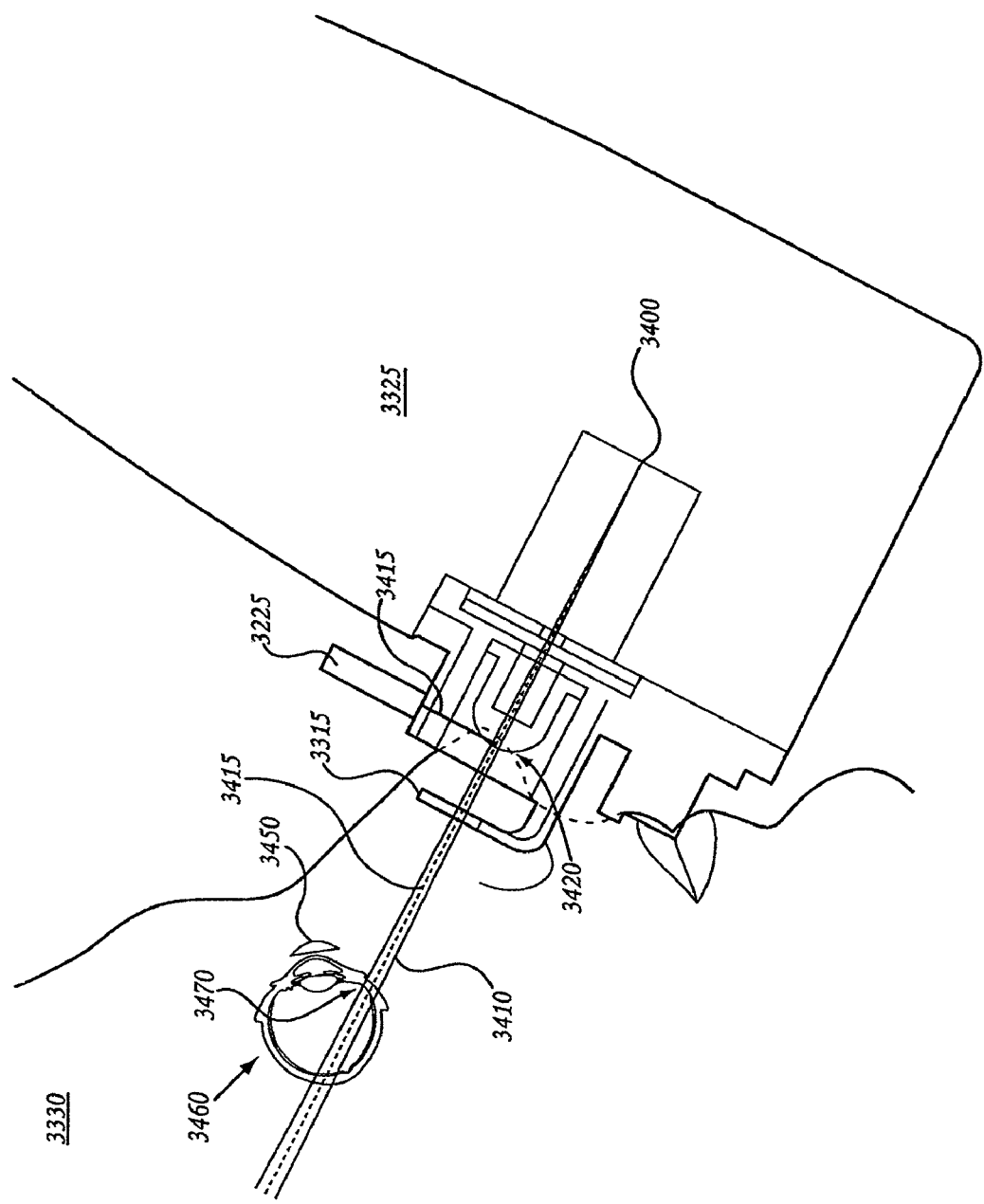

FIG. 12B depicts a cross-section schematic view of the system 3300 treating a patient's eye 3460. Laser pointer 3225 directs beam 3415 to a beamsplitter 3420 and out the collimator centered within the x-ray beam. The x-ray anode 3400 has a greatest dimension between about 50 microns and about 5 mm and can be placed from about 50 mm to about 200 mm from the retina. Maintaining the anode 3400 at this distance from the retina in one embodiment allows maintaining a low penumbra. The radiation beam 3410 is delivered through the collimator 3315, and its diverging path enters the eye approximately in the pars plana region 3470, missing the important structures of the anterior chamber such as the lens and the cornea. In some embodiments, a lens 3450 contacts the sclera or the cornea of the eye 3460 and can be used as a fiducial to direct the radiotherapy system. The collimator is typically within about 1 cm to about 12 cm from the beam entry point on the sclera.

Figure 12C:
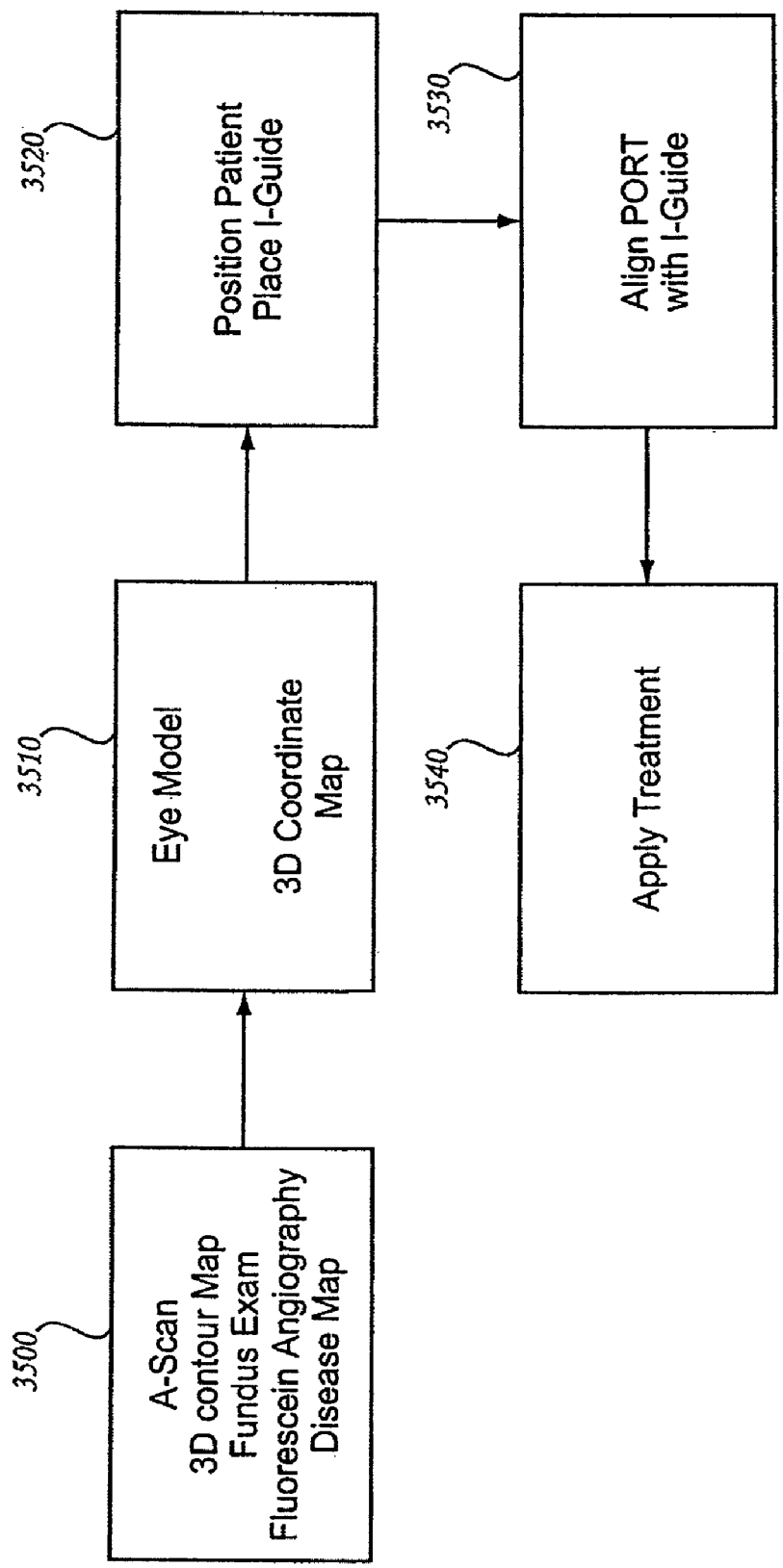
FIG. 12C depicts embodiments of a treatment planning process in accordance with embodiments described herein.

FIG. 12C depicts the clinical flow involving the radiotherapy device. An imaging modality and physical exam 3500 are used to create an eye model 3510, through which a 3D coordinate map is generated. The dose for a specific disease is chosen as is the maximum beam energy based on the region to be treated as well as the region to be avoided. These variables can be determined by treatment software as well as physician input related to the disease as well the depth of the diseased tissue. The patient is then positioned, and the optional contacting device is placed against or close to the eye of the patient 3520. The patient and guide are aligned with the guide 3530, and the treatment of a dose of radiation is applied 3540.

Figure 12D:
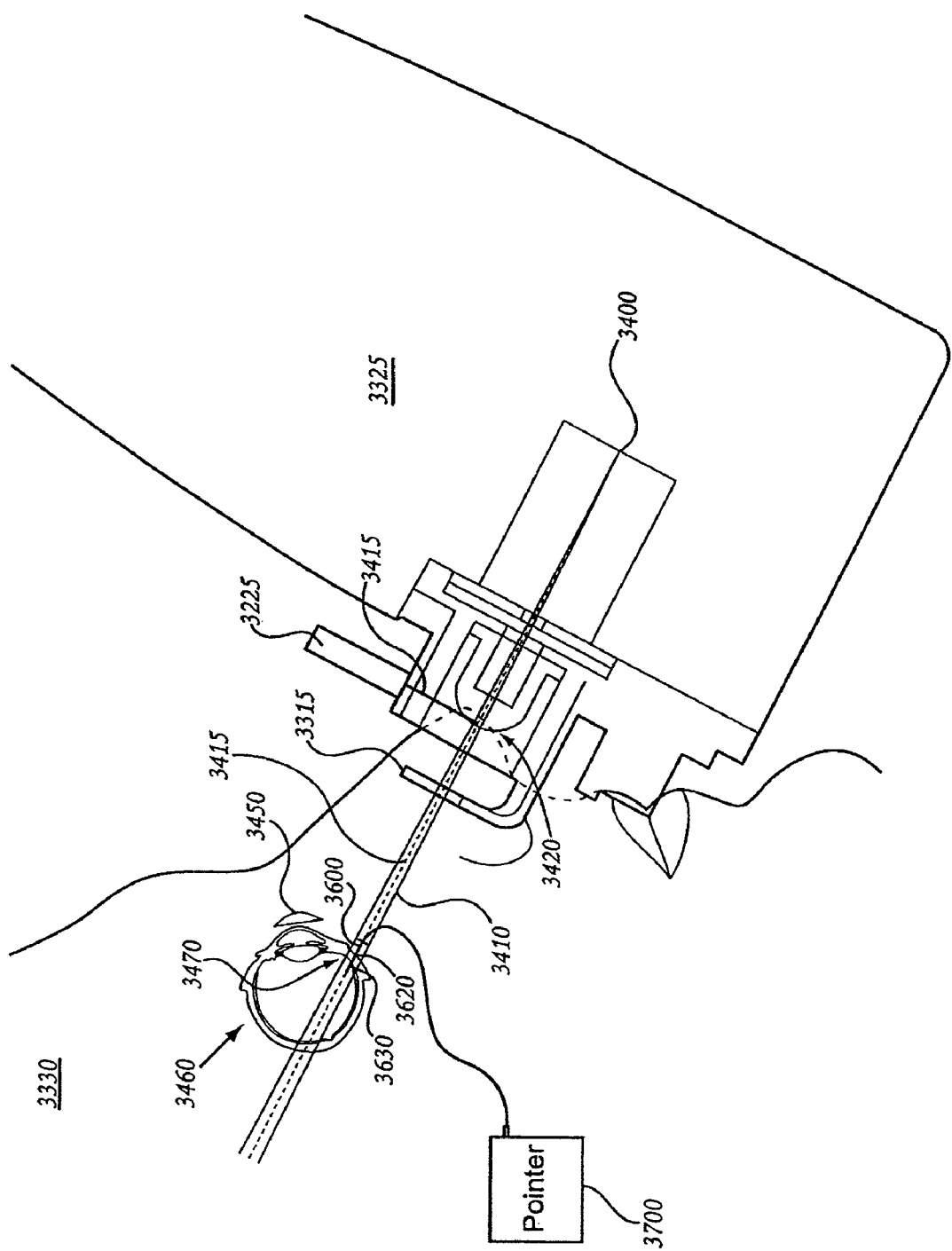
FIG. 12D depicts embodiments in which the radiotherapy device is aligned to a needle placed partially through the sclera.

FIG. 12D depicts a therapeutic set-up in which the radiotherapy device is aligned to a needle 3600 placed at least partially through the sclera 3620 and even into the vitreous 3630 of the eye. A light guide 3700, or pointer, can be placed into or coupled with the needle to illuminate the retina with a collimated light source. The needle 3600 and light guide 3700 can be stabilized within the sclera 3620 so that the collimated light source is stable on the point on the retina. The radiotherapy device can then be aligned with the needle 3600 and as such will deliver radiation in a straight line along the needle and along the light guide path and to the desired region of the retina. With this set-up, small regions of the retina can be precisely targeted.

Combination Therapy

Radiotherapy device 10 can be used in combination with other therapeutics for the eye. Radiotherapy can be used to limit the side effects of other treatments or can work synergistically with other therapies. For example, radiotherapy can be applied to laser burns on the retina or to implants or surgery on the anterior region of the eye. Radiotherapy can be combined with one or more pharmaceutical, medical treatments, and/or photodynamic treatments or agents. As used herein, "photodynamic agents" are intended to have their plain and ordinary meaning, which includes, without limitation, agents that react to light and agents that sensitize a tissue to the effects of light. For example, radiotherapy can be used in conjunction with anti-VEFG treatment, VEGF receptors, steroids, anti-inflammatory compounds, DNA binding molecules, oxygen radical forming therapies, oxygen carrying molecules, porphyryn molecules/therapies, gadolinium, particulate based formulations, oncologic chemotherapies, heat therapies, ultrasound therapies, and laser therapies.

In some embodiments, radiosensitizers and/or radioprotectors can be combined with treatment to decrease or increase the effects of radiotherapy, as discussed in Thomas, et al., Radiation Modifiers: Treatment Overview and Future Investigations, Hematol. Oncol. Clin. N. Am. 20 (2006) 119-139; Senan, et al., Design of Clinical Trials of Radiation Combined with Antiangiogenic Therapy, Oncologist 12 (2007) 465-477; the entirety of both these articles are hereby incorporated herein by reference. Some embodiments include radiotherapy with the following radiosensitizers and/or treatments: 5-fluorouracil, fluorinated pyrimidine antimetabolite, anti-S phase cytotoxin, 5-fluorouridine triphosphate, 2-deoxyfluorouridine monophosphate (Fd-UMP), and 2-deoxyfluorouridine triphosphate capecitabine, platinum analogues such as cisplatin and carboplatin, fluoropyrimidine, gemcitabine, antimetabolites, taxanes, docetaxel, topoisomerase I inhibitors, Irinotecan, cyclo-oxygenase-2 inhibitors, hypoxic cell radiosensitizers, antiangiogenic therapy, bevacizumab, recombinant monoclonal antibody, ras mediation and epidermal growth factor receptor, tumor necrosis factor vector, adenoviral vector Egr-TNF (Ad5.Egr-TNF), and hyperthermia. In some embodiments, embodiments include radiotherapy with the following radioprotectors and/or treatments: amifostine, sucralfate, cytoprotective thiol, vitamins and antioxidants, vitamin C, tocopherol-monoglucoside, pentoxifylline, alpha-tocopherol, beta-carotene, and pilocarpine.

Antiangiogenic Agents (AAs) aim to inhibit growth of new blood vessels. Bevacizumab is a humanized monoclonal antibody that acts by binding and neutralizing VEGF, which is a ligand with a central role in signaling pathways controlling blood vessel development. Findings suggest that anti-VEGF therapy has a direct antivascular effect in human tissues. In contrast, small molecule tyrosine kinase inhibitors (TKIs) prevent activation of VEGFRs, thus inhibiting downstream signaling pathways rather than binding to VEGF directly. Vascular damaging agents (VDAs) cause a rapid shutdown of established vasculature, leading to secondary tissue death. The microtubule-destabilizing agents, including combretastatins and ZD6126, and drugs related to 5,6-dimethylxanthenone-4-acetic acid (DMXAA) are two main groups of VDAs. Mixed inhibitors, including agents such as EGFR inhibitors or neutralizing agents and cytotoxic anticancer agents can also be used.

Radiodynamic Therapy

Radiodynamic therapy refers to the combination of collimated x-rays with a concomitantly administered systemic therapy. As used herein, the term "radiodynamic agents" is intended to have its ordinary and plain meaning, which includes, without limitation, agents that respond to radiation, such as x-rays, and agents that sensitize a tissue to the effects of radiation. Similar to photodynamic therapy, a compound is administered either systemically or into the vitreous; the region in the eye to be treated is then directly targeted with radiotherapy using the eye model described above. The targeted region can be precisely localized using the eye model and then radiation can be precisely applied to that region using the PORT system and virtual imaging system based on ocular data. Beam sizes of about 1 mm or less can be used in radiodynamic therapy to treat ocular disorders if the target is drusen for example. In other examples, the beam size is less than about 6 mm.

While certain aspects and embodiments of the disclosure have been described, these have been presented by way of example only, and are not intended to limit the scope of the disclosure. Indeed, the novel methods and systems described herein may be embodied in a variety of other forms without departing from the spirit thereof. The accompanying claims and their equivalents are intended to cover such forms or modifications as would fall within the scope and spirit of the disclosure.

What is claimed:

1. A method of planning radiation therapy for an eye, comprising:
   preparing a treatment plan for a delivery of an actual dose of radiation to a target at a region of the eye from at least one x-ray radiation beam, the preparing comprising:
   determining a first estimated dose of radiation to be delivered from an x-ray radiation source outside the eye to the target;
   determining a second estimated dose of radiation to be received by at least one of the optic nerve and the lens of the eye from the x-ray radiation source; and
   wherein the second estimated dose of radiation is equal to or less than about 40 percent of the first estimated dose; and
   wherein the treatment plan comprises at least one of a width of the at least one radiation beam, a distance from the radiation source to the target, a trajectory of the beam, a maximum beam energy, and the first estimated dose of radiation; and
   wherein the at least one of the width of the at least one radiation beam, the distance from the radiation source to the target, and the trajectory of the beam is selected to effect delivery of the first estimated dose to the target and the second estimated dose to the at least one of the optic nerve and the lens of the eye; and
   outputting information indicative of the treatment plan to an output module.

2. The method of claim 1, wherein at least one of the estimated dose of radiation to be received at the optic nerve and the estimated dose of radiation to be received at the lens is equal to or less than 20 percent of the estimated dose of radiation to be delivered to the target.

3. The method of claim 1, wherein at least one of the estimated dose of radiation to be received at the optic nerve and the estimated dose of radiation to be received at the lens is equal to or less than 10 percent of the estimated dose of radiation to be delivered to the target.

4. The method of claim 1, wherein at least one of the estimated dose of radiation to be received at the optic nerve and the estimated dose of radiation to be received at the lens is equal to or less than 5 percent of the estimated dose of radiation to be delivered to the target.

5. The method of claim 1, wherein at least one of the estimated dose of radiation to be received at the optic nerve and the estimated dose of radiation to be received at the lens is equal to or less than 1 percent of the estimated dose of radiation to be delivered to the target.

6. The method of claim 1, wherein the output module comprises at least one of a computer monitor, an LCD, an LED, a handheld device, a paper, a computer-readable medium, a computer-executable instruction, and a communication link to the radiation source.

7. The method of claim 1, further comprising delivering thermal energy to the eye during a period of between about 10 days before and about 3 days after delivery of the actual dose of radiation to the target.

8. The method of claim 1, further comprising delivering the actual dose of radiation to the target.

9. The method of claim 1, wherein at least one of the estimated dose of radiation to be delivered to the target, the estimated dose of radiation to be received at the optic nerve, and the estimated dose of radiation to be received at the lens is determined by a Monte Carlo simulation.

10. The method of claim 1, wherein at least one of the at least one radiation beam has a cross-sectional shape that is geometric.

11. The method of claim 10, wherein the geometric cross-sectional shape comprises at least one of an ellipse, a circle, a ring, concentric rings, a polygon, and a crescent.

12. The method of claim 1, wherein at least one of the estimated dose of radiation to be received at the optic nerve and the estimated dose of radiation to be received at the lens is based on a surface-to-depth beam energy representation.

13. The method of claim 1, wherein at least one of the estimated dose of radiation to be received at the optic nerve and the estimated dose of radiation to be received at the lens is based on tracing diverging rays from an x-ray source with a maximum beam energy less than about 250 keV.

14. The method of claim 1, further comprising:
   determining trajectories of a plurality of radiation beams to be delivered to the target, such that each of the plurality of beams traverses the sclera at a respective traversal zone; and
   wherein none of the traversal zones overlaps substantially with any other of the intersection zones.

15. The method of claim 14, wherein at least one of the plurality of beams overlaps with another of the plurality of beams at the target.

16. The method of claim 15, further comprising collimating the at least one radiation beam to a size having a cross-sectional dimension that is less than about 6 mm.

17. The method of claim 16, further comprising determining a filtration amount such that a dose of radiation to an exterior surface of the eye is less than 3 times a dose of radiation to the target, wherein the at least one radiation beam has an energy of from about 50 KeV to about 300 KeV.

18. The method of claim 17, wherein a first x-ray beam is filtered with a filter which at least partly comprises a heavy metal.

19. The method of claim 1, further comprising determining a current from about 1 mA to about 40 mA to be applied to a radiotherapy system such that a therapeutic dose of radiation to the target is administered in less than about 30 minutes.

20. The method of claim 1, wherein an x-ray beam is collimated and wherein said collimator is placed within about 20 centimeters of the target.

* * * * *